(12) United States Patent
Fukagawa et al.

(10) Patent No.: US 10,457,792 B2
(45) Date of Patent: *Oct. 29, 2019

(54) POLARIZING PLATE PROTECTIVE FILM, POLARIZING PLATE, AND DISPLAY DEVICE

(71) Applicant: FUJIFILM Corporation, Tokyo (JP)

(72) Inventors: Nobutaka Fukagawa, Kanagawa (JP); Naoki Sano, Kanagawa (JP); Mayumi Nojiri, Kanagawa (JP); Aiko Yoshida, Kanagawa (JP); Naoya Shimoju, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 244 days.

This patent is subject to a terminal disclaimer.

(21) Appl. No.: 15/497,824

(22) Filed: Apr. 26, 2017

(65) Prior Publication Data

US 2017/0226317 A1    Aug. 10, 2017

Related U.S. Application Data

(63) Continuation of application No. PCT/JP2015/080789, filed on Oct. 30, 2015.

(30) Foreign Application Priority Data

Oct. 31, 2014 (JP) ................................ 2014-223775
May 18, 2015 (JP) ................................ 2015-101025

(51) Int. Cl.
*C08K 5/12* (2006.01)
*C08K 5/07* (2006.01)
(Continued)

(52) U.S. Cl.
CPC ................ *C08K 5/12* (2013.01); *C07C 47/52* (2013.01); *C07C 47/575* (2013.01); *C07C 69/76* (2013.01);
(Continued)

(58) Field of Classification Search
CPC .... C08L 1/10; C08L 1/12; C08K 5/55; C08K 5/07; C08K 5/101; C08K 5/12;
(Continued)

(56) References Cited

U.S. PATENT DOCUMENTS

2013/0189449 A1* 7/2013 Fukagawa ............. C09K 19/52
                                                                428/1.33

FOREIGN PATENT DOCUMENTS

JP         2006215093 A  *  8/2006
JP         2008-007780 A     1/2008
(Continued)

OTHER PUBLICATIONS

Notification of Reasons for Refusal issued by the Japanese Patent Office dated Jan. 23, 2018, in connection with corresponding Japanese Patent Application No. 2016-556671.

(Continued)

*Primary Examiner* — Latosha Hines
(74) *Attorney, Agent, or Firm* — Edwards Neils LLC; Jean C. Edwards, Esq.

(57) ABSTRACT

A polarizing plate protective film which prevents deterioration of polarization performance in a high temperature, high humidity environment, and a polarizing plate and display device using the film including a compound represented by the following General Formula (I).

(X-L-)$_n$Z          General Formula (I)

X represents a formyl group, a boronic acid group, or a group represented by the following General Formula (I-B) or a group represented by the following General Formula (I-C), where L represents a single bond or divalent linking group, and n represents an integer equal to or greater than 2. When n is 2, Z represents a single bond or a divalent group, and when n≥3, Z represents an n-valent group.

(Continued)

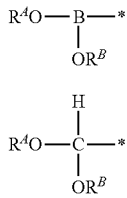

$R^A$ and $R^B$ represent an alkyl group, a cycloalkyl group, an aryl group, or an acyl group. $R^A$ and $R^B$ may be bonded to each other to form a ring. * represents a bond to be bonded to L.

11 Claims, 1 Drawing Sheet

(51) Int. Cl.
| | |
|---|---|
| C08K 5/55 | (2006.01) |
| C08L 1/10 | (2006.01) |
| C08K 5/06 | (2006.01) |
| C08L 1/12 | (2006.01) |
| G02F 1/1335 | (2006.01) |
| G02B 5/30 | (2006.01) |
| G02B 1/14 | (2015.01) |
| C07C 47/52 | (2006.01) |
| C07C 47/575 | (2006.01) |
| C07C 69/76 | (2006.01) |
| C07D 317/32 | (2006.01) |
| C07D 319/06 | (2006.01) |
| C07F 5/02 | (2006.01) |
| C08K 5/101 | (2006.01) |
| C08K 5/1565 | (2006.01) |
| C08K 5/1575 | (2006.01) |

(52) U.S. Cl.
CPC ......... *C07D 317/32* (2013.01); *C07D 319/06* (2013.01); *C07F 5/025* (2013.01); *C08K 5/06* (2013.01); *C08K 5/07* (2013.01); *C08K 5/101* (2013.01); *C08K 5/1565* (2013.01); *C08K 5/1575* (2013.01); *C08K 5/55* (2013.01); *C08L 1/10* (2013.01); *C08L 1/12* (2013.01); *G02B 1/14* (2015.01); *G02B 5/3025* (2013.01); *G02F 1/133528* (2013.01)

(58) Field of Classification Search
CPC ...... C08K 5/1565; C08K 5/1575; C08K 5/06; C07C 47/52; C07C 47/575; C07C 69/76; C07D 317/32; C07D 319/06; C07F 5/025; G02B 1/14; C02B 5/3025; G02F 1/133528
See application file for complete search history.

(56) References Cited

FOREIGN PATENT DOCUMENTS

| | | |
|---|---|---|
| JP | 2014-199413 A | 10/2014 |
| JP | 2014199413 A * | 10/2014 |
| JP | 2015-108099 A | 6/2015 |
| KR | 10-2014-0075154 A | 6/2014 |

OTHER PUBLICATIONS

International Search Report issued in connection with International Patent Application No. PCT/JP2015/080789 dated Jan. 19, 2016.
Written Opinion issued in connection with International Patent Application No. PCT/JP2015/080789 dated Jan. 19, 2016.

* cited by examiner

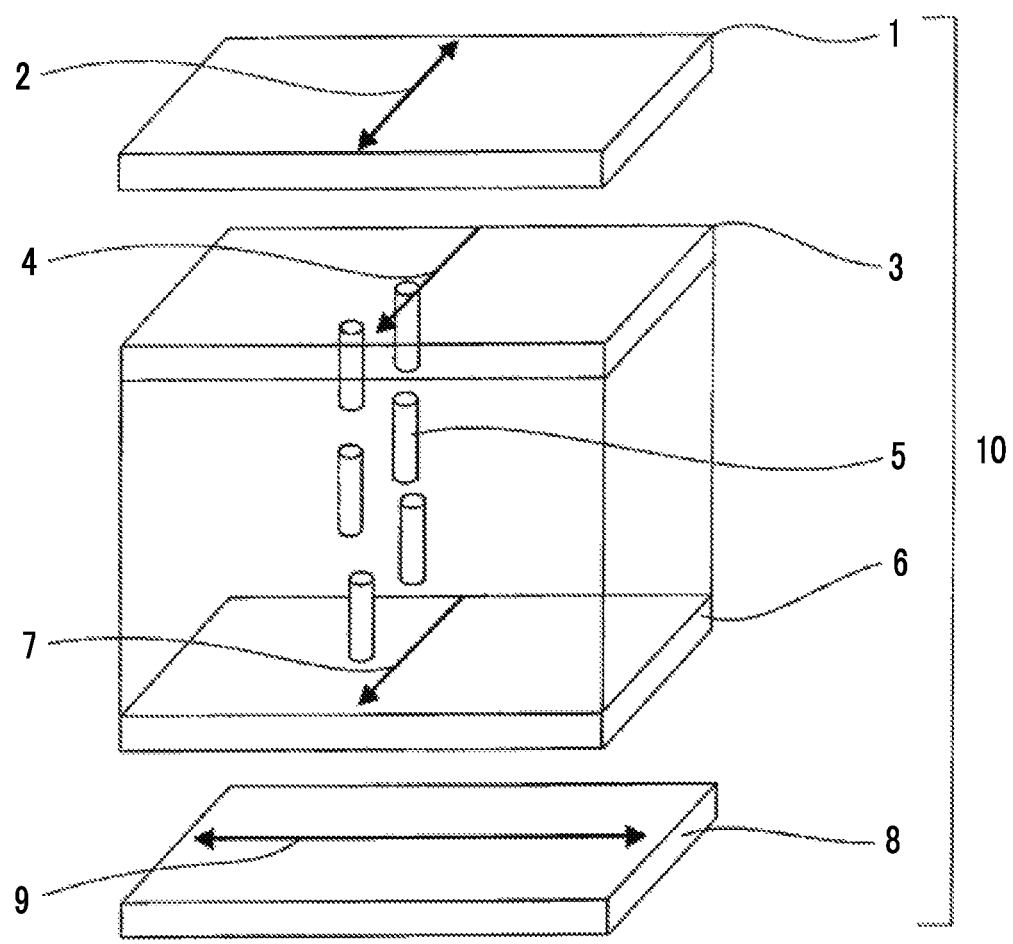

POLARIZING PLATE PROTECTIVE FILM, POLARIZING PLATE, AND DISPLAY DEVICE

CROSS-REFERENCE TO RELATED APPLICATIONS

This application is a Continuation of PCT International Application No. PCT/JP2015/080789 filed on Oct. 30, 2015, which was published under PCT Article 21(2) in Japanese, and which claims priority under 35 U.S.C. § 119 (a) to Japanese Patent Application No. 2014-223775 filed on Oct. 31 2014, and to Japanese Patent Application No. 2015-101025 filed on May 18, 2015. Each of the above applications is hereby expressly incorporated by reference, in its entirety, into the present application.

BACKGROUND OF THE INVENTION

1. Field of the Invention

The present invention relates to a polarizing plate protective film, a polarizing plate, and a display device.

2. Description of the Related Art

Liquid crystal display devices are gradually more widely used as space-saving type image display devices with low power consumption. Thinner liquid crystal display devices are even more required in accordance with an expansion of the market of so-called mobile devices such as mobile phones, tablet PCs, and the like, in addition to the market of televisions and the like in which high-definition images are required.

In a basic configuration of the liquid crystal display device, polarizing plates are provided on both sides of a liquid crystal cell. The polarizing plate has a role of passing light in a given direction, that is, only through the plane of polarization. In addition, performance of liquid crystal display devices greatly varies depending on the performance of polarizing plates. The polarizing plate is generally configured with a polarizer formed of a polyvinyl alcohol film and the like in which iodine or a dye is adsorbed and oriented, and transparent protective film (polarizing plate protective films) which are bonded to both front and rear sides of the polarizer.

When the polarizing plate is used for a long time, display performance is deteriorated due to heat, wet heat, or ultraviolet rays. The deterioration of the display performance is mainly due to deterioration of the polarizer configuring the polarizing plate. Along with the thinning of the polarizing plates, the polarizers are more easily deteriorated.

Meanwhile, means for adding an ultraviolet absorbent to a polarizing plate protective film are used to respond the deterioration of the display performance due to ultraviolet rays. However, regarding the deterioration of the polarizer due to heat or wet heat, although further improvement is required along with the thinning of the polarizing plates, there are presently no means for sufficiently dealing with such requirement.

In addition, a cross-linking agent disclosed in JP2008-7780A has been proposed as an additive to be added to the polarizing plate protective film. This is a technology of crosslinking a cellulose ester film to improve adhesiveness between the cellulose ester film and a polarizer and is not a technology of improving durability of a polarizing plate.

SUMMARY OF THE INVENTION

The invention is made in consideration of these circumstances.

Thus, an object of the invention is to improve durability of a polarizing plate under a high temperature and high humidity condition and preventing deterioration of polarization performance.

The object of the invention is particularly to provide a polarizing plate protective film capable of preventing deterioration of polarization performance under a high temperature and high humidity condition, and a polarizing plate and a display device using such a polarizing plate protective film.

The inventors analyzed the causes of deterioration of a polarizer under a high temperature and high humidity condition, and found a change in physical properties of a resin configuring a polarizer. It was assumed that a change in physical properties particularly causes a decrease in a degree of crosslinking of a crosslinked resin and promotes crystallization of the resin.

Therefore, the inventors intensively researched materials which can be diffused and moved from a polarizing plate protective film to a polarizer under a high temperature and high humidity condition and means therefor, from a viewpoint of preventing a change in physical properties of a resin, particularly, crystallization of a resin.

As a result, the inventors found that specified compounds are effective and completed the invention.

That is, the problems were solved with the following means.

(1) A polarizing plate protective film comprising: a compound represented by the following General Formula (I).

$$(X-L)_n Z \qquad \text{General Formula (I)}$$

In General Formula (I), X represents a formyl group, a boronic acid group, and a group represented by the following General Formula (I-B) or a group represented by the following General Formula (I-C). L represents a single bond or divalent linking group, and n represents an integer equal to or greater than 2. When n is 2, Z represents a single bond or a divalent group, and when n is equal to or greater than 3, Z represents an n-valent group. Here, a plurality of -L-X's may be the same as each other or different from each other. However, among a plurality of X's, the number of the group represented by General Formula (I-B) and the group represented by the General Formula (I-C) is respectively 0 or 1, and when n is 2, both of L and Z may not be a single bond.

General Formula (I-B)

General Formula (I-C)

In General Formulae (I-B) and (I-C), $R^A$ and $R^B$ each independently represent an alkyl group, a cycloalkyl group, an aryl group, or an acyl group. Here, $R^A$ and $R^B$ may be bonded to each other to form a ring. * represents a bond to be bonded to L.

(2) The polarizing plate protective film according to (1), in which the compound represented by General Formula (I) is represented by any of the following General Formulae (II-1) to (II-5).

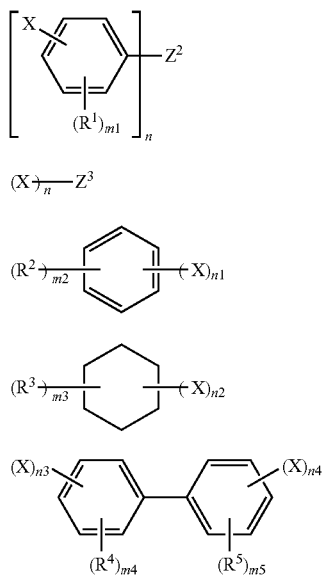

General Formula (II-1)

General Formula (II-2)

General Formula (II-3)

General Formula (II-4)

General Formula (II-5)

In General Formulae (II-1) to (II-5), X and n are identical to X and n of General Formula (I). When n is 2, $Z^2$ represents a divalent group, and when n is equal to or greater than 3, $Z^2$ represents an n-valent group. When n is 2, $Z^3$ represents an alkylene group, and when n is equal to or greater than 3, $Z^3$ represents an n-valent alkyl group. However, $Z^3$ does not have a ring structure. $R^1$ to $R^5$ each independently represent a substituent. n1 represents an integer of 2 to 6, n2 represents an integer of 2 to 12, and n3 and n4 each independently represent an integer of 1 to 5. m1, m2, m4, and m5 each independently represent an integer of 0 to 4, and m3 represents an integer of 0 to 10.

(3) The polarizing plate protective film according to (1) or (2), in which the compound represented by General Formula (I) includes at least one benzene ring.

(4) The polarizing plate protective film according to any one of (1) to (3), in which the compound represented by General Formula (I) is represented by General Formula (II-1) or (II-3).

(5) The polarizing plate protective film according to any one of (1) to (4), in which the n is an integer of 2 to 4, and the total number of carbon atoms of component parts other than X is equal to or smaller than 40.

(6) The polarizing plate protective film according to any one of (1) to (5), in which the number of shortest linking atoms which link two X's with each other is equal to or smaller than 20 between every two X's.

(7) The polarizing plate protective film according to any one of (1), (3), (5), and (6), in which the Z is a single bond. —O—, —S—, —SO—, —SO$_2$—, —OC(=O)—, —C($R^{a1}$)($R^{a2}$)—, >C<, (—OCH$_2$CH$_2$)$_2$C(CH$_2$CH$_2$O—)$_2$, >C($R^{a3}$)—, >N—, or —N(Ra)—, $R^{a1}$ to $R^{a3}$ each independently represent a hydrogen atom, an alkyl group, or an aryl group, and Ra represents a hydrogen atom, an alkyl group, an aryl group, or an acyl group.

(8) The polarizing plate protective film according to any one of (1) to (7), including cellulose acylate.

(9) A polarizing plate comprising: the polarizing plate protective film according to any one of (1) to (8) on both sides or one side of a polarizer.

(10) The polarizing plate according to (9) further comprising a compound represented by the following General Formula (A) on at least one polarizing plate protective film which is bonded to both sides or one side of the polarizer.

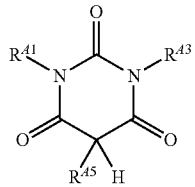

General Formula (A)

In General Formula (A), $R^{41}$ and $R^{43}$ each independently represent a hydrogen atom, an alkyl group, a cycloalkyl group, an alkenyl group, or an aromatic group. Here, an alkyl group, a cycloalkyl group, an alkenyl group, or an aromatic group may include a substituent. $R^{45}$ represents a hydrogen atom or a substituent.

(11) A display device comprising at least one polarizing plate according to (9) or (10).

In this specification, a numerical range shown with "to" means to include numerical values before and after "to" as the lower limit value and the upper limit value.

Here, in this specification, a group capable of including a substituent (for example, a group including an alkyl part, an aryl part, or a heterocyclic part) may include a substituent, unless otherwise noted. For example, an alkyl group is an alkyl group which may include a substituent, and an aryl group or an aromatic group may be an aryl group or an aromatic group which may include a substituent.

In addition, in a case of including at least two substituents in the same atom, these substituents may be bonded to each other to form a ring, or in a case where an adjacent bonding atom includes each substituent, these substituents may be bonded to each other to form a ring.

Further, in a case where a plurality of groups having the same reference numerals are present, or in a case where a plurality of groups having the same reference numerals are present as a result of a plurality of repeating, these groups may be the same as each other or different from each other.

In this specification, when defining a plurality of substituents or linking groups (hereinafter, referred to as substituents and the like) at the same time or selectively, the substituents and the like may be respectively the same as each other or different from each other.

The substituent refers to substituent S, unless otherwise noted.

According to the invention, it is possible to improve durability of a polarizing plate under a high temperature and high humidity condition and prevent deterioration of polarization performance.

As a result, it is possible to provide a polarizing plate protective film capable of preventing deterioration of polarization performance under a high temperature and high humidity condition, and it is possible to improve durability of a polarizing plate in a high temperature and high humidity environment by using such a polarizing plate protective film, even when a polarizer or the polarizing plate protective film is thinned, and it is possible to provide a polarizing plate and a display device having excellent durability.

Further, a compound used in the present invention satisfies performance required in the related art, such as not occurring bleeding out or preventing haze.

The characteristics and advantages described above and other characteristics and advantages of the invention may be shown more clearly according to the following descriptions with reference to the suitably accompanying drawings.

BRIEF DESCRIPTION OF THE DRAWINGS

FIG. 1 is a perspective view schematically showing an exploded laminate as an example of an embodiment of a display device using a polarizing plate of the invention.

DESCRIPTION OF THE PREFERRED EMBODIMENTS

Hereinafter, the invention will be described in order from a polarizing plate protective film.

<<Polarizing Plate Protective Film>>

A polarizing plate protective film may have any one of formats of a single layer or a laminate including a plurality of layers.

In a case where the polarizing plate protective film is a laminate including two or more layers, the layer structure is preferably a two-layer structure or a three-layer structure, and is more preferably three-layer structure. In a case of the three-layer structure, the layer structure preferably includes one core layer (that is, the thickest layer, and hereinafter, also referred to a base layer), and a skin layer A and a skin layer B interposing the core layer. In the invention, the layer structure is preferably a three-layer structure of skin layer B/core layer/skin layer A. When manufacturing the polarizing plate protective film by solution film forming, the skin layer B is a layer adjacent to a metal support which will be described later, and the skin layer A is a layer on an air interface on a side opposite to the metal support. The skin layer A and the skin layer B are collectively referred to as the skin layers (or surface layers).

The polarizing plate protective film of the invention at least includes a compound represented by General Formula (I). Hereinafter, the compound represented by General Formula (I) of the invention will be described.

<Compound Represented by General Formula (I)>

In the polarizing plate, polarizing plate protective films are laminated to be bonded to both sides or one side of a polarizer, and the compound represented by General Formula (I) of the invention is included in the polarizing plate protective film adjacent to the polarizer, and thus, it is possible to improve durability of the polarizer (also referred to as polarizing sheet durability), particularly, durability in a high temperature and high humidity condition.

The inventors found that, physical properties of a resin configuring the polarizer change, after the resin swells under the high temperature and high humidity condition. It was assumed that a reason of this change was due to a change in a degree of crosslinking of the crosslinked resin, and this decrease in a degree of crosslinking was due to a decrease in an amount of a crosslinking agent.

Particularly, in a case where the resin configuring the polarizer is polyvinyl alcohol, an effect of improving the polarizing sheet durability is excellent the compound represented by General Formula (I) of the invention, and thus, the following mechanism is assumed.

That is, polyvinyl alcohol is normally crosslinked by boric acid. When physical properties of polyvinyl alcohol change under the high temperature and high humidity condition, a polyvinyl alcohol-iodine complex is partially decomposed and the polarizer is deteriorated. Meanwhile, when the amount of boric acid of the crosslinking agent is decreased, polyvinyl alcohol is crystallized.

Here, it is considered that the compound represented by General Formula (I) of the invention present in the polarizing plate protective film is diffused and moved from the polarizing plate protective film to the polarizer in the high temperature and high humidity condition, to prevent a change in physical properties of polyvinyl alcohol, for example, crystallization of polyvinyl alcohol due to partial decomposition of boric acid crosslinking due to a decrease in the amount of boric acid.

$(X-L)_n Z$  General Formula (I)

In General Formula (I), X represents a formyl group, a boronic acid group, a group represented by the following General Formula (I-B) or a group represented by the following General Formula (I-C), L represents a single bond or divalent linking group, and n represents an integer equal to or greater than 2. When n is 2, Z represents a single bond or a divalent group, and when n is equal to or greater than 3, Z represents an n-valent group. Here, a plurality of -L-X's may be the same as each other or different from each other. However, among a plurality of X's, the number of the group represented by General Formula (I-B) or the group represented by the General Formula (I-C) is respectively 0 or 1, and when n is 2, both of L and Z may not be a single bond.

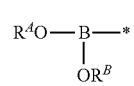

General Formula (I-B)

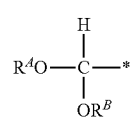

General Formula (I-C)

In General Formulae (I-B) and (I-C), $R^A$ and $R^B$ each independently represent an alkyl group, a cycloalkyl group, an aryl group, or an acyl group. Here, $R^A$ and $R^B$ may be bonded to each other to form a ring. * represents a bond to be bonded to L.

L represents a single bond or a divalent linking group, and examples of the divalent linking group include an alkylene group, a cycloalkylene group, an arylene group, or a divalent heterocyclic group.

Among these, an arylene group and a divalent heterocyclic group are preferable, an arylene group and a heteroarylene group are more preferable, and an arylene group is even more preferable.

Examples of the arylene group include phenylene and naphthylene, and phenylene is preferable. As a heterocycle of a heteroarylene group, a 5- or 6-membered heteroaromatic ring in which a ring-constituting atom includes a hetero atom selected from an oxygen atom, a sulfur atom, and a nitrogen atom. The heterocycle may be formed as a ring with a benzene ring, and examples thereof include a furan ring, a thiazole ring, a pyrrole ring, and a pyridine ring.

An arylene group or a hetero ring may include a substituent, and, as such a substituent, a group selected from the substituents S will be described later is used.

n represents an integer equal to or greater than 2, and is preferably 2 to 6, more preferably 2 to 4, and even more preferably 2.

When n is 2, Z represents a single bond or a divalent group, and when n is equal to or greater than 3. Z represents an n-valent group, that is, tri- or higher valent group.

Examples of the divalent group include —O—, —S—, —SO—, —SO$_2$—, —N(Ra)—, —OC(=O)—, an alkylene group, a cycloalkylene group, an arylene group, a divalent heterocyclic group (preferably a heteroarylene group), and a group obtained by combining these groups with each other. Here, Ra is a hydrogen atom, an alkyl group, an aryl group, or an acyl group.

Examples of the group obtained by combining these groups with each other include —O-alkylene-O—, —O-[alkylene-O]$_l$—, —C(=O)O—Y—OC(=O)—, —OC(=O)—Y—C(=O)O—, —OC(=O)—Y—OC(=O)—, —C(=O)O-alkylene-cycloalkylene-alkylene-OC(=O)—, —OC(=O)-alkylene-cycloalkylene-alkylene-C(=O)O—, —OC(=O)-alkylene-cycloalkylene-alkylene-OC(=O)—, and —OC(=O)O—.

Here, l represents an integer of 1 to 10 and Y represents an alkylene group, a cycloalkylene group, an arylene group, or a divalent heterocyclic group.

An alkylene group is also preferably —C(R$^{a1}$)(R$^{a2}$)—, and R$^{a1}$ and R$^{a2}$ each independently represent a hydrogen atom, an alkyl group, or an aryl group.

Examples of a trivalent group include >C(R$^{a3}$)—, >N—, a trivalent cycloalkyl group, a trivalent aryl group, and a trivalent heteroaryl group. Here, R$^{a3}$ represents a hydrogen atom, an alkyl group, or an aryl group.

Examples of a tetravalent group include >C<, (—OCH$_2$CH$_2$)$_2$C(CH$_2$CH$_2$O—)$_2$, and a tetravalent aryl group.

In the invention, as Z, a single bond, —O—, —S—, —SO—, —SO$_2$—, —OC(=O)—, —C(R$^{a1}$)(R$^{a2}$)—, >C<, (—OCH$_2$CH$_2$)$_2$C(CH$_2$CH$_2$O—)$_2$, >C(R$^{a3}$)—, >N—, or —N(Ra)— is preferable aspects.

X represents a formyl group (—CHO), a boronic acid group [boronyl group of —B(OH)$_2$], the group represented by General Formula (I-B), or the group represented by General Formula (I-C).

Here, among a plurality of X's, the number of the group represented by General Formula (I-B) and the group represented by the General Formula (I-C) is respectively 0 or 1.

In the invention, among a plurality of X's, one or more X's are preferably a formyl group or a boronic acid group, and one or more X's are more preferably a formyl group.

In addition, in the invention, it is also preferable that at least one substituent selected from a boronic acid group, the group represented by General Formula (I-B), and the group represented by General Formula (I-C) is included together with at least one formyl group, or at least one substituent selected from a formyl group, the group represented by General Formula (I-B), and the group represented by General Formula (I-C) is included together with at least one boronic acid group. Among these, all of X's is preferably a formyl group or a boronic acid group, and all of X's is particularly preferably a formyl group.

Hereinafter, the group represented by General Formula (I-B) and the group represented by General Formula (I-C) will be described.

The alkyl group of R$^A$ and R$^B$ may be linear or branched and the number of carbon atoms is preferably 1 to 12 and more preferably 1 to 8. Examples of the alkyl group include methyl, ethyl, n-propyl, isopropyl, n-butyl, isobutyl, s-butyl, t-butyl, n-hexyl, n-octyl, 2-ethylhexyl, n-decyl, n-dodecyl, benzyl, phenoxyethyl, and methoxyethyl.

The number of carbon atoms of cycloalkyl group of R$^A$ and R$^B$ is preferably 3 to 12, more preferably 5 to 12, and even more preferably 5 to 8. Examples of the cycloalkyl group include cyclopropyl, cyclopentyl, cyclohexyl, and cyclopentyl and cyclohexyl are preferable.

The number of carbon atoms of the aryl group of R$^A$ and R$^B$ is preferably 6 to 20, more preferably 6 to 16, and even more preferably 6 to 12. Examples of the aryl group include phenyl and naphthyl, and a phenyl group which may include a substituent is preferable.

The acyl group of R$^A$ and R$^B$ represents a formyl group, an alkylcarbonyl group, an alkenylcarbonyl group, a cycloalkylcarbonyl group, an arylcarbonyl group, and a heterocyclic carbonyl group. The number of carbon atoms of the alkylcarbonyl group is preferably 2 to 20, the number of carbon atoms of the alkenylcarbonyl group is preferably 3 to 20, the number of carbon atoms of the cycloalkylcarbonyl group is preferably 4 to 20, the number of carbon atoms of the arylcarbonyl group is preferably 7 to 20, and the number of carbon atoms of the heterocyclic carbonyl group is preferably 1 to 20.

Examples of these groups include acetyl, propionyl, pivaloyl, myristoyl, acryloyl, methacryloyl, cyclopropylcarbonyl, cyclopentylcarbonyl, cyclohexylcarbonyl, benzoyl, naphthoyl, and nicotinoyl.

Among the acyl groups, in the invention, an alkylcarbonyl group and an arylcarbonyl group are preferable.

Each group of R$^A$ and R$^B$ may be further substituted with a substituent, and examples of such a substituent include groups selected from the substituent S which will be described later.

In General Formulae (I-B) and (I-C), a ring formed by the bonding of R$^A$ and R$^B$ to each other is preferably a 5-membered to 7-membered ring, and more preferably 5-membered or 6-membered ring. In General Formula (I-B), 1,3,2-dioxaborolane ring, a 1,3,2-dioxaborinane ring is more preferable, and in General Formula (I-C), a 1,3-dioxolane ring or a 1,3-dioxane ring is more preferable.

The ring formed by the bonding of R$^A$ and R$^B$ to each other may include a substituent, and examples of such a substituent include groups selected from the substituent S which will be described later.

The group represented by General Formula (I-B) is preferably a group represented by General Formula (I-B-1), General Formula (I-B-2), or General Formula (I-B-3).

Among these group, the groups represented by General Formula (I-B-2) General Formula (I-B-3) is more preferable, from a viewpoint of improving the effects of the invention.

General Formula (I-B-1)

General Formula (I-B-2)

General Formula (I-B-3)

In General Formulae (I-B-1), (I-B-2), and (1-B-3), R$^{AC1}$ and R$^{AC2}$ each independently represent an alkyl group, a cycloalkyl group, an aryl group, or an acyl group. Here, $R^{AC1}$ and $R^{AC2}$ are not bonded to each other to form a ring.

$R^{AC3}$ and $R^{AC12}$ each independently represent a hydrogen atom, an alkyl group, cycloalkyl group, an aryl group, an acyl group, an alkoxy group, or an alkoxycarbonyl group. Here, at least two of $R^{AC3}$ and $R^{AC6}$ and at least two of $R^{AC7}$ and $R^{AC12}$ may be bonded to each other to form a ring.

* represents a bond to be bonded to L.

The alkyl group, the cycloalkyl group, the aryl group, and the acyl group of $R^{AC1}$ and $R^{AC12}$ are identical to the alkyl group, the cycloalkyl group, the aryl group, and the acyl group of General Formula (I-B) and preferred ranges are also the same as each other.

The number of carbon atoms of the alkoxy group of $R^{AC3}$ and $R^{AC12}$ is preferably 1 to 20 and more preferably 2 to 16. Examples of the alkoxy group include methoxy, ethoxy, isopropoxy, hexyloxy, and 2-ethylhexyloxy. In addition, the alkoxy group may be include a substituent and may have a ring structure.

The number of carbon atoms of the alkoxycarbonyl group of $R^{AC3}$ and $R^{AC12}$ is preferably 2 to 12, more preferably 2 to 8, and even more preferably 2 to 6. Examples of the alkoxycarbonyl group include methoxycarbonyl, ethoxycarbonyl, isopropoxycarbonyl, n-butoxycarbonyl, t-butoxycarbonyl, 2-ethylhexyloxycarbonyl, and benzyloxycarbonyl.

The alkyl group, the cycloalkyl group, the aryl group, and the acyl group of $R^{AC1}$ and $R^{AC12}$ and the alkoxy group and the alkoxycarbonyl group of $R^{AC3}$ and $R^{AC12}$ may further include a substituent, and examples of such a substituent include groups selected from the substituent S which will be described later. Among such substituents, an alkyl group, a cycloalkyl group, an aryl group, an alkoxy group, an aryloxy group, an alkylthio group, an arylthio group, an acyl group, an alkoxycarbonyl group, a carbamoyl group, a sulfamoyl group, a sulfonyl group, a cyano group, a halogen atom, and a hydroxy group are preferable.

Particularly, in a case where $R^{AC1}$ and $R^{AC12}$ are the substituted alkyl group, an alkyl group substituted with an aryl group, an alkoxy group, an alkoxycarbonyl group, a cyano group, a halogen atom, and a hydroxy group are preferable.

A ring formed by the bonding of at least two of $R^{AC3}$ to $R^{AC6}$ to each other or a ring formed by the bonding of at least two of $R^{AC7}$ to $R^{AC12}$ to each other is preferably 5-membered or 6-membered ring, and a cyclopentane ring and a cyclohexane ring are more preferable.

These rings may include a substituent, and examples of such a substituent include groups selected from the substituent S which will be described later.

$R^{AC1}$ and $R^{AC2}$ are preferably an alkyl group or an acyl group and more preferably an alkyl group.

$R^{AC3}$ and $R^{AC6}$ are preferably a hydrogen atom, an alkyl group, an alkoxy group, and an alkoxycarbonyl group, or more preferably a hydrogen atom or an alkyl group. In addition, a case where all of $R^{AC3}$ and $R^{AC6}$ are hydrogen atoms, a case where at least two thereof are hydrogen atoms, or a case where all thereof is an alkyl group is are preferable.

$R^{AC7}$ and $R^{AC12}$ are preferably a hydrogen atom or an alkyl group.

The group represented by General Formula (I-C) is preferably a group represented by General Formula (I-C-1), General Formula (I-C-2), or General Formula (I-C-3).

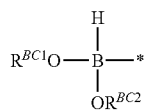

General Formula (I-C-1)

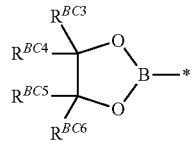

General Formula (I-C-2)

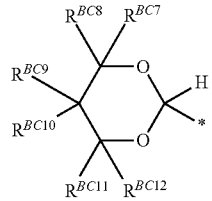

General Formula (I-C-3)

In General Formulae (I-C-1), $R^{BC1}$ and $R^{BC2}$ each independently represent an alkyl group, a cycloalkyl group, an aryl group, or an acyl group. Here, $R^{BC1}$ and $R^{BC2}$ are not bonded to each other to form a ring.

In General Formulae (I-C-2) and (I-C-3), $R^{BC3}$ to $R^{BC12}$ each independently represent a hydrogen atom, an alkyl group, cycloalkyl group, an aryl group, an acyl group, an alkoxy group, or an alkoxycarbonyl group. Here, at least two of $R^{BC3}$ and $R^{BC6}$ and at least two of $R^{B7}$ and $R^{BC12}$ may be bonded to each other to form a ring.

* represents a bond to be bonded to L.

$R^{BC1}$ and $R^{BC2}$ are identical to $R^A$ and $R^B$ of General Formula (I-C) except for that $R^{BC1}$ and $R^{BC2}$ are not bonded to each other to form a ring, and the preferred ranges are also the same as each other.

The alkyl group of $R^{BC1}$ and $R^{BC2}$ are also preferably alkyl group substituted with an aryl group, a halogen atom, an alkoxy group, an aryloxy group, an alkoxycarbonyl group, or cyano group.

$R^{BC3}$ and $R^{BC12}$ are identical to $R^{AC3}$ and $R^{AC12}$ of General Formula (I-B-2) and (I-B-3), and the preferred ranges are also the same as each other.

The compound represented by General Formula (I) preferably includes at least one benzene ring, and the number of benzene rings is preferably 1 to 4, more preferably 2 to 4, even more preferably 2 or 3, and particularly preferably 2.

In addition, in the compound represented by General Formula (I), the total number of carbon atoms of component parts other than X is preferably equal to or smaller than 40, more preferably 6 to 40, and even more preferably 12 to 24. Among these, it is particularly preferable that n is 2 to 4.

It is preferable that the total number of carbon atoms of component parts other than X is in the preferred range described above, from a viewpoint of easily diffusing the compound represented by General Formula (I) to the polarizer.

Here, the number of shortest linking atoms which links two X's with each other is preferably equal to or smaller than 20, more preferably 2 to 20, even more preferably 6 to 20, and still more preferably 8 to 20, between every two X's.

The number of shortest linking atoms which links two X's with each other is the same in any case where X is a formyl group, a boronic acid group, the group represented by the following General Formula (I-B), or the group represented by the following General Formula (I-C).

In addition, the number of shortest linking atoms which links two X's with each other will be described with the following compounds (X is a formyl group), as an example. The number of carbon atoms is counted from the first carbon atom bonded to a formyl group which is X, and the numbers of carbon atoms bonded to a formyl group which is another X are 8 and 12 from the top, and thus, the number of shortest linking atoms is respectively 8 and 12.

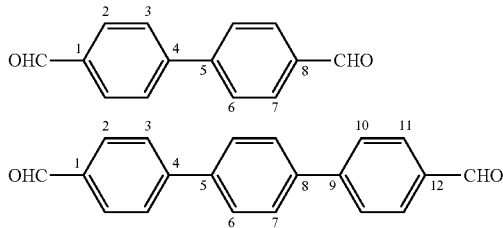

The compound represented by General Formula (I) is preferably a compound represented by any of the following General Formulae (II-1) to (II-5).

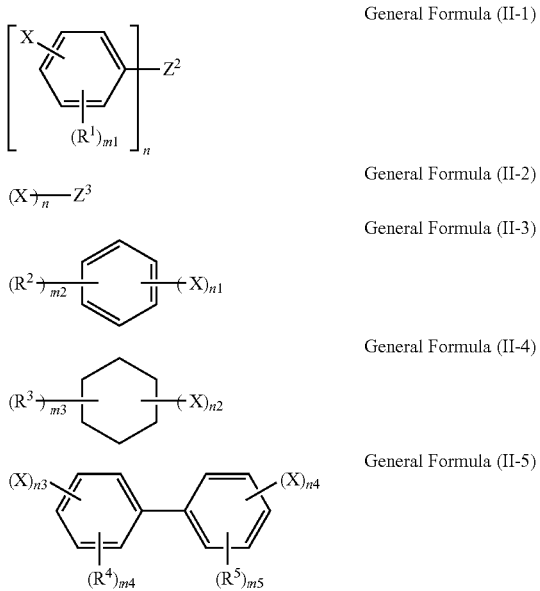

In General Formulae (II-1) to (II-5), X and n are identical to X and n of General Formula (I). When n is 2, $Z^2$ represents a divalent group, and when n is equal to or greater than 3, $Z^2$ represents an n-valent group. When n is 2, $Z^3$ represents an alkylene group, and when n is equal to or greater than 3, $Z^3$ represents an n-valent alkyl group. However, $Z^3$ does not have a ring structure. $R^1$ to $R^5$ each independently represent a substituent, n1 represents an integer of 2 to 6, n2 represents an integer of 2 to 12, and n3 and n4 each independently represent an integer of 1 to 5, m1, m2, m4, and m5 each independently represent an integer of 0 to 4, and m3 represents an integer of 0 to 10.

As the substituent of $R^1$ to $R^5$, a group selected from the substituents S which will be described later is used.

Among these, the substituent of $R^1$ to $R^5$ is preferably an alkyl group, an aryl group, an alkoxy group, and a halogen atom.

A divalent group and an n-valent group of $Z^2$ is preferably the divalent group and the n-valent group of Z of General Formula (I).

m1 to m5 are preferably an integer of 0 to 2, more preferably 0 or 1, and even more preferably 0.

In a case where m1 to m5 are equal to or greater than 2, in each of m1 to m5, a plurality of substituents may be bonded to each other to form a ring.

Here, $R^1$ and $Z^2$ may be bonded to each other to form a ring and $R^4$ and $R^5$ may be bonded to each other to form a ring.

n1 and n2 are preferably an integer of 2 to 4 and more preferably 2.

n3 and n4 are preferably 1 or 2 and more preferably 1.

In General Formulae (II-1), (II-3), and (II-5), it is preferable that $R^1$, $R^2$, $R^4$, $R^5$, and $Z^2$ are electron-attractive groups.

When $R^1$, $R^2$, $R^4$, and $R^5$ are electron-attractive groups, X receives electronic effects thereof, and thus, the effects of the invention are more effectively exhibited.

A σ value of Hanunmmett's rule of the electron-attractive groups is equal to or greater than −0.10, more preferably equal to or greater than 0. Here, regarding the σ value, in a case where sites of substitution with respect to X are o and p parts, a σp value is used, and in a case where the site of substitution is m part, σm value is used.

Examples of a substituent having a positive σp value include a halogen atom such as fluorine (0.06), chlorine (0.23), bromine (0.23), or iodine (0.18), a group including carbonyl such as —CHO(0.42), —COCH$_3$(0.50), —COC$_6$H$_5$(0.46), —CONH$_2$(0.36), —COOH(0.41), —COOCH$_3$(0.39), or —COOC$_2$H$_5$(0.45), a group including sulfonyl or sulfinyl such as —SOCH$_3$(0.49), —SO$_2$CH$_3$ (0.72), —SO$_2$C$_6$H$_5$(0.68), —SO$_2$CF$_3$(0.93), —SO$_2$NH$_2$ (0.57), —SO$_2$OC$_6$H$_5$(0.23), —SO$_3$$^-$(0.09), or —SO$_3$H (0.50), a nitrogen-containing substituent such as —CN (0.66), —NO$_2$(0.78), —N(CH$_3$)$_3$$^+$(0.82), or —N(CF$_3$)$_2$ (0.53), and halogen atom-substituted alkyl group such as —CCl$_3$(0.46), —CH$_2$Cl(0.18), —CHCl$_2$(0.32), or —CF$_3$ (0.54). Here, the numerical values in brackets are the σp values.

Examples of a substituent having a positive σm value include an alkoxy group or an aryloxy group such as —OH(0.12), —OCH$_3$(0.12), or —OC$_6$H$_5$(0.25), an alkylthio group or an arylthio group such as —SCH$_3$(0.16), an ethynyl group (0.20), an unsaturated hydrocarbon group such as —C$_6$H$_5$(0.10), a halogen atom such as Fluorine (0.35), chlorine (0.37), bromine (0.39), or iodine (0.35), a group including carbonyl such as —CHO(0.42), —COCH$_3$ (0.38), —COC$_6$H$_5$(0.36), —CONH$_2$(0.32), —COOH(0.37), or —COOCH$_3$(0.36), a group including sulfonyl or sulfinyl such as —SOCH$_3$(0.52), —SO$_2$CH$_3$(0.70), —SO$_2$C$_6$H$_5$ (0.62), —SO$_2$CF$_3$(0.83), —SO$_2$NH$_2$(0.62), or —SO$_3$H (0.55), a nitrogen-containing substituent such as —CN (0.62), —NO$_2$(0.71), —N(CH$_3$)$_3$$^+$(0.88), —N(CF$_3$)$_2$(0.40), and a halogen atom-substituted alkyl group such as —CCl$_3$ (0.40), —CH$_2$Cl(0.11), —CHCl$_2$(0.31), or —CF$_3$(0.49). Here, the numerical values in brackets are the σm values.

The σ value of Hammett's rule is also disclosed in "Exploring QSAR Hydrophobic, Electronic, and Steric Constants", American Chemical Society, 1995, in addition to C. Harsch, J. Med. Chem., 16, 1207(1973), C. Harsch, J. Med. Chem., 20, 304 (1977), Chem. Rev., 91, 165(1991), C. Hansch, et al.

Here, a case where Z2 is an electron-attractive group means that a part linked to one benzene ring substituted by X is an electron-attractive group.

In General Formula (II-1), the σ value of Hammett's rule, particularly, the σp value of at least any one selected from $Z^2$ and $R^1$ is preferably equal to or greater than 0.20.

Specific examples of the electron-attractive group include a carbamoyl group in which at least one of an acyl group, an alkoxycarbonyl group, an aryloxycarbonyl group, and a hydrogen atom is substituted with a group independently selected from an alkyl group, a cycloalkyl group, and an aryl group (for example, —CONHCH$_3$ (σp: 0.36, σm: 0.35)), a thiocarbamoyl group in which at least one of a thioacyl group, an alkoxythiocarbonyl group, an aryloxythiocarbonyl group, and a hydrogen atom is substituted with a group independently selected from an alkyl group, a cycloalkyl group, and an aryl group (for example, —CSNHCH$_3$ (σp: 0.34, σm: 0.30)), a sulfamoyl group in which at least a hydrogen atom is alkyl or aryl (for example, —SO$_2$N(CH$_3$)$_2$ (σp: 0.65, σm: 0.51)), a sulfonyl group of alkyl or aryl (for example, —SO$_2$CH$_3$ (σp: 0.72, σm: 0.70)), a sulfinyl group of alkyl or aryl (for example, —SOCH$_3$ (σp: 0.49, σm: 0.52)), a cyano group, a nitro group, or a phosphono group.

These electron-attractive groups are preferably a carbamoyl group or a sulfurmoyl group of alkyl or aryl in which at least one of an acyl group, an alkoxycarbonyl group, an aryloxycarbonyl group, a sulfonyl group of alkyl or aryl, a cyano group, a nitro group, and a hydrogen atom is substituted with a group independently selected from alkyl group, a cycloalkyl group, and an aryl group.

Among the compounds represented by General formulae (II-1) to (II-5), compounds represented by General formulae (II-1) and (II-3) or (II-5) are preferable, and a compound represented by General formula (II-1) or (II-3) is more preferable.

Hereinafter, preferable basic skeleton and X part (the following X$^1$ to X$^4$ parts of basic skeleton) will be described. In the invention, all of these combinations is preferable.

Basic Skeleton

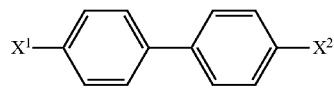
(1)

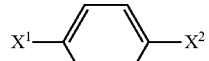
(2)

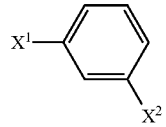
(3)

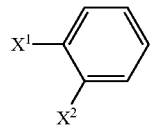
(4)

(5)

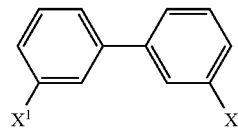
(6)

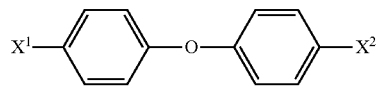
(7)

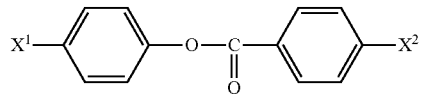
(8)

(9)

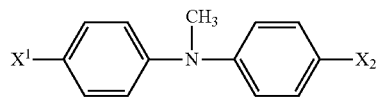
(10)

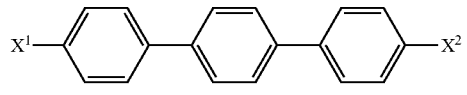
(11)

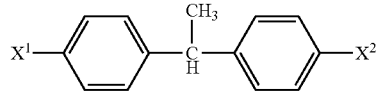
(12)

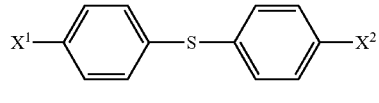
(13)

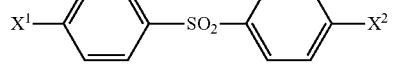
(14)

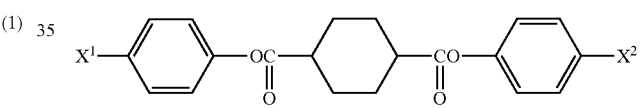
(15)

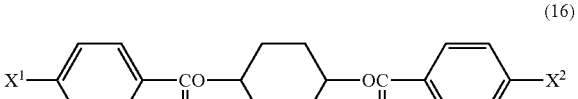
(16)

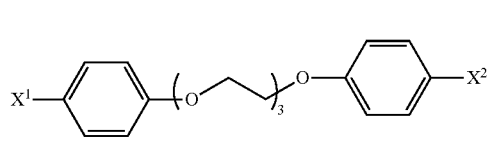
(17)

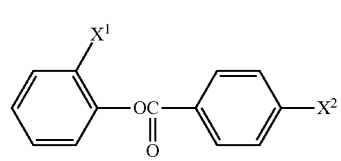
(18)

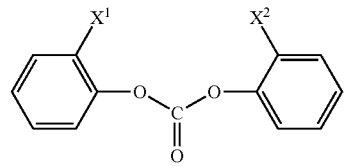
(19)

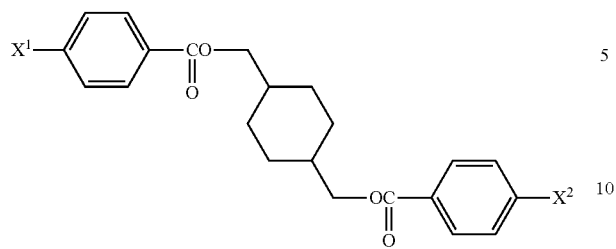
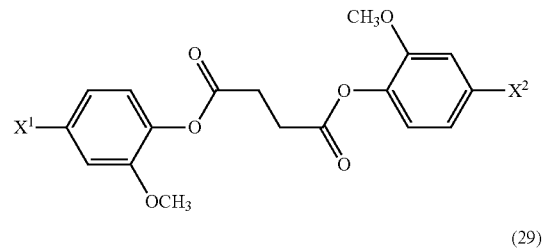
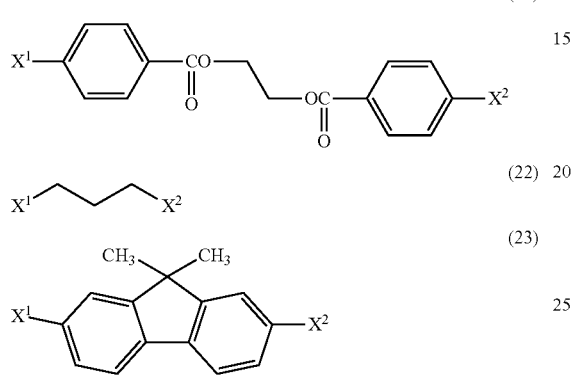
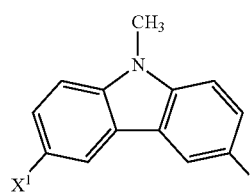
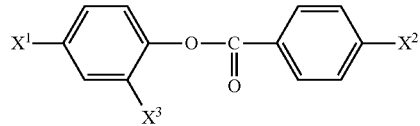
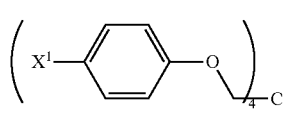
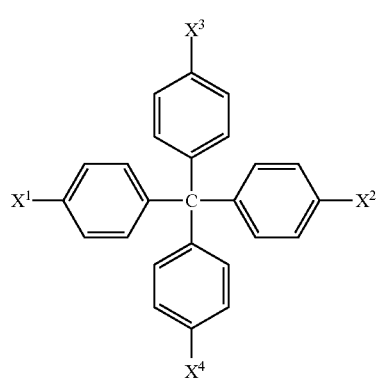
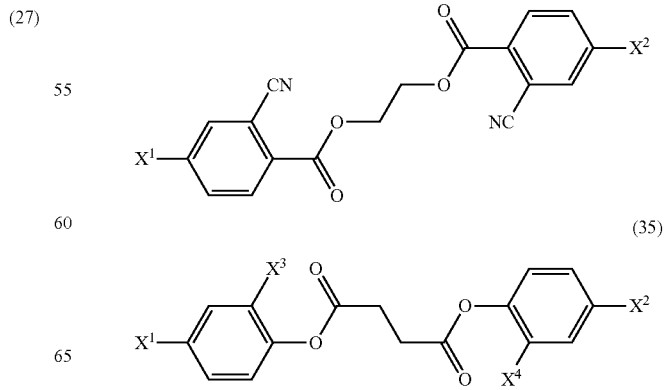

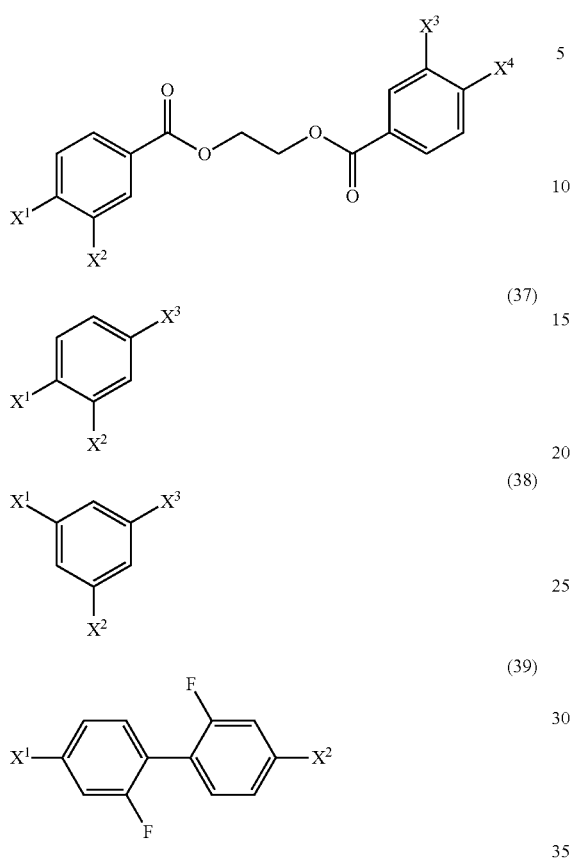
(36)
(37)
(38)
(39)
X part ($X^1$ to $X^4$ parts of the basic skeleton described above)
(1) Formyl group (—CHO) or boronic acid group [—B(OH)$_2$]
(2) Acetal group represented by General Formula (I-C)
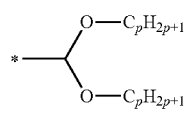 (Xc-101-p)
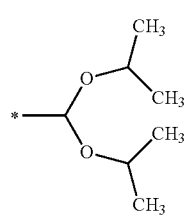 (Xc-102)
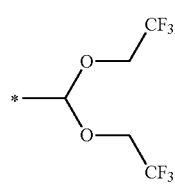 (Xc-103)
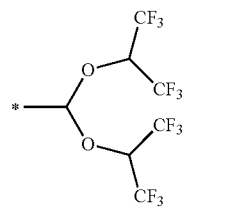 (Xc-104)
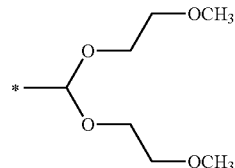 (Xc-105)
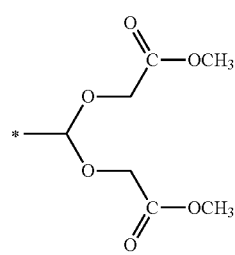 (Xc-106)
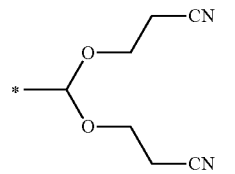 (Xc-107)
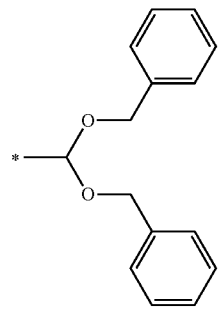 (Xc-108)
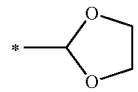 (Xc-201)
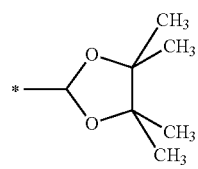 (Xc-202)
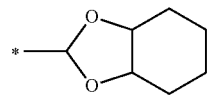 (Xc-203)

(Xc-204) 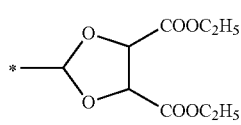
(Xc-205) 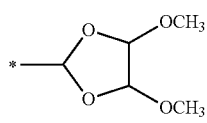
(Xc-206) 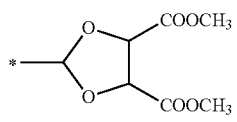
(Xc-301) 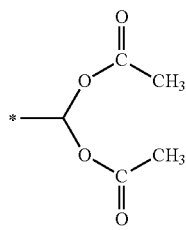
(Xc-302) 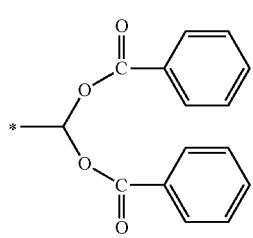
(Xc-401) 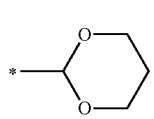
(Xc-402) 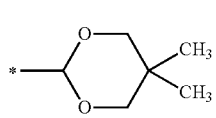
(Xc-403) 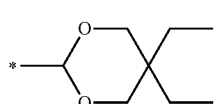
(Xc-404) 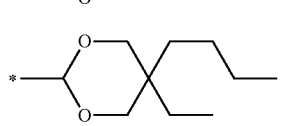
(Xc-405) 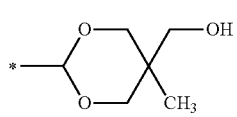
(Xc-406) 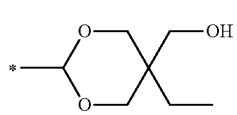
(Xc-407) 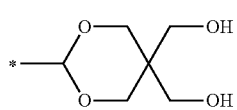
(Xc-408) 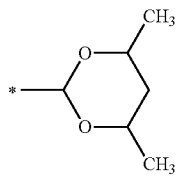
(Xc-409) 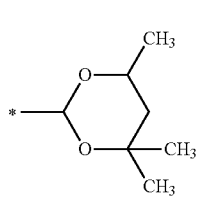
(3) boronic ester group represented by General Formula (I-B)
(Xb-101-p) 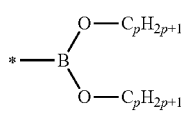
(Xb-102) 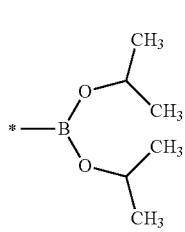
(Xb-103) 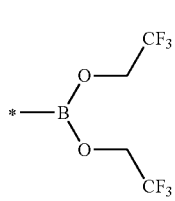
(Xb-104) 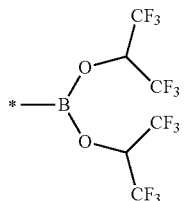
(Xb-105) 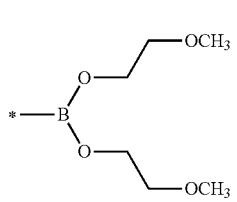
(Xb-201) 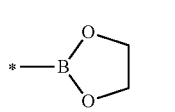

(Xb-202) 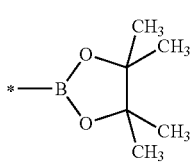

(Xb-203) 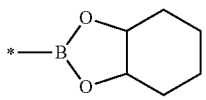

(Xb-204) 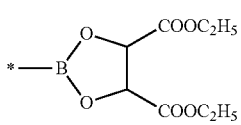

(Xb-401) 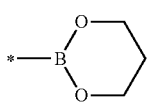

(Xb-402) 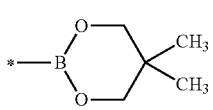

(Xb-403) 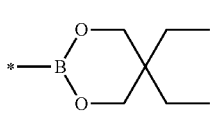

(Xb-404) 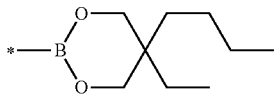

(Xb-405) 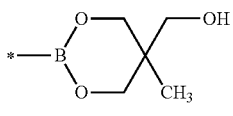

(Xb-406) 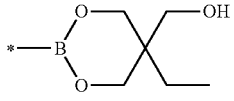

(Xb-407) 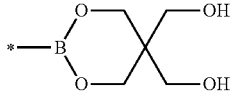

(Xb-408) 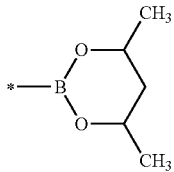

(Xb-409) 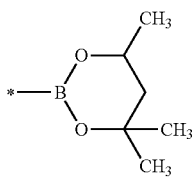

In chemical formulae of (2) and (3), * represents a bond to be bonded to the basic structure.

In addition, p of (Xc-101-p) and (Xb-101-p) represents an integer of 1 to 20 and means n in the formulae. For example, (Xc-101-1) is —CH(OCH$_3$)$_2$ and (Xb-101-1) is —B(OCH$_3$)$_2$.

Hereinafter, specific examples of the compound represented by General Formula (I) used in the invention will be described, but the invention is not limited thereto.

(D-1-1) OHC—⟨ ⟩—⟨ ⟩—CHO (D-1-2) OHC—⟨ ⟩—O—C(=O)—⟨ ⟩—CHO (D-1-3) OHC—⟨ ⟩—O—⟨ ⟩—CHO (D-1-4) (OHC—⟨ ⟩—O—CH$_2$)$_4$C (D-1-5) OHC—⟨ ⟩—CHO (D-1-6) OHC—⟨ ⟩—⟨ ⟩—⟨ ⟩—CHO (D-1-7) OHC—⟨ ⟩—⟨cyclohexyl⟩—⟨ ⟩—CHO (D-1-8) OHC—⟨ ⟩—N(CH$_3$)—⟨ ⟩—CHO (D-1-9) C(—⟨ ⟩—CHO)$_4$ (D-1-10) OHC—⟨ ⟩—CH(CH$_3$)—⟨ ⟩—CHO (D-1-11) OHC—⟨ ⟩—S—⟨ ⟩—CHO -continued
(D-1-12) 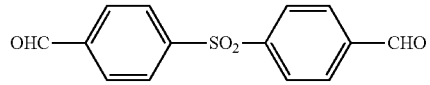
(D-1-13) 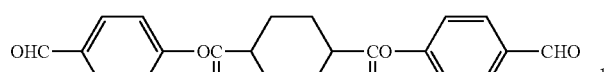
(D-1-14) 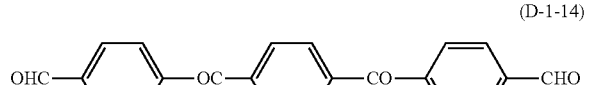
(D-1-15) 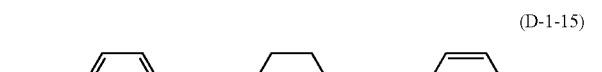
(D-1-16) 
(D-1-17) 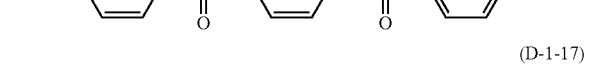
(D-1-18) 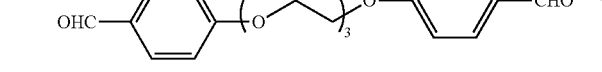
(D-1-19) 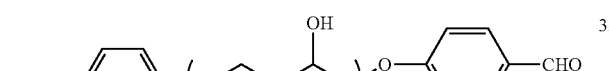
(D-1-20) 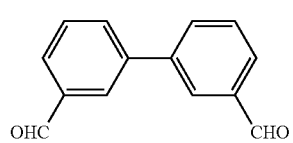
(D-1-21) 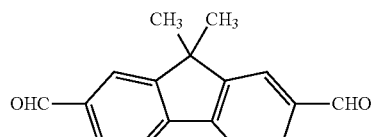
(D-1-22) 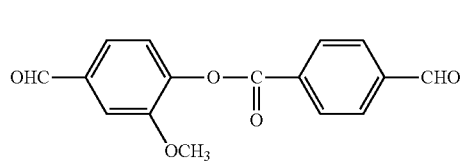
-continued
(D-1-23) 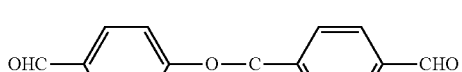
(D-1-24) 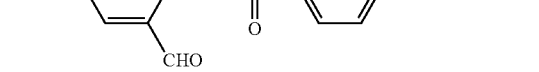
(D-1-25) 
(D-1-26) 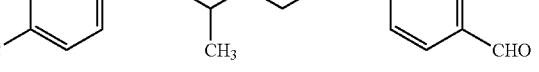
(D-1-27) 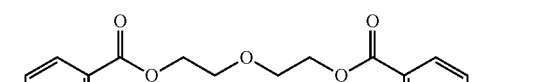
(D-1-28) 
(D-1-29) 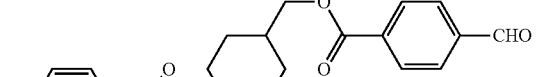
(D-1-30) 

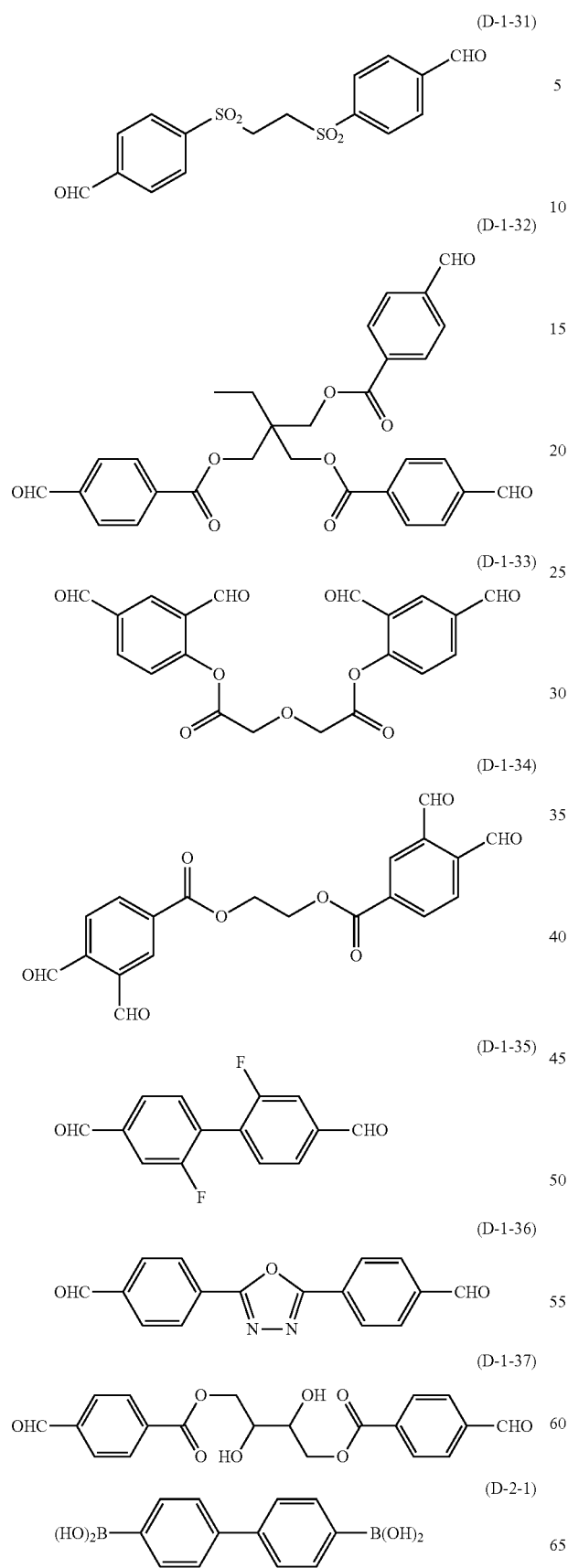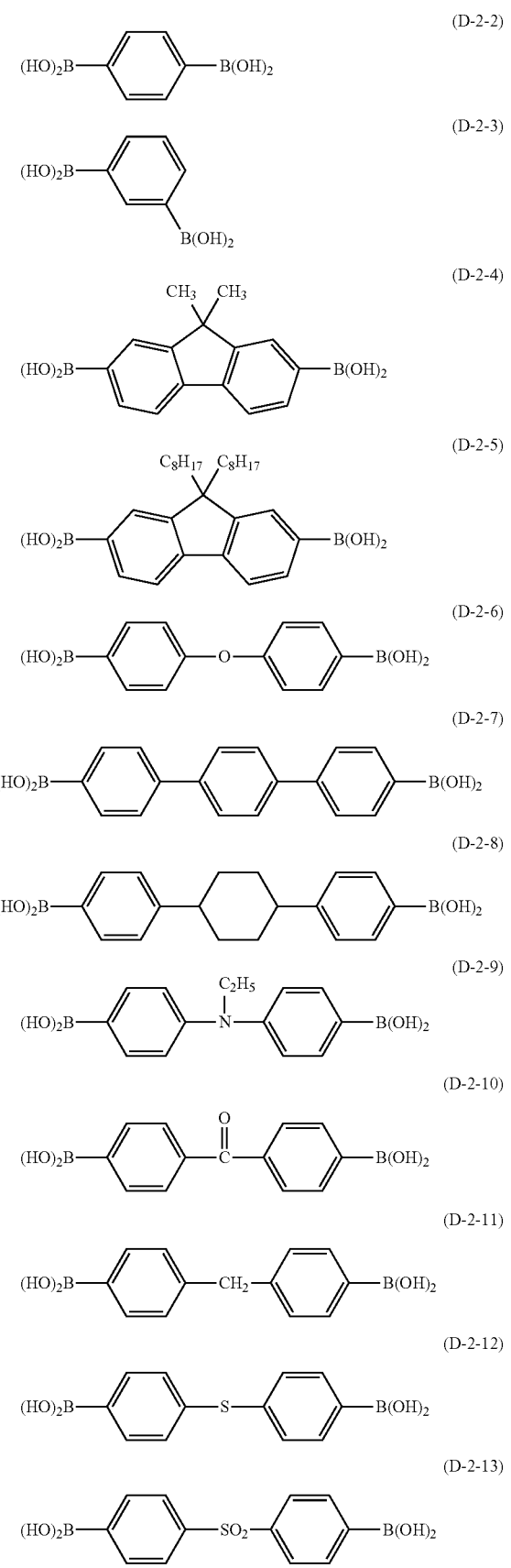

The compound represented by General Formula (I) of the invention may be commercially available or may be synthesized by an arbitrary method. For example, the compound including a formyl group can be easily synthesized by using a formyl compound including a substituent as a raw material and performing a general synthesis reaction such as esterification, amidation, or alkylation. In addition, the compound including a formyl group can be synthesized by oxidizing corresponding alcohol by using a general oxidant such as manganese dioxide. The compound including a boronic acid group can be easily synthesized by using a boronic acid compound including a substituent as a raw material and performing a general synthesis reaction such as esterification, amidation, or alkylation. In addition, in a case of not using the commercially available boronic acid group, the boronic acid group can be synthesized by n-butyllithium and trialkoxyborane (for example, trimethoxyborane or the like) of a halide (for example, aryl bromide or the like).

The blending amount of the compound represented by General Formula (I) of the invention with respect to 100 parts by mass of the resin configuring the polarizing plate protective film is preferably in a range of 0.1 to 30 parts by mass, more preferably in a range of 1 to 25 parts by mass, and even more preferably in a range of 2 to 20 parts by mass.

Here, the substituents S will be described. The substituent S includes the following substituents.

[Substituent S]

Examples of the substituent S include an alkyl group (preferably having 1 to 20 carbon atoms, for example, methyl, ethyl, isopropyl, tert-butyl, pentyl, heptyl, 1-ethylpentyl, 2-ethylhexyl, benzyl, 2-ethoxyethyl, or 1-carboxymethyl), an alkenyl group (preferably having 2 to 20 carbon atoms, for example, vinyl, allyl, or oleyl), an alkynyl group (preferably having 2 to 20 carbon atoms, for example, ethynyl, 2-propynyl, 2-butynyl, or phenylethynyl), a cycloalkyl group (preferably having 3 to 20 carbon atoms, for example, cyclopropyl, cyclopentyl, cyclohexyl, or 4-methylcyclohexyl), an aryl group (preferably having 6 to 20 carbon atoms, for example, phenyl, 1-naphthyl, 4-methoxyphenyl, 2-chlorophenyl, or 3-methylphenyl), a heterocylic group (preferably a heterocyclic group having 0 to 20 carbon atoms, a ring-constituting hetero atom is preferably an oxygen atom, a nitrogen atom, or a sulfur atom, may be formed as a ring with a benzene ring or heterocycle with a 5-membered ring or 6-membered ring, this ring may be a saturated ring, an unsaturated ring, or an aromatic ring, for example, 2-pyridyl, 4-pyridyl, 2-imidazolyl, 2-benzimidazolyl, 2-thiazolyl, or 2-oxazolyl), an alkoxy group (preferably having 1 to 20 carbon atoms, for example, methoxy, ethoxy, isopropyloxy, or benzyloxy), an aryloxy group (preferably having 6 to 20 carbon atoms, for example, phenoxy, 1-naphthyloxy, 3-methylphenoxy, or 4-methoxyphenoxy), an alkylthio group (preferably having 1 to 20 carbon atoms, for example, methylthio, ethylthio, isopropylthio, or benzylthio), an arylthio group (preferably having 6 to 20 carbon atoms, for example, phenylthio, 1-naphthylthio, 3-methylphenylthio, or 4-methoxyphenylthio), a formyl group, an acyl group (including an alkylcarbonyl group, an alkenylcarbonyl group, an arylcarbonyl group, and a heterocyclic carbonyl group, the number of carbon atoms is preferably equal to or smaller than 20, for example, acetyl, pivaloyl, acryloyl, methacryloyl, benzoyl, or nicotinoyl), an alkoxycarbonyl group (preferably having 2 to 20 carbon atoms, for example, ethoxycarbonyl or 2-ethylhexyloxycarbonyl), an aryloxycarbonyl group (preferably having 7 to 20 carbon atoms, for example, phenyloxycarbonyl or naphthyloxycarbonyl), an amino group (including an amino group, an alkylamino group, an arylamino group, and a heterocyclic amino group, preferably having 0 to 20 carbon atoms, for example, amino, N,N-dimethylamino, N,N-diethylamino, N-ethylamino, anilino, 1-pyrrolidinyl, piperidino, or morphonyl), a sulfonamide group of alkyl or aryl (preferably having 0 to 20 carbon atoms, for example, N,N-dimethyl sulfonamide, or N-phenyl sulfonamide), a sulfamoyl group (preferably having 0 to 20 carbon atoms, for example, $SO_2NH_2$ or a sulfamoyl group of alkyl or aryl is preferable, for example, N,N-dimethylsulfamoyl, or N-phenylsulfamoyl), an acyloxy group (preferably having 1 to 20 carbon atoms, for example, acetyloxy or benzoyloxy), a carbamoyl group [preferably having 1 to 20 carbon atoms, for example, —C(=O)NH$_2$ or a carbamoyl group of alkyl or aryl is preferable, for example, N,N-dimethylcarbamoyl or N-phenylcarbamoyl], an acylamino group (preferably having 1 to 20 carbon atoms, for example, acetylamino, acryloylamino, benzoylamino, or nicotinamide), a thioacyl group, an alkoxythiocarbonyl group, an aryloxythiocarbonyl group, a thiocarbamoyl group [as the preferred range and specific examples thereof, an element in which the C(=O) part of the corresponding acyl group, alkoxycarbonyl group, an aryloxycarbonyl group, or a carbamoyl group is substituted with (C=S) is used], a silyl group (preferably having 3 to 20 carbon atoms, a silyl group in which alkoxy or aryloxy is substituted is more preferable, a trialkoxysilyl group is even more preferable, for example, trimethoxysilyl or triethoxysilyl), a trialkoxysilyl group, a halogen atom (for example, a fluorine atom, a chlorine atom, a bromine atom, or an iodine atom), an acylsulfamoyl group (including an alkylcarbonylsulfamoyl group, an alkenylcarbonylsulfamoyl group, an arylcarbonylsulfamoyl group, and a heterocyclic carbonylsulfamoyl group, the number of carbon atoms is preferably equal to or smaller than 20, for example, acetylsulfamoyl, pivaloylsulfamoyl, acryloylsulfamoyl, methacrolylsulfamoyl, benzoylsulfamoyl, or nicotinoylsulfamoyl), a sulfonylsulfamoyl group of alkyl or aryl (preferably having 1 to 20 carbon atoms, for example, methylsulfonylsulfamoyl, ethylsulfonylsulfamoyl, phenylsulfonylsulfamoyl, or tolylsulfonylsulfamoyl), a cyano group, a nitro group, a hydroxy group or an anion thereof, mercapto group or an anion therof, a sulfo group or salt thereof, a carboxyl group or salt thereof, a phosphate group or salt therof, a boronic acid group or salt thereof, a boronic acid ester group, and an onio group (for example, a sulfonio group of sulfonium salt, an ammonio of ammonium salt, an iodonio group of iodonium salt, or phosphonio group of phosphonium salt).

These substituents may be further substituted with a substituent examples of such a substituent include groups selected from the substituent S described above.

Examples thereof include an aralkyl group in which an alkyl group is substituted with an aryl group (for example, benzyl, phenethyl, or diphenylmethyl), a group in which an alkyl group is substituted with an alkoxycarbonyl group or a cyano group (for example, benzoylmethyl), perfluoroalkyl group such as trifluoromethyl in which an alkyl group is substituted with a fluorine atom, and a substituted aryl group in which an aryl group is substituted with the substituent S described above. In addition, a group having an active methine or active methylene structure (an alkyl group substituted with an electron-attractive group, a group having a part in which methine or methylene is bonded to an electron-attractive group, or a group having a methine or methylene part interposed between the electron-attractive group) is also preferably used.

<Resin>

The polarizing plate protective film of the invention includes a resin and preferably has a film shape.

An arbitrary resin can be used as the resin used in the polarizing plate protective film, and there is no limitation within a range not departing the gist of the invention. Examples of the resin include a cellulose acylate resin, acrylic resin, and cycloolefin resin. Among these resins, an acrylic resin and a cellulose acylate resin are preferable, and from a viewpoint of excellent compatibility with the compound represented by General Formula (I), a cellulose acylate resin is more preferable.

These resins may be used alone or in combination of two or more kinds thereof, and in a case of using two or more kinds thereof in combination, a component having the greatest amount among the resin components is set as a main component.

(Cellulose Acylate)

In the invention, cellulose acylate to be a main component of a cellulose acylate film may be used alone or in combination of two or more kinds thereof. For example, as cellulose acylate, cellulose acetate formed of only an acetyl group as an acyl substituent, cellulose acylate including a plurality of different acyl substitutes, or a mixture of different cellulose acylates may be used. In addition, the main component means that the content of cellulose acylate is equal to or greater than 50 mass % in the resin component configuring a film or a layer, and the content of cellulose acylate in the resin component is preferably equal to or greater than 60 mass % and more preferably equal to or greater than 80 mass %.

As cellulose which is a raw material of cellulose acylate used in the invention, cotton linters or wood pulp (hardwood pulp or softwood pulp) is used. Cellulose obtained from any raw material cellulose can be used and those may be mixed according to circumstances. As the raw material cellulose, cellulose disclosed in "Lectures on Plastic Materials (17) Cellulose Resins" written by Marusawa and Uda, published by Nikkan Kogyo Shimbun, Ltd. in 1970, Japan Institute of Invention and Innovation's Disclosure Bulletin 2001-1745 (pp. 7-8) can be used.

In the invention, an acyl group of cellulose acylate may be used alone or two or more kinds of an acyl group may be used. The cellulose acylate used in the invention preferably includes an acyl group having two or more carbon atoms as a substituent. The acyl group having two or more carbon atoms may be an aliphatic acyl group or an aromatic acyl group, and there is no particular limitation. These are, for example, an alkylcarbonyl group, an alkenylcarbonyl group or an aromatic carbonyl group, and an aromatic alkylcarbonyl group of cellulose, and may respectively include a substituted group. Preferred examples thereof include acetyl, propionyl, butanoyl, heptanoyl, hexanoyl, octanoyl, decanoyl, dodecanoyl, tridecanoyl, tetradecanoyl, hexadecanoyl, octadecanoyl, isobutanoyl, tert-butanoyl, cyclohexanecarbonyl, oleoyl, benzoyl, naphthylcarbonyl, and cinnamoyl. Among these, acetyl, propionyl, butanoyl, dodecanoyl, octadecanoyl, tert-butanoyl, oleoyl, benzoyl, naphthylcarbonyl, and cinnamoyl are more preferable, and acetyl, propionyl, and butanoyl are even more preferable.

The cellulose acylate used in the invention preferably includes an acyl group having 2 to 4 carbon atoms as a substituent. When using two or more kinds of the acyl group, it is preferable that one kind thereof is an acetyl group, and an acyl group having 2 to 4 carbon atoms used in addition is preferably a propionyl group or a butanoyl group. By using these cellulose acylate, it is possible to prepare a solution having preferred solubility, and particularly, in a non-chlorine organic solvent, an excellent solution can be prepared. In addition, it is possible to prepare a solution having low viscosity and excellent filterability.

In the invention, it is particularly preferable that only an acetyl group is used as the acyl group of cellulose acylate.

Hereinafter, the cellulose acylate preferably used in the invention will be described in detail.

A glucose unit bonded to β-1,4 configuring cellulose has free hydroxyl groups at second, third, and sixth positions. The cellulose acylate is a polymer obtained by acylating parts or all of these hydroxyl groups with acyl groups.

An acyl substitution degree is a degree of the acylation of the hydroxyl groups in cellulose located at the second, third, and sixth positions, and in a case where the hydroxyl groups at the second, third, and sixth positions of all the glucose units are all acylated, the total acyl substitution degree is 3. For example, in a case in which only the sixth positions of all the glucose units are all acylated, the total acyl substitution degree is 1. In the same manner as described above, even in a case where any one of the sixth and second positions of the respective glucose units are all acylated in all the hydroxyl groups in all glucose, the total acyl substitution degree is 1.

That is, an acyl substitution degree indicates a degree of acylation by setting a case where all the hydroxyl groups in a glucose molecule are all acylated, as 3.

Regarding the details of a method for measuring the acyl substitution degree, the acyl substitution degree can be measured according to a method disclosed in Tetsuka et. al., Carbohydrate. Res., 273, 83-91 (1995) or a method based on ASTM-D817-96.

When the total acyl substitution degree of the cellulose acylate used in the invention is set as A, A is preferably 1.5 to 3.0 ($1.5 \leq A \leq 3.0$), and in the invention, a range of 2.80 to 2.97 is preferable from viewpoints of compatibility with the compound represented by General Formula (I) of the invention and a decrease of haze.

In addition, in the cellulose acetate in which only an acetyl group is used as the acyl group of the cellulose acylate, when the total acetyl substitution degree is set as B, B is preferably 2.0 to 3 ($2.0 \leq B \leq 3.0$), and in the invention, a range of 2.80 to 2.97 is preferable from viewpoints of compatibility with the compound represented by General Formula (I) of the invention and a decrease of haze.

In a case where the polarizing plate protective film of the invention is a laminate (multilayer configuration), in the cellulose acylate film, the degrees of acyl substitution of the cellulose acylate in the respective layers may be uniform, or a plurality of cellulose acylates having different degrees of acyl substitution or different acyl groups may be present in a single layer in a mixed form.

In the acylation of cellulose, in a case where an acid anhydride or an acid chloride is used as an acylating agent, methylene chloride or an organic acid, for example, acetic acid is used as an organic solvent which is a reaction solvent.

As a catalyst, in a case where the acylating agent is an acid anhydride, a protonic catalyst such as sulfuric acid is preferably used and, in a case where the acylating agent is an acid chloride (for example, $CH_3CH_2COCl$), a basic compound is used.

The industrial synthesis method of a mixed aliphatic acid ester of the most ordinary cellulose is a method of acylating cellulose with an aliphatic acid (acetic acid, propionic acid, valeric acid, or the like), which corresponds to the acetyl group and other acyl groups, or a mixed organic acid component containing an acid anhydride thereof.

The cellulose acylate can be synthesized using a method disclosed in, for example, JP1998-45804A (JP-H10-45804A).

In the polarizing plate protective film of the invention, particularly, in the cellulose acylate film used in the invention, the content of the cellulose acylate in the total solid content is preferably 5 to 99 mass % from a viewpoint of water vapor permeability, and more preferably 20 to 99 mass %, and particularly preferably 50 to 95 mass %.

<Additives>

In the polarizing plate protective film of the invention, in addition to the compound represented by General Formula (I), it is also possible to add additives such as a retardation adjuster (a retardation-developing agent and a retardation-reducing agent), a plasticizer of a polycondensed ester compound (polymer), a polyvalent ester of a polyhydric alcohol, phthalate ester, phosphate ester, or sugar ester, furthermore, an ultraviolet absorber, an antioxidant, and a matting agent particularly in the cellulose acylate film.

In the specification, regarding the expression of a compound group, there are cases in which the expression of a compound includes "-based", for example, such as a phosphate ester-based compound, however, in the above-described case, this compound refers to the same phosphate ester compound.

A retardation-reducing agent, a retardation-developing agent, a plasticizer, polyhydric alcohol ester-based hydrophobizing agent or a polycondensed ester-based hydrophobizing agent, a carbohydrate compound derivative-based plasticizer, an antioxidant, an ultraviolet absorber, and a matting agent are preferably compounds or materials disclosed in paragraphs 0061 to 0126 of JP2013-28782A, and the entire content including the amounts thereof is preferably incorporated as a part of this specification.

(Radical Scavenger)

It is preferable that the polarizing plate protective film preferably includes a radial scavenger. As the radical scavenger, HALS or reductone is preferably used.

As HALS, particularly, a compound including a 2,2,6,6-tetramethyl-piperidine ring is preferable, and a first position of piperidine is preferably a hydrogen atom, an alkyl group, an alkoxy group, a hydroxyl group, an oxy radical group (—O—), an acyloxy group, or an acyl group, and a fourth position is more preferably a hydrogen atom, a hydroxyl group, an acyloxy group, an amino group which may have a substituent, an alkoxy group, or an aryloxy group. It is preferable that 2 to 5 2,2,6,6-tetramethyl-piperidine rings are included in a molecule.

Examples of the compound include Sunlizer HA-622 (product name. Sort Co., Ltd.), CHIMASSORB 2020FDL, TINUVIN 770DF, TINUVIN 152, TINUVIN 123, FLAMESTAB NOR 116 FF [product name, all manufactured by BASF (Ciba Specialty Chemicals Inc.)], CYASORB UV-3346, CYASORB UV-3529 (product name, all manufactured by Sun Chemical Company Ltd.).

Examples of reductone include compounds disclosed in example of paragraphs 0014 to 0034 of JP1994-27599A (JP-H06-27599A), compounds disclosed in example of paragraphs 0012 to 0020 of JP6-110163A, and compounds disclosed in example of paragraphs 0022 to 0031 of JP1996-114899A (JP-H08-114899A).

An emulsion derivative of ascorbic acid or erythorbic acid can be used, and examples thereof include L-ascorbyl stearate, L-ascorbyl tetraisopalmitate, L-ascorbyl palmitate, erythorbic acid palmitate, and erythorbic acid tetraisopalmitate. Among these, a component including an ascorbic acid skeleton is preferable, and myristate, palmitate, and stearate of L-ascorbic acid are particularly preferable.

The content of the radical scavenger in the polarizing plate protective film is 0.001 to 2.0 parts by mass and more preferably 0.01 to 1.0 parts by mass with respect to 100 parts by mass of the resin configuring the polarizing plate protective film.

(Deterioration Inhibitor)

A deterioration inhibitor (for example, an antioxidant, a peroxide decomposer, a radical inhibitor, a metal inactivating agent, an acid scavenger, or amine) may be added to the polarizing plate protective film. In addition, the ultraviolet absorbent is also one of the deterioration inhibitor. These deterioration inhibitors are disclosed in JP1985-235852A (JP-S60-235852A), JP1991-199201A (JP-H03-199201A), JP1993-1907073A (JP-H05-1907073A), JP1993-194789A (JP-H05-194789A), JP1993-271471A (JP-H05-271471A), JP1994-107854A (JP-H06-107854A), JP11994-118233A (JP-H06-118233A), JP1994-148430A (JP-1106-148430), JP1995-11056A (JP-107-11056A), JP1995-11055A (JP-H07-11055A), JP1995-11056A (JP-H07-11056A), JP1996-29619A (JP-H08-29619A), JP1996-239509A (JP-H08-239509A), JP2000-204173A, and JP2006-251746A.

The radical scavenger also exhibits a deterioration preventing operation, and amines are also known as the deterioration inhibitor. Examples thereof include compounds disclosed in paragraphs 0009 to 0080 of JP1993-194789A (JP-H05-194789A), or aliphatic amines such as tri-n-octylamine, triisooctylamine, tris (2-ethylhexyl) amine, and N,N-dimethyldodecylamine.

In addition, it is also preferable to use polyvalent amines including two or more amino group, and polyvalent amine including two or more primary or secondary amino groups is more preferable. Examples of the compound including two or more amino groups include a nitrogen-containing heterocyclic compound (a compound including a pyrazolidine ring or a piperazine ring), and a polyamine-based compound (compound including chain-shaped or cyclic polyamine, for example, diethylenetriamine, tetraethylenepentamine, N,N'-bis(aminoethyl)-1,3-propanediamine, N,N,N',N'',N''-pentakis(2-hydroxypropyl) diethylenetriamine, polyethyleneimine, a modified polyethyleneimine, or cyclam as a basic skeleton).

The content of the deterioration inhibitor in the polarizing plate protective film is preferably 1 ppm to 10%, more preferably 1 ppm to 5.0%, and even more preferably 10 ppm to 1.0% based on mass.

(Peeling Accelerator)

An arbitrary peeling accelerator may be added to the polarizing plate protective film.

The peeling accelerator is preferably organic acid, a polycarboxylic acid derivative, a surfactant, or a chelating agent. For example, compounds disclosed in paragraphs 0048 to 0081 of JP2006-45497A, compounds disclosed in paragraphs 0077 to 0086 of JP2002-322294A, and compounds disclosed in paragraphs 0030 to 0056 of JP2012-72348A, and the like can be preferably used. The content of the peeling accelerator in the polarizing plate protective film is preferably 1 ppm to 5.0% and more preferably 1 ppm to 2.0% based on the mass.

(Matting Agent)

Fine particles are preferably added to the polarizing plate protective film of the invention as a matting agent. Examples of the fine particles used in the invention include silicon dioxide, titanium dioxide, aluminum oxide, zirconium oxide, calcium carbonate, talc, clay, calcined kaolin, calcined calcium silicate, hydrated calcium silicate, aluminum silicate, magnesium silicate, and calcium phosphate. It is preferable that the fine particles include silicon, from a viewpoint of decreasing turbidity, and silicon dioxide is particularly preferable. The fine particles of silicon dioxide has a primary average particle diameter equal to or smaller than 20 nm, and an apparent specific gravity is preferably equal to or greater than 70 g/liter. The apparent specific gravity is more preferably 90 to 200 g/liter and even more preferably 100 to 200 g/liter. It is preferable that the apparent specific gravity is great, because a dispersion having high concentration can be prepared, and haze and aggregates are improved.

(Barbituric Acid-Based Additive)

In the polarizing plate protective film of the invention, it is preferable to use a compound represented by the following General Formula (A). Particularly, the resin configuring the polarizing plate protective film is preferable in a case of the cellulose acylate. The compound represented by the following General Formula (A) can exhibit various functions, and is for example, effective for improving durability of light, heat, wet heat of the polarizing plate or improving hardness of the polarizing plate protective film.

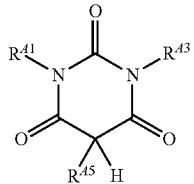

General Formula (A)

In General Formula (A), $R^{41}$ and $R^{43}$ each independently represent a hydrogen atom, an alkyl group, a cycloalkyl group, an alkenyl group, or an aromatic group. Here, an alkyl group, a cycloalkyl group, an alkenyl group, or an aromatic group may include a substituent. $R^{45}$ represents a hydrogen atom or a substituent.

The compound represented by General Formula (A) includes a tautomer having a structure in which a hydrogen atom in a ring structure is enolized with carbonyl in the adjacent ring structure or is imide-oxidized in a case where $R^{41}$ and $R^{43}$ are hydrogen atoms, or salt thereof.

The number of carbon atoms of the alkyl group of $R^{41}$, $R^{43}$, and $R^{45}$ is preferably 1 to 20, more preferably 1 to 10, even more preferably 1 to 5, and particularly preferably 1 to 3, and a methyl group or an ethyl group is preferable. However, in a case where a group including a ring structure is a substituted alkyl group, the number of carbon atoms is preferably 7 to 20, more preferably 7 to 12, and even more preferably 7 to 10. The ring structure of the alkyl group having a ring structure may include an aromatic ring (including aromatic heterocycle) or an aliphatic ring, and an aromatic hydrocarbon ring or an aliphatic ring is preferable. Specific examples of the alkyl group having a ring structure include a benzyl group and phenethyl group, and a benzyl group is particularly preferable.

The number of carbon atoms of the cycloalkyl group of $R^{41}$ and $R^{43}$ is preferably 3 to 20, more preferably 3 to 10, even more preferably 4 to 8, and particularly preferably 5 or 6. Specific examples of the cycloalkyl group include cyclopropyl, cyclopentyl, and cyclohexyl, and cyclohexyl is particularly preferable.

The number of carbon atoms of the alkenyl group of $R^{41}$ and $R^{43}$ is preferably 2 to 20, more preferably 2 to 10, and even more preferably 2 to 5. Examples thereof include vinyl and allyl.

The aromatic group of $R^{41}$ and $R^{43}$ may be an aromatic hydrocarbon group or an aromatic heterocyclic group, and an aromatic hydrocarbon group is preferable.

The number of carbon atoms of the aromatic hydrocarbon group is preferably 6 to 20, more preferably 6 to 16, and even more preferably 6 to 12. As the aromatic hydrocarbon group, phenyl and naphthyl are preferable and phenyl is more preferable.

As the aromatic heterocyclic group, a 5-membered ring or 6-membered ring is preferable, a benzene ring or a heterocycle may be formed. As the hetero atom configuring a heterocyclic ring of the aromatic heterocyclic group, a nitrogen atom, an oxygen atom, and a sulfur atom are preferable, and the number of carbon atoms is preferably 0 to 20, more preferably 1 to 16, and even more preferably 3 to 12. Examples of such a heterocycle include a pyrrole ring, a thiophene ring, a furan ring, a pyrazole ring, an oxazole ring, a thiazole ring, a pyridine ring, and an indole ring.

As the substituent of $R^{45}$, the substituent S is used, and examples thereof include an alkyl group, a cycloalkyl group, an alkenyl group, an aromatic group, a halogen atom, a formyl group, an acyl group, a cyano group, and a water-soluble group.

Here, the water-soluble group is a group which increases solubility of the compound to water, and an anionic or cationic group or a group which can be decomposed to become an anionic group (for example, pKa is preferably equal to or smaller than 10).

Examples of such a group include a sulfo group or a salt thereof, a carboxyl group or a salt thereof, a phosphoric acid group or a salt thereof, a hydroxyl group, a mercapto group, an amino group, an onio group (preferably, an ammonio group), a sulfonamide group, an acyl sulfamoyl group, an alkyl or aryl sulfonylsulfamoyl group, and a group having an active methine or methylene structure.

Among these, a sulfo group or a salt thereof, a carboxyl group or a salt thereof, a hydroxy group, and an amino group are preferable.

The states of including salt regarding a hydroxyl group, a mercapto group, an amino group, a sulfonamide group, an acyl sulfamoyl group, an alkyl or aryl sulfonylsulfamoyl group, and a group having an active methine or methylene structure are also included.

In addition to a salt of sulfo group or a carboxyl group, a counter ion configuring a hydroxyl group, a mercapto group, an amino group or a salt, a sulfonamide group, an acyl sulfamoyl group, an alkyl or aryl sulfonylsulfamoyl group, and a slat of a group having an active methine or methylene structure may be an inorganic ion or an organic ion.

As the inorganic ion, ammonium ion and alkali metal ion (for example, lithium ion, sodium ion, and potassium ion) are preferable, and as the organic ion, an organic cationic onium ion is used, and examples thereof include an organic ammonium ion (for example, a tetramethylammonium ion or a tetramethylguanidinium ion), a cation of a nitrogen-containing heteroaromatic ring (for example, a pyrrolidinium ion or a pyridinium ion), a phosphonium ion (tetramethylphosphonium ion), and a sulfonium ion (for example, trimethylsulfonium ion). Among these counter ions, an alkali metal ion, that is, an alkali metal salt is preferable.

Regarding such a counter ion, also a counter ion in a case where the compound represented by General Formula (A) to form a salt, the same counter ions described above are preferable.

Meanwhile, in a case of a slat of an amino group, acid forming a salt may be inorganic acid or organic acid.

In a case of inorganic acid, hydrochloric acid, bromic acid, sulfuric acid, phosphoric acid, or boric acid is used, and in a case of organic acid, aliphatic or aromatic carboxylic acid or sulfonic acid (for example, formic acid, acetic acid, oxalic acid, benzoic acid, methanesulfonic acid, benzenesulfonic acid, and nicotinic acid) is used.

In addition, in a case of the onio group, an inorganic or organic anion is used, and an anion having the inorganic or organic acid is used.

$R^{45}$ is preferably a hydrogen atom, an alkyl group, a cycloalkyl group, an alkenyl group, an aromatic group, a halogen atom, a formyl group, an acyl group, a cyano group, and a hydroxyl group.

In a case where $R^{41}$, $R^{43}$, and $R^{45}$ are an alkyl group, a cycloalkyl group, an alkenyl group, or an aromatic group, the substituent S is used as a substituent thereof, and an alkyl group, a cycloalkyl group, an alkenyl group, an aromatic group, a heterocyclic group, an alkoxy group, an alkylthio group, an alkylsulfonyl group, a halogen atom, a formyl group, an acyl group, a silyl group, and a water-soluble group, more preferably an alkyl group, a cycloalkyl group, an aryl group, a heterocyclic group, an alkoxy group, an alkylthio group, an alkylsulfonyl group, a halogen atom, a formyl group, an acyl group, a silyl group, and a water-soluble group are more preferable, and an alkyl group, a cycloalkyl group, an aryl group, a heterocyclic group, an alkoxy group, an alkylthio group, an alkylsulfonyl group, a halogen atom, formyl group, acyl group, hydroxyl group, a sulfo group or salt thereof, a carboxyl group or salt thereof, a boronic acid group or salt thereof, a carbamoyl group, a sulfamoyl group, and an onio group (preferably, an ammonio group including a quaternary ammonium group) are even more preferable.

The preferred range of the compound represented by the following General Formula (A) is depending on the use thereof, but is widely divided into the following two types.

A first preferred aspect is a compound of a combination of the following substituents.

$R^{41}$, $R^{43}$, and $R^{45}$ each independently represent a hydrogen atom, an alkyl group, a cycloalkyl group, an alkenyl group, or an aromatic group, and the alkyl group, the cycloalkyl group, the alkenyl group, and the aromatic group may include a substituent, and a preferred substituent is a compound including a substituent other than a water-soluble group, among the substituent S.

The substituent which may be included in each group described above is preferably a hydrogen atom, an alkyl group, a cycloalkyl group, an alkenyl group, an aromatic group, a heterocyclic group, an alkoxy group, an aryloxy group, an alkylthio group, an arylthio group, an acyl group, a silyl group, and a halogen atom.

Any one of $R^{41}$, $R^{43}$, and $R^{45}$ is preferably a group having a ring structure, and the number of ring structures is preferably 1 to 6, more preferably 2 to 6, even more preferably 2 to 5, and particularly preferably 3 to 5.

As such a ring, an aliphatic hydrocarbon ring or an aromatic hydrocarbon ring is preferable, and a cyclopentane ring, a cyclohexane ring, a benzene ring, or a naphthalene ring is more preferable, and a cyclohexane ring or a benzene ring are even more preferable.

In a case where $R^{41}$, $R^{43}$, and $R^{45}$ are cyclic groups, a cycloalkyl group and an aryl group are preferable. In a case where $R^{41}$, $R^{43}$, and $R^{45}$ are groups having a ring structure, a group including a cycloalkyl part or an aryl part is used as the substituent, among the groups exemplified as the substituent S, a group including a cycloalkyl group or an aryl group as a substituent is preferable, and a cycloalkyl-substituted alkyl group or an aralkyl group are particularly preferable, and a benzyl group is most preferable.

As the cyclic group or the group having a ring structure, a cycloalkyl group, an aryl group, and an aralkyl group are more preferable.

The molecular weight of the compound of the first aspect is preferably 250 to 1,200, more preferably 300 to 800, and particularly preferably 350 to 600.

When the combination and the molecular weight of the substituent are set to be in such preferred ranges, it is possible to have a film having excellent control of volatilization of the compound represented by General Formula (A) of the invention from the polarizing plate protective film and having high transparency.

A second preferred aspect is a compound of a combination of the following substituents.

In this aspect, a polar effect is used, and diffusibility is also considered.

$R^{41}$ and $R^{43}$ each independently represent a hydrogen atom, an alkyl group, a cycloalkyl group, an alkenyl group, or an aromatic group, and $R^{45}$ is a hydrogen atom or a substituent. The compound of this aspect is 1) a compound in which any one of $R^{41}$, $R^{43}$, and $R^{45}$ is a water-soluble group or a group including a water-soluble group, 2) a compound in which the molecular weight is equal to or greater than 128 and smaller than 250, and/or 3) a compound in which any one or two of $R^{41}$, $R^{43}$, and $R^{45}$ are hydrogen atoms.

The molecular weight of the compound of the second aspect is preferably 128 to 1,200 and more preferably 150 to 800.

Hereinafter, specific examples of the compound represented by General Formula (A) are shown, but the invention is not limited thereto.

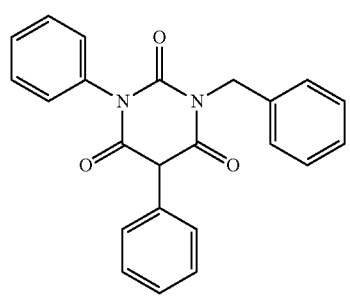

A-1

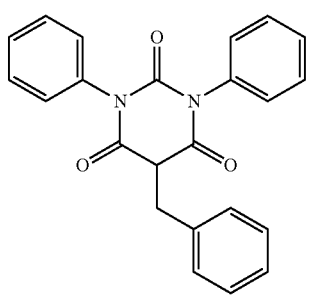

A-2

-continued
| A-3 | A-4 |
|---|---|
| 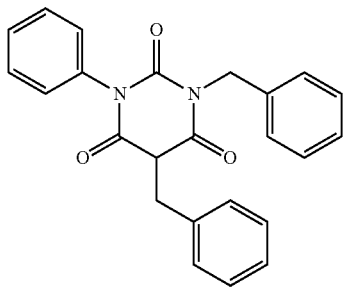 | 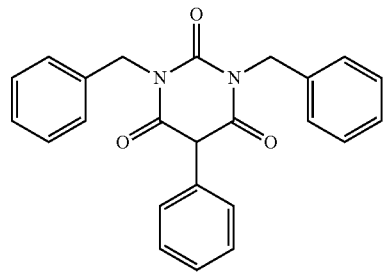 |
| A-5 | A-6 |
|---|---|
| 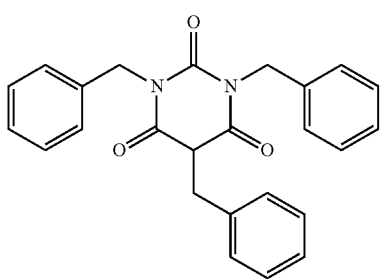 | 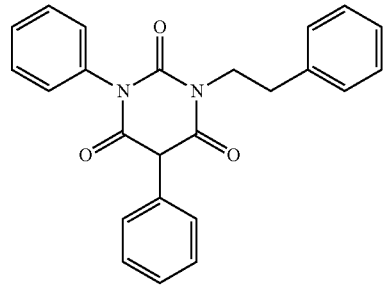 |
| A-7 | A-8 |
|---|---|
| 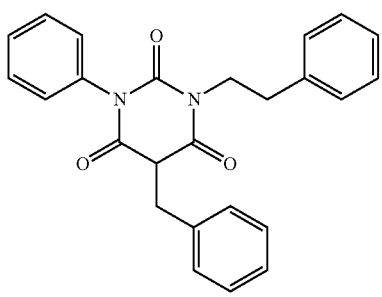 | 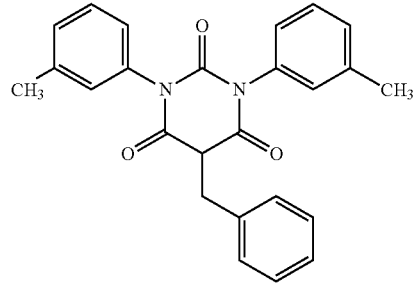 |
| A-9 | A-10 |
|---|---|
| 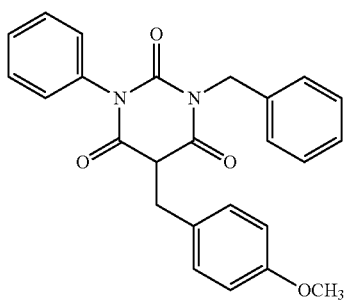 | 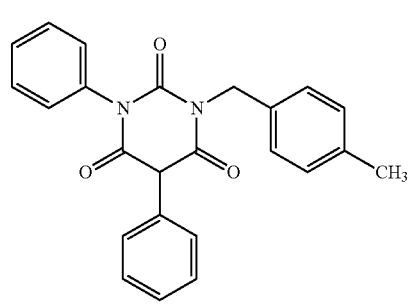 |
| A-11 | A-12 |
|---|---|
| 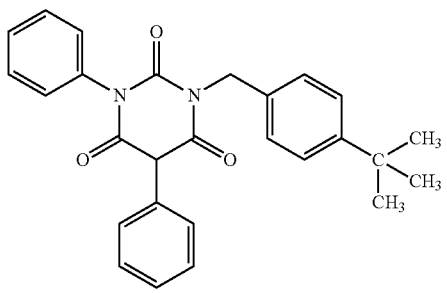 | 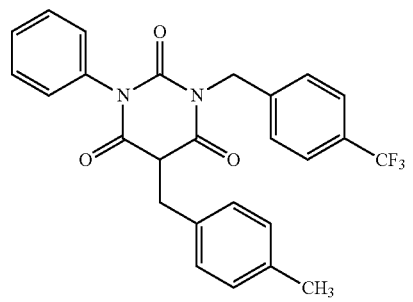 |

-continued
A-13
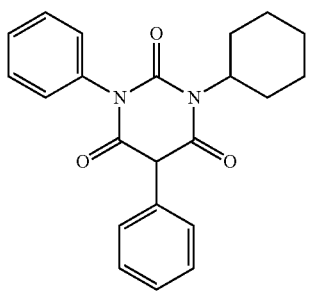
A-14
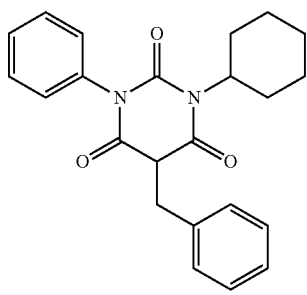
A-15
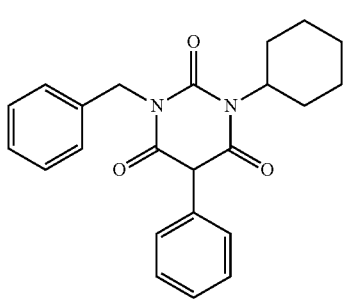
A-16
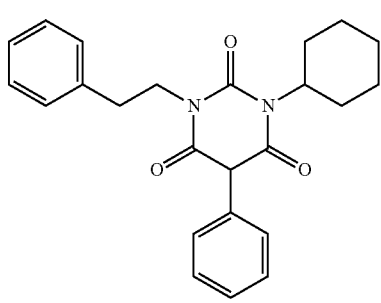
A-17
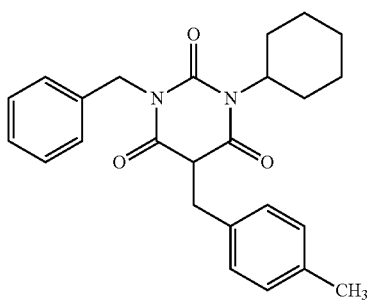
A-18
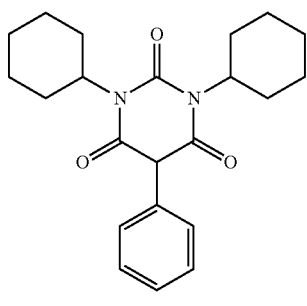
A-19
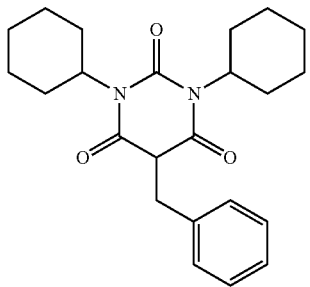
A-20
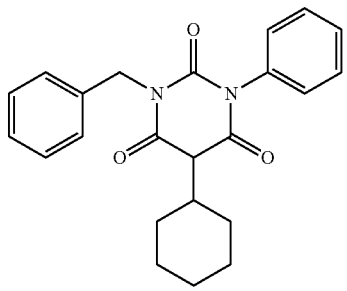
A-21
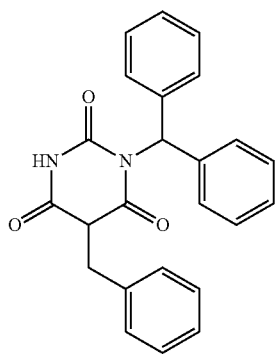
A-22
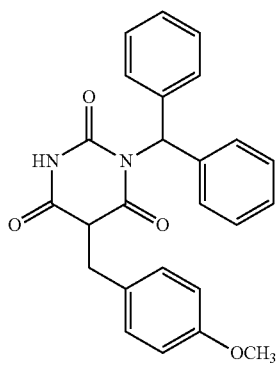

-continued
A-23
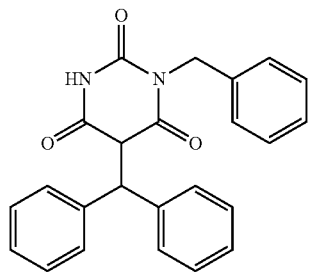
A-24
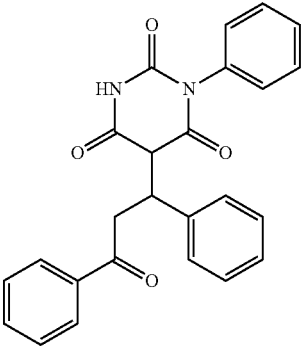
A-25
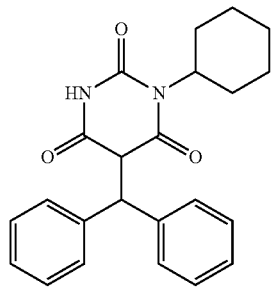
A-26
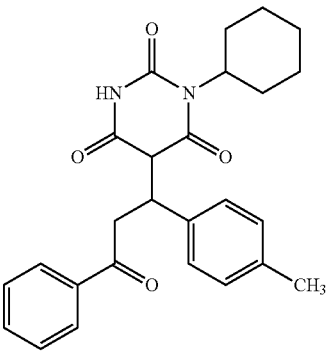
A-27
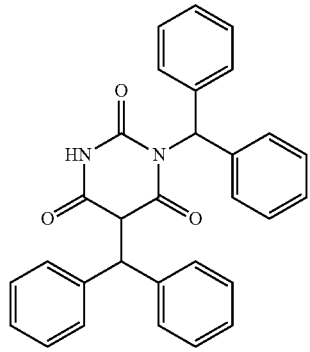
A-28
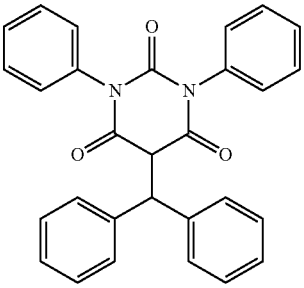
A-29
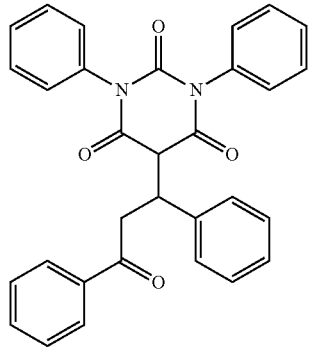
A-30
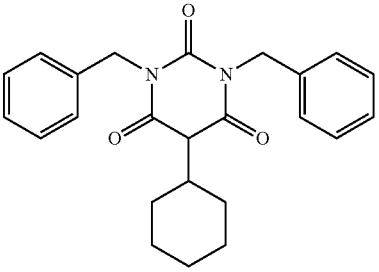

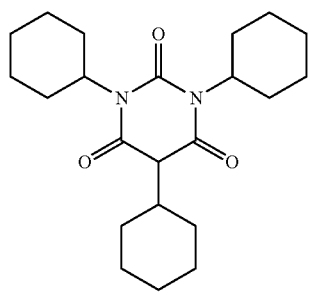
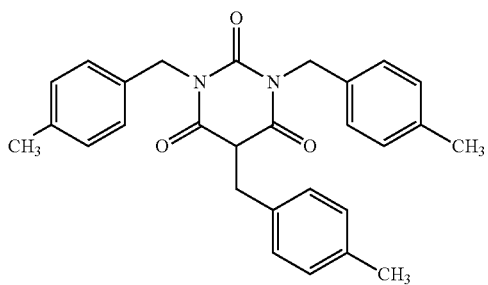
A-31
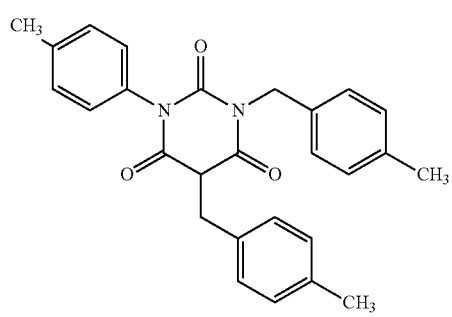
A-32
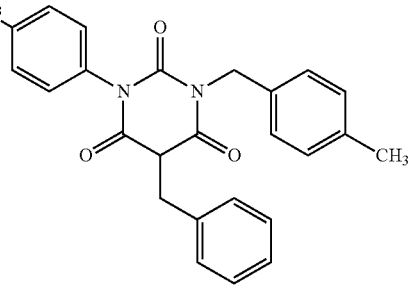
A-33
A-34
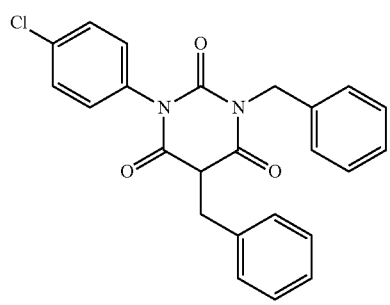
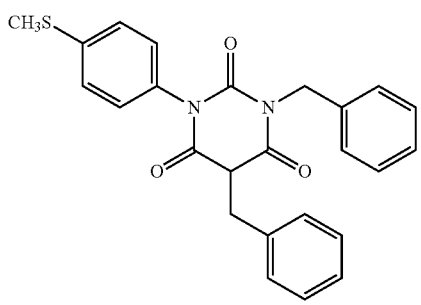
A-35
A-36
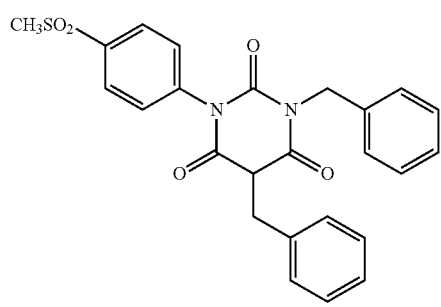
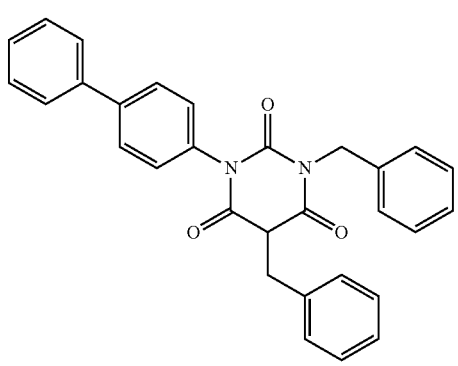
A-37
A-38
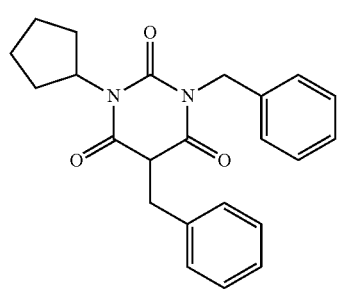
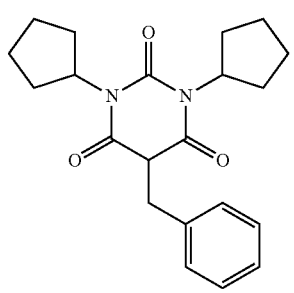
A-39
A-40

-continued
A-41
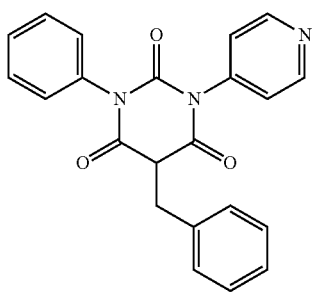
A-42
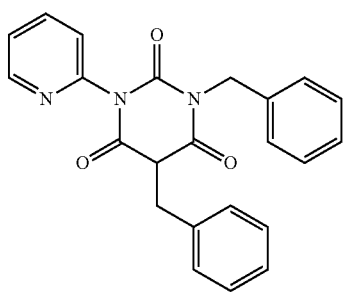
A-43
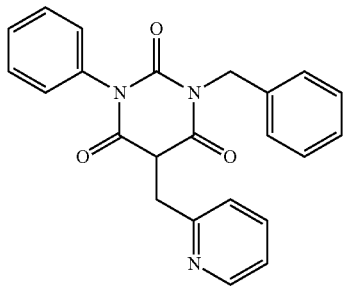
A-44
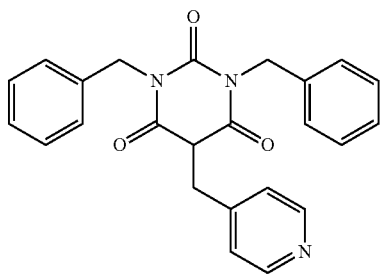
A-45
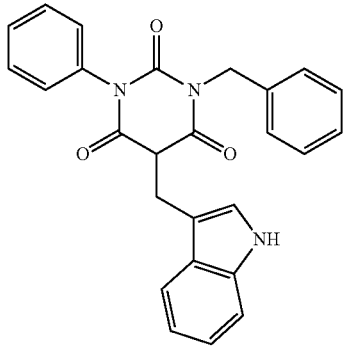
A-46
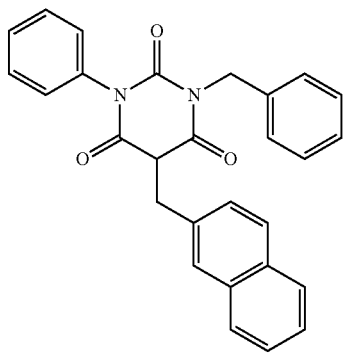
A-47
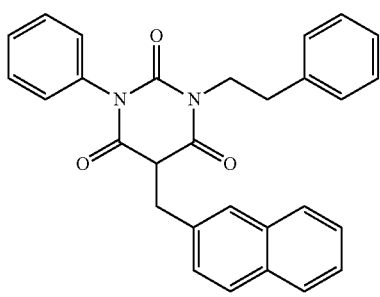
A-48
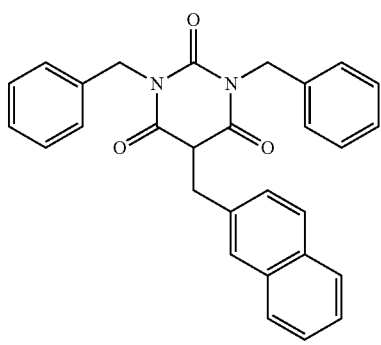
A-49
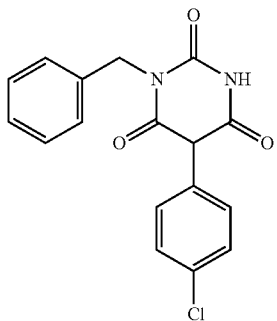
A-50
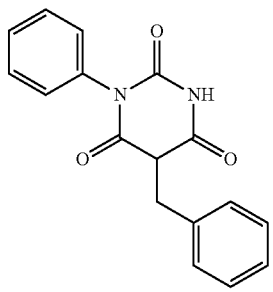

A-51 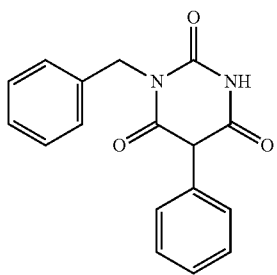
A-52 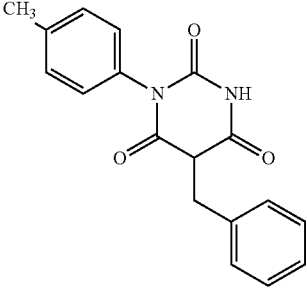
A-53 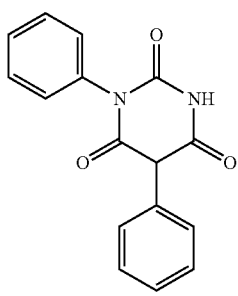
A-54 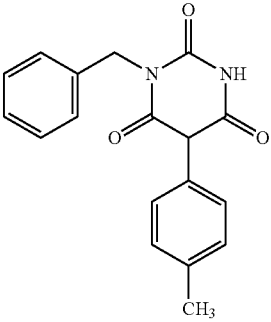
A-55 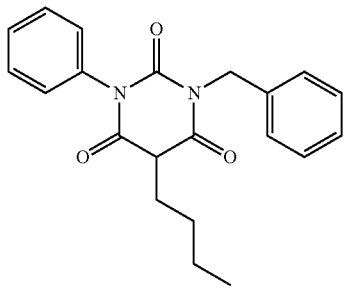
A-56 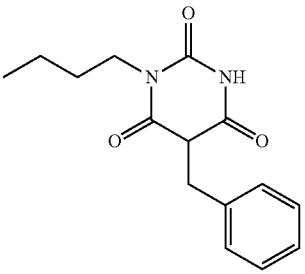
A-57 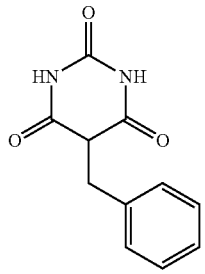
A-58 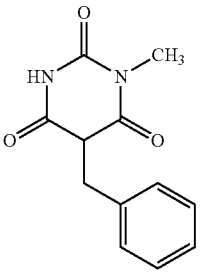
A-59 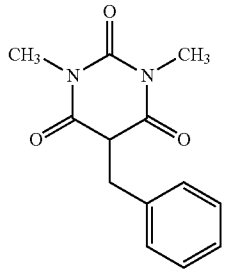
A-60 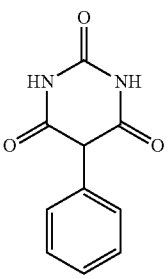

-continued
A-61
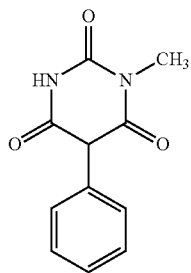
A-62
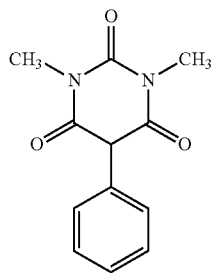
A-63
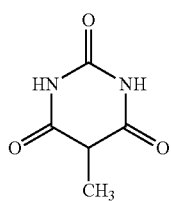
A-64
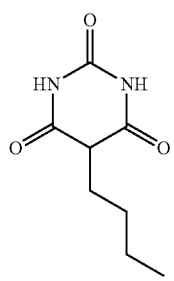
A-65
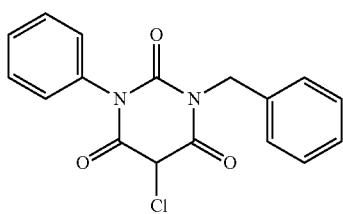
A-66
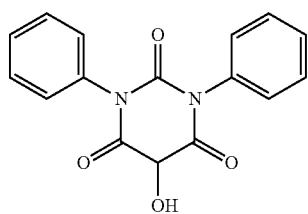
A-67
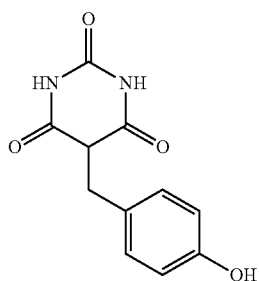
A-68
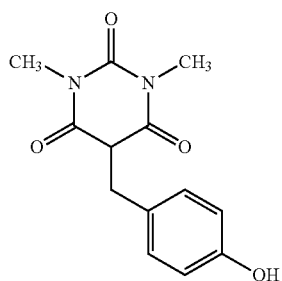
A-69
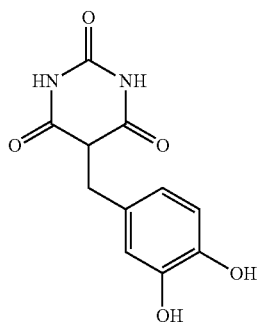
A-70
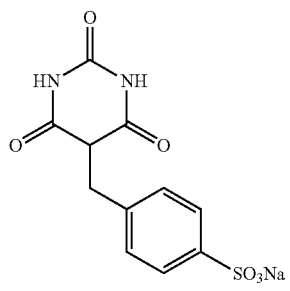

A-71 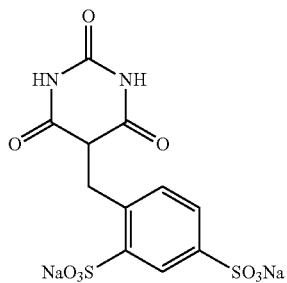
A-72 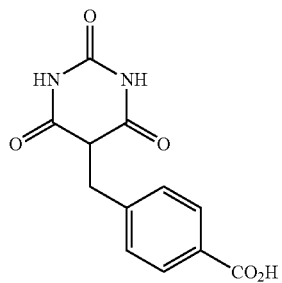
A-73 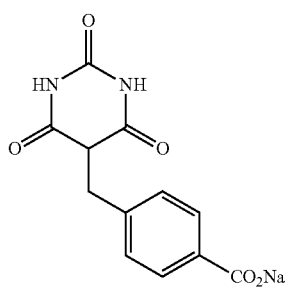
A-74 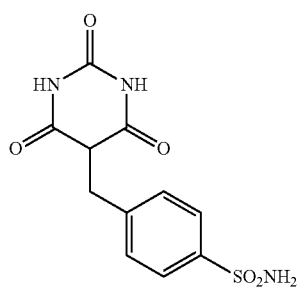
A-75 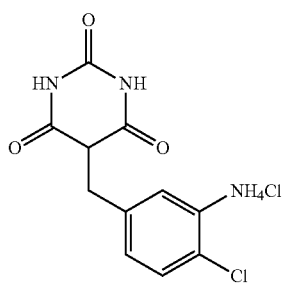
A-76 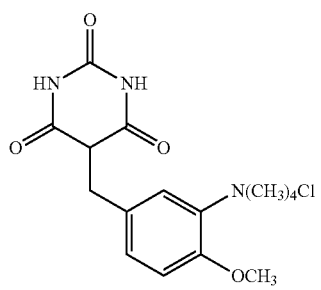
A-77 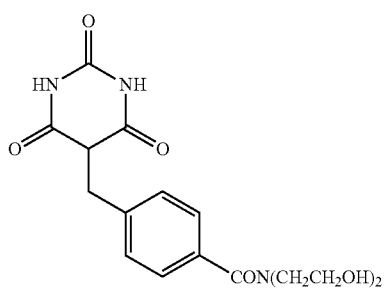
A-78 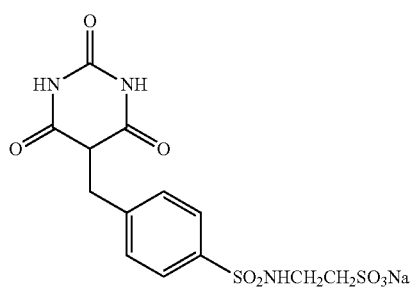
A-79 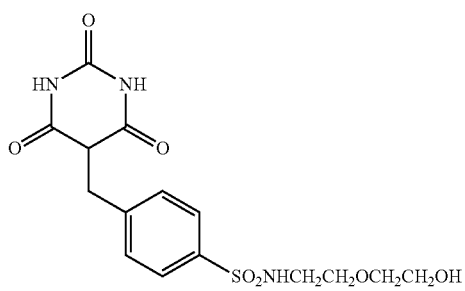
A-80 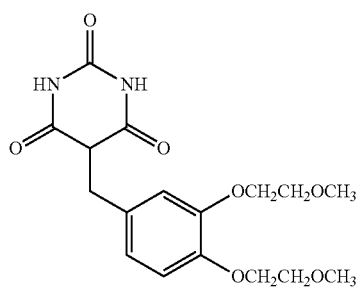

A-81
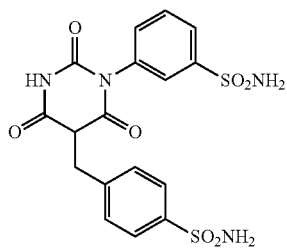
A-82
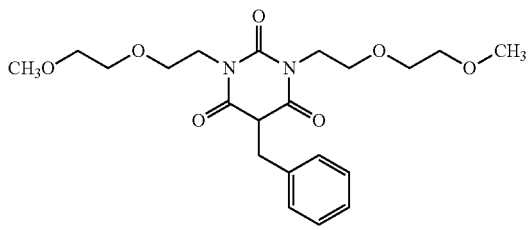
A-83
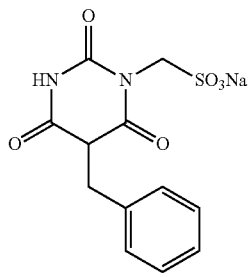
A-84
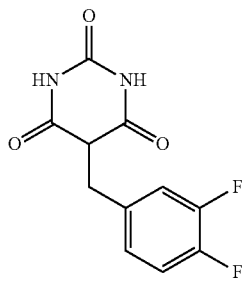
A-85
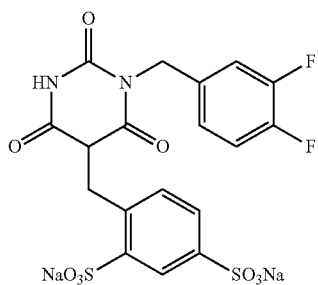
A-86
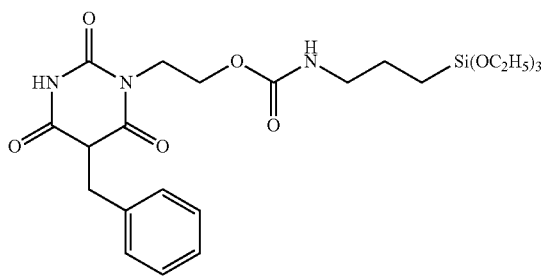
A-87
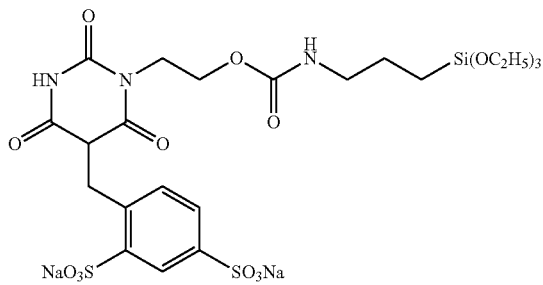
A-88
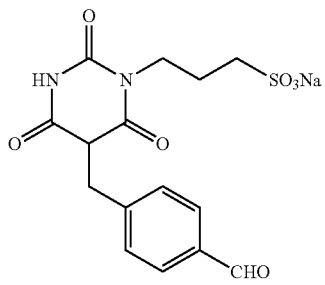
A-89
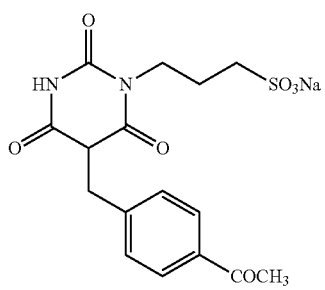
A-90
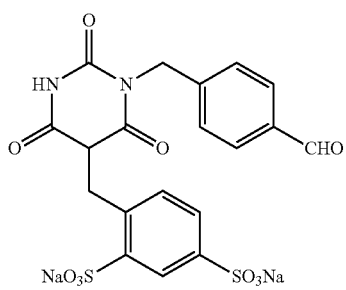

-continued
A-91
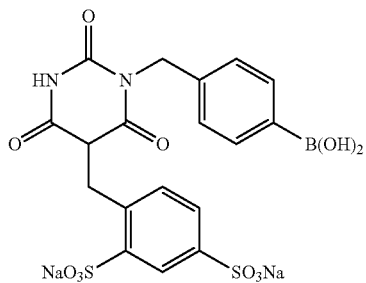
A-92
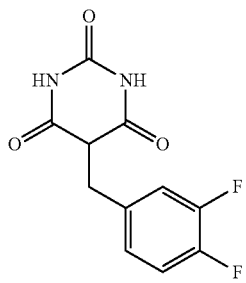
A-93
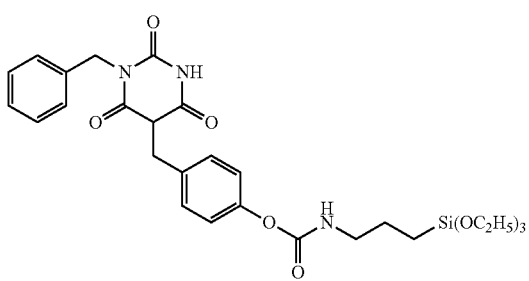
A-94
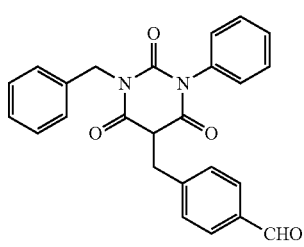
A-95
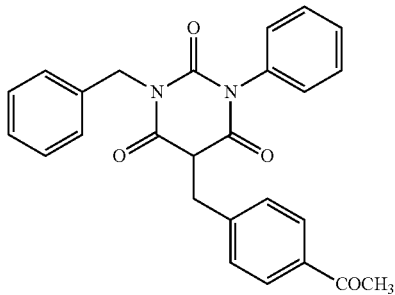
A-96
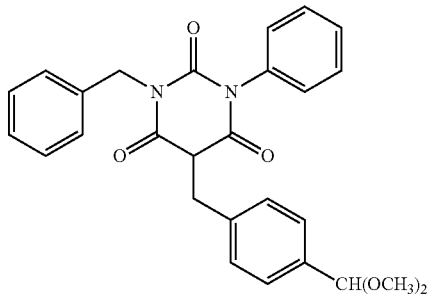
A-97
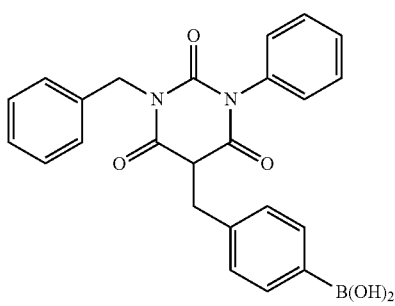
A-98
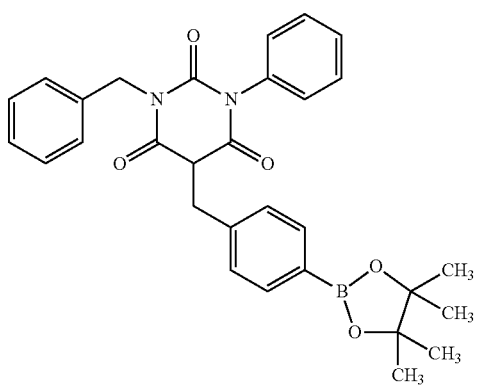
A-99
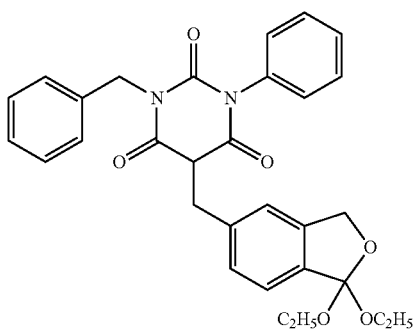
A-100
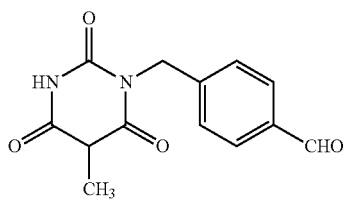

A-101 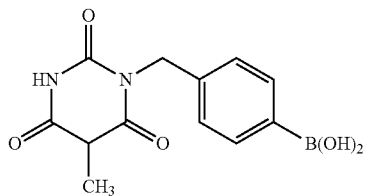
A-102 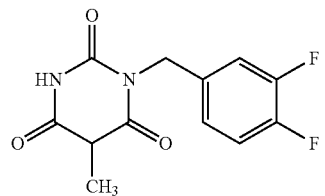
A-103 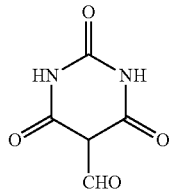
A-104 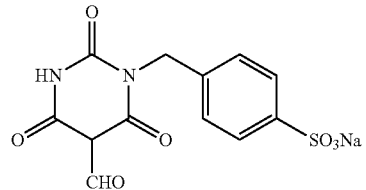
A-105 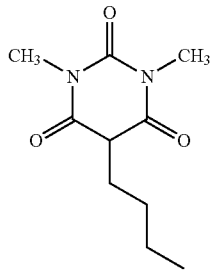
A-106 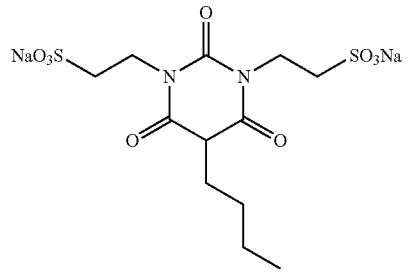
A-107 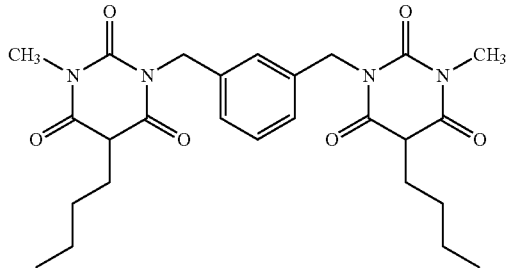
A-108 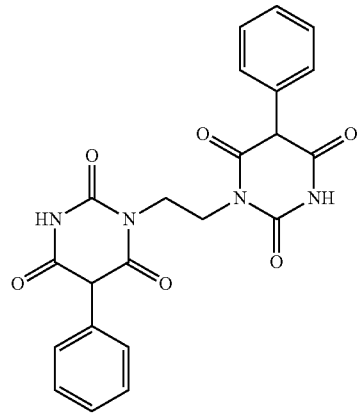
A-109 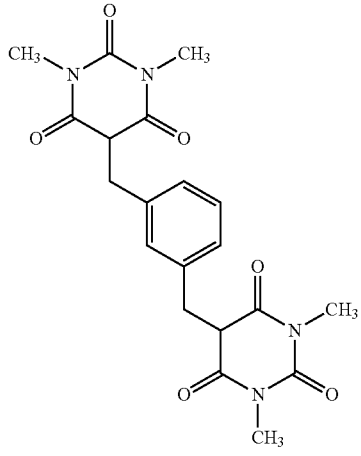
A-110 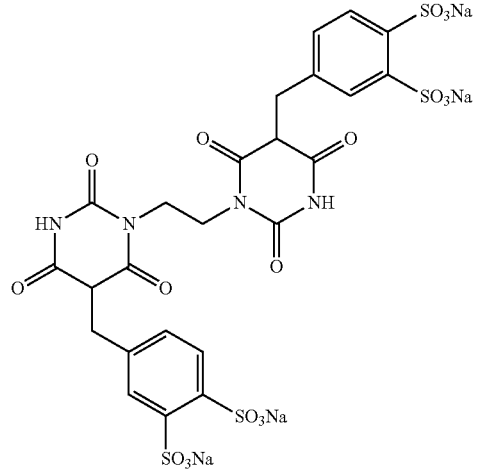

-continued
A-111
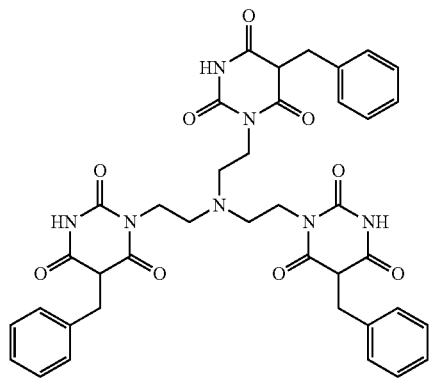
A-112
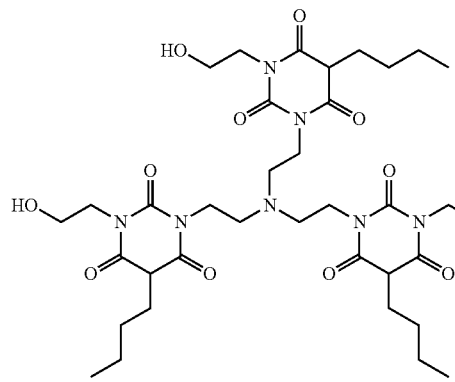
A-113
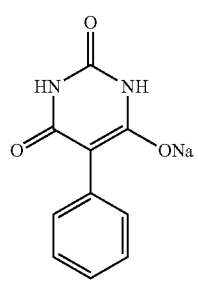
A-114
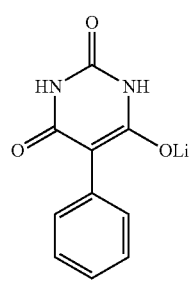
A-115
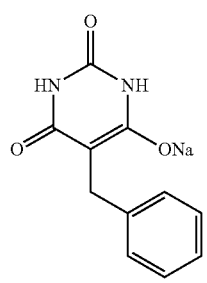
A-116
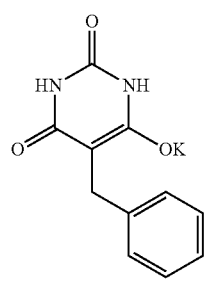
A-117
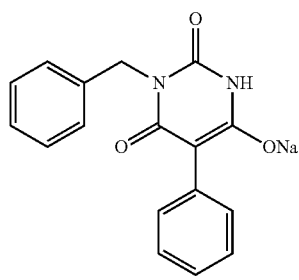
A-118
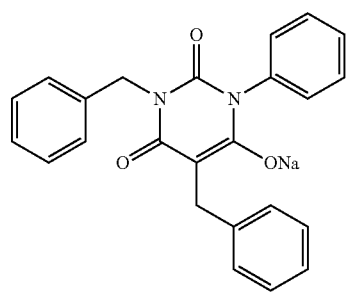
A-119
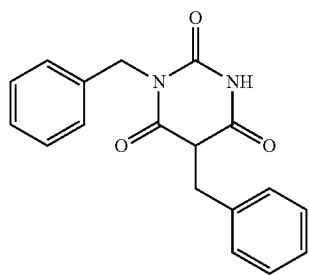
A-120
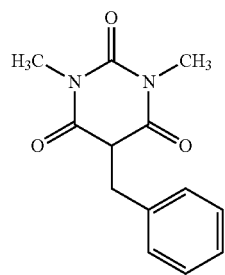

-continued

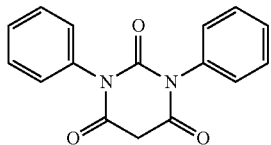
A-121

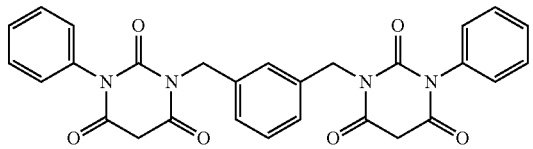
A-122

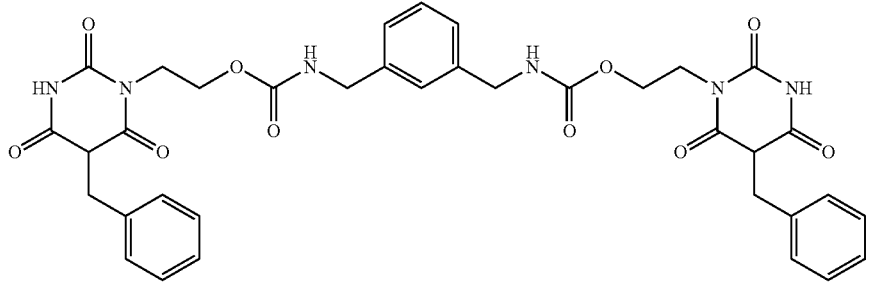
A-123

It is known that the compound represented by General Formula (A) can be synthesized by using a synthesis method of barbituric acid which causes condensation between a urea derivative and a malonic acid derivative. Barbituric acid including two substituents on a nitrogen atom is obtained by heating N,N'disubstituted urea and malonyl chloride or heating a combination of malonic acid and an activating agent such as acetic anhydride, and for example, methods disclosed in Journal of the American Chemical Society, Vol. 61, pp. 1015 (1939), Journal of Medicinal Chemistry, Vol. 54, pp. 2409 (2011), Tetrahedron Letters, Vol. 40, pp. 8029 (1999), and WO2007/150011A can be preferably used. Malonic acid used in condensation may be non-substituted malonic acid or may be a substituent malonic acid, and when malonic acid including a substituent corresponding to $R^5$ is used, it is possible to synthesize the compound represented by General Formula (A) by obtaining barbituric acid. In addition, when non-substituted malonic acid and a urea derivative are condensed, barbituric acid in which fifth position is a substituent is obtained, and therefore, the compound represented by General Formula (A) may be synthesized by modifying this.

As a method of modifying the fifth position, a nucleophilic substitution reaction with alkyl halide or the like or an addition reaction such as a Michael addition reaction can be used. In addition, a method of performing dehydration synthesis of aldehyde ad ketone to generate an alkylidene or arylidene compound and then reducing a double bond can also be preferably used. For example, a reducing method by zinc is disclosed in Tetrahedron Letters, Vol. 44, pp. 2203 (2003), a reducing method by catalytic reduction is disclosed in Tetrahedron Letters, Vol. 42, pp. 4103 (2001) or Journal of the American Chemical Society, Vol 119, 12849 (1997), and a reducing method by NaBH$_4$ is disclosed in Tetrahedron Letters, Vol. 28 pp. 4173 (1987), respectively. All of these are synthesis methods which can be preferably used in a case where an aralkyl group is included in the fifth position or a cycloalkyl group is included in the fifth position.

The synthesis method of the compound represented by General Formula (A) is not particularly limited thereto.

The content of the compound represented by General Formula (A) in the polarizing plate protective film is not particularly limited, and is preferably 0.1 to 20 parts by mass, more preferably 0.2 to 15 parts by mass, and particularly preferably 0.3 to 10 parts by mass with respect to 100 parts by mass of the resin configuring the polarizing plate protective film.

When the amount of the compound represented by General Formula (A) added is set to be in the range described above, it is possible to effectively decrease water vapor permeability and occurrence of haze is prevented.

(Amide-Based, Urethane-Based, and Ureide-Based Additives)

In the polarizing plate protective film of the invention, it is also preferable that a compound represent by the following General Formula (B-I) or a compound represent by General Formula (B-II) which will be described later is used. The compound represent by the following General Formula (B-I) or the compound represent by General Formula (B-II) which will be described later is preferable, from a viewpoint of an effect of increasing hardness of a film or an effect of preventing performance deterioration of the a polarizer due to wet heat. The compound is particularly preferable in a case where the resin configuring the polarizing plate protective film is cellulose acylate.

General Formula (B-I)

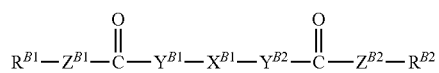

In General Formula (B-I), $R^{B1}$ and $R^{B2}$ each independently represent an alkyl group having 1 to 20 carbon atoms or an aryl group having 6 to 20 carbon atoms. $Z^{B1}$ and $Z^{B2}$ each independently represent a single bond, —O—, or —(N(R$^{Ba}$)—. Here, $R^{Ba}$ is a hydrogen atom or an alkyl group having 1 to 20 carbon atoms. $R^{Ba}$ and $R^{B1}$ or $R^{B2}$ may be bonded to each other to form a ring. $X^{B1}$ represents a divalent linking group, and an alkylene group having 1 to 6 carbon atom, a cycloalkylene group having 5 to 20 carbon atoms, an arylene group having 6 to 20 carbon atoms, s-triazine-2,4,6-trione-1,3-diyl, —O—, —NH—, —C(=O)—, or a group obtained by combining these groups is preferable. $Y^{B1}$ and $Y^{B2}$ each independently represent —NH— or —O—.

The alkyl group and the aryl group of $R^{B1}$ and $R^{B2}$ are preferably the alkyl group and the aryl group of $R^{A1}$, $R^{A3}$, and $R^{A5}$ of General Formula (A).

Each group of $R^{B1}$, $R^{B2}$, $X^{B1}$, and $R^{Ba}$ may further include a substituent, and examples of such a substituent include a carbamoyloxy group (including an alkylcarbamoyloxy group and an arylcarbamoyloxy group, preferably having 2 to 20 carbon atoms, for example, N-methylcarbamoyloxy, N,N-dimethylcarbamoyloxy, N-phenylcarbamoyloxy, or N-methyl-N-phenylcarbamoyloxy), a carbamoylamino group (including an alkylcarbamoylamino group and an arylcarbamoylamino group, preferably having 2 to 20 carbon atoms, for example, N-methylcarbamoylamino, N,N-dimethylcarbamoylamino, N-phenylcarbamoylamino, or N-methyl-N-phenylcarbamoylamino), an alkoxycarbonylamino group (preferably having 2 to 20 carbon atoms, for example, methoxycarbonylamino, ethoxycarbonylamino, or 2-ethylhexyloxycarbonylamino), an aryloxycarbonylamino group (preferably having 7 to 20 carbon atoms, for example, phenoxycarbonylamino or naphthoxycarbonylamino), —$Y^{B1}$—C(=O)—$Z^{B1}$—$R^{B1}$ ($R^{B1}$, $Z^{B1}$, and $Y^{B1}$ are identical to $R^{B1}$, $Z^{B1}$, and $Y^{B1}$ of General Formula (B-I)), in addition to the group of the substituent which each group of $R^{A1}$, $R^{A3}$, and $R^{A5}$ of General Formula (A) may be further substituted with a substituent.

Among these, as the substituent with which each group of $R^{B1}$, $R^{B2}$, $X^{B1}$, and $R^{Ba}$, an alkyl group, a cycloalkyl group, an aryl group, an alkoxy group, an aryloxy group, a hydroxy group, a cyano group, a carbamoyl group, an acylamino group, an acyl group, an acyloxy group, a carbamoyloxy group, carbamoylamino group, alkoxycarbonylamino group, aryloxycarbonylamino group, and —$Y^{B1}$—C(=O)—$Z^{B1}$—$R^{B1}$ are preferable.

Particularly, in a case where $R^{B2}$ is an alkyl group, an alkyl group in which a carbamoyl group, an acylamino group, an acyl group, an acyloxy group, a carbamoyloxy group, a carbamoylamino group, an alkoxycarbonylamino group, or an aryloxycarbonylamino group is substituted is preferable.

$X^{B1}$ is preferably groups represented by the following X-1 to X-8.

In the formulae, * indicates positions bonded to $Y^{B1}$ and $Y^{B2}$ of —$Y^{B1}$—C(=O)— and —$Y^{B2}$—C(=O)—. In addition, ** indicates positions bonded to —$Y^{B1}$—C(=O)—$Z^{B1}$—$R^{B1}$ which is a substituent which may be included in $X^{B1}$.

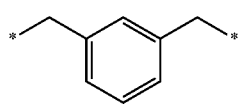

X-1

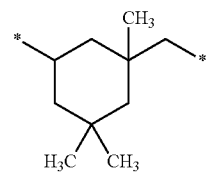

X-2

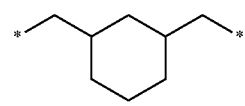

X-3

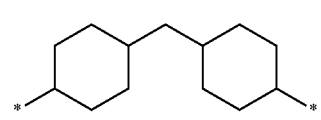

X-4

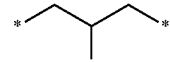

X-5

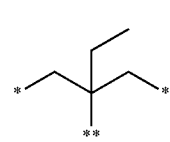

X-6

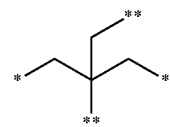

X-7

X-8

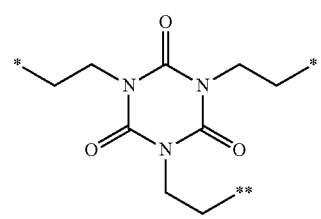

$R^{Ba}$ is preferably a hydrogen atom or an alkyl group having 1 to 8 carbon atoms, more preferably a hydrogen atom or an alkyl group having 1 to 3 carbon atoms, and even more preferably a hydrogen atom.

A ring formed by bonding $R^{Ba}$ and $R^{B1}$ or $R^{B2}$ is preferably 5-membered or 6-membered ring, and for example, a pyrrolidine ring, a piperidine ring, a piperazine ring, a morpholine ring, or a thiomorpholine ring is used.

$Y^{B1}$ and $Y^{B2}$ are preferably —NH—.

$Z^{B1}$ and $Z^{B2}$ are preferably —O—.

Hereinafter, specific examples of the compound represented by General Formula (B-I) are shown, but the invention is not limited thereto.

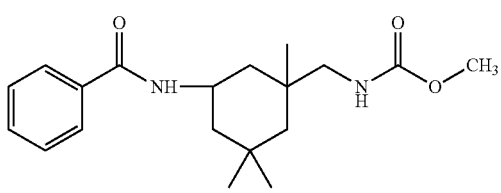

B-1

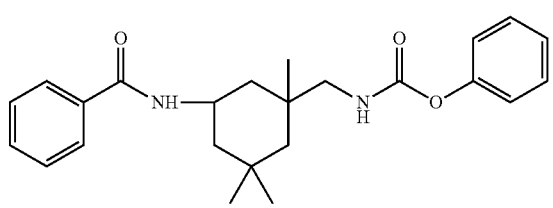

B-2

-continued
B-3
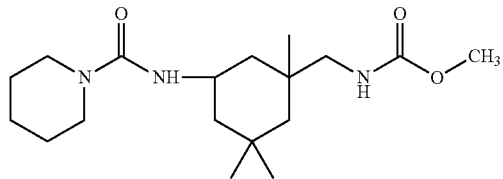
B-4
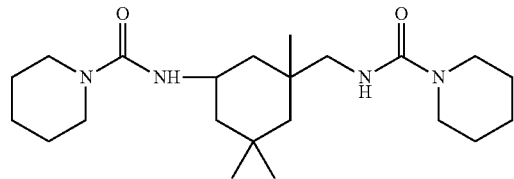
B-5
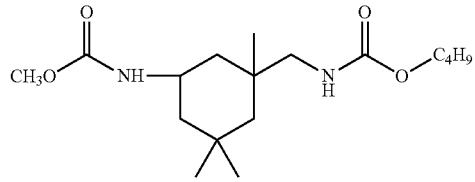
B-6
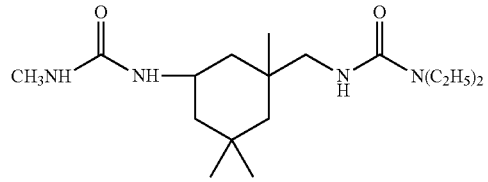
B-7
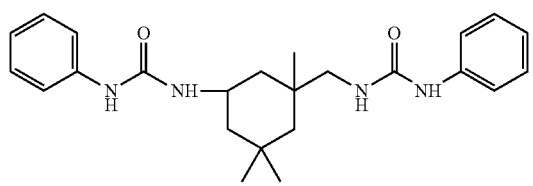
B-8
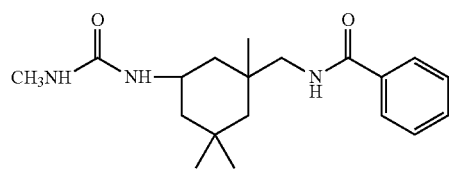
B-9
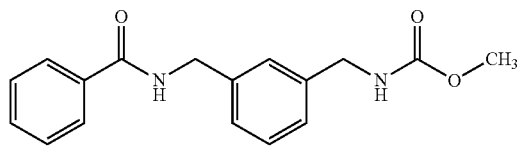
B-10
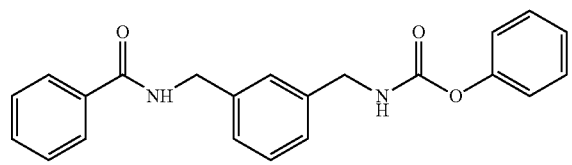
B-11
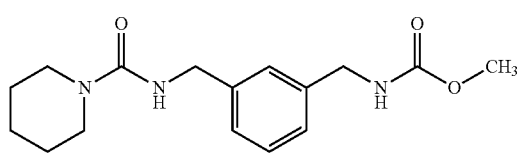
B-12
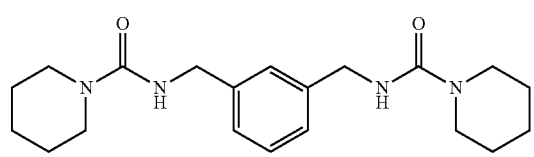
B-13
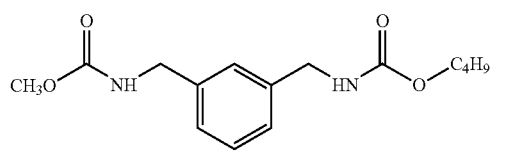
B-14
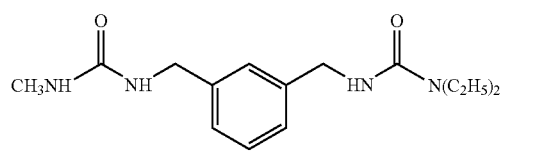
B-15
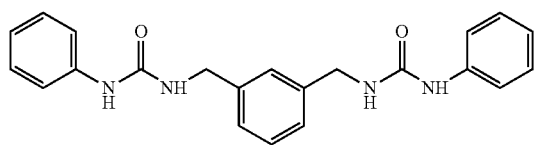
B-16
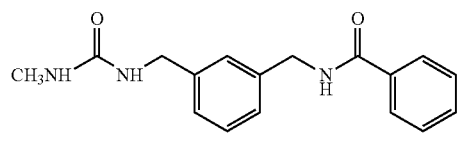
B-17
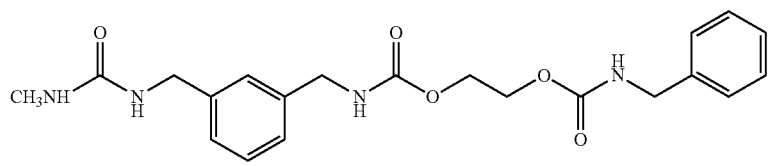
B-18
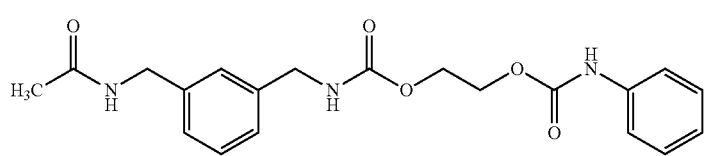

-continued
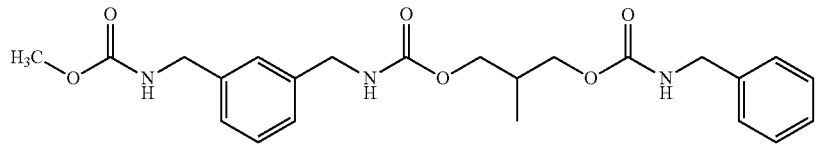
B-19
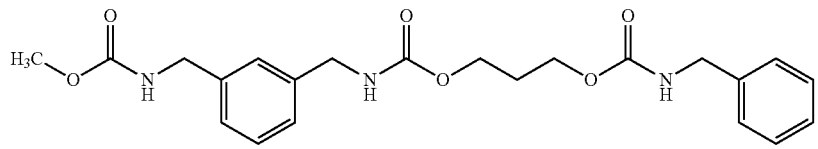
B-20
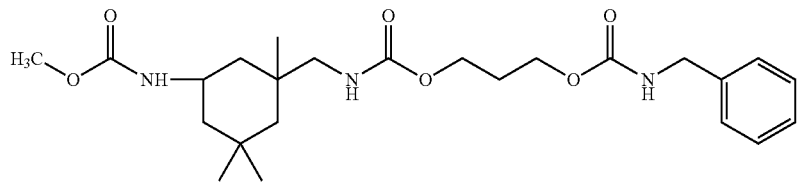
B-21
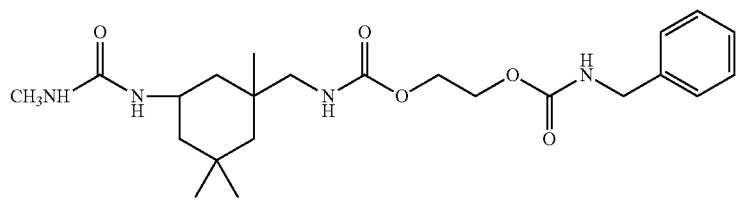
B-22
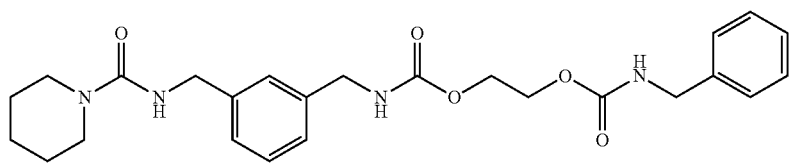
B-23
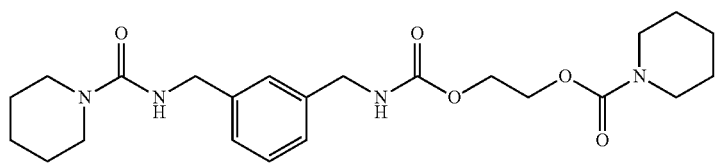
B-24
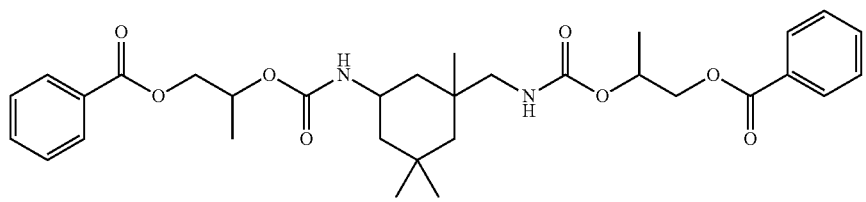
B-25
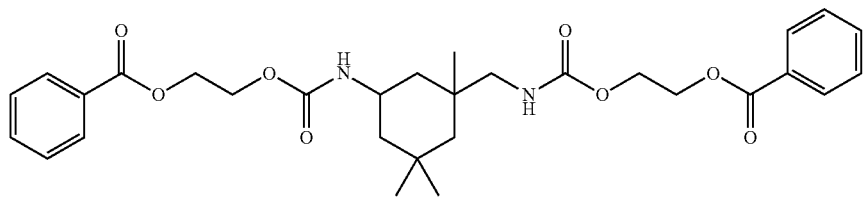
B-26

-continued
B-27
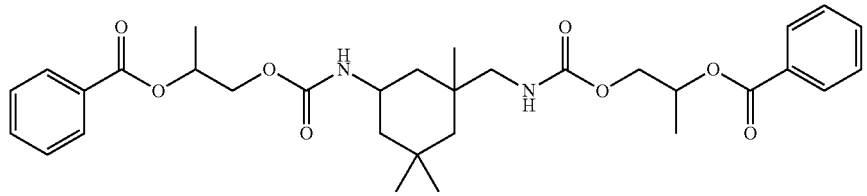
B-28
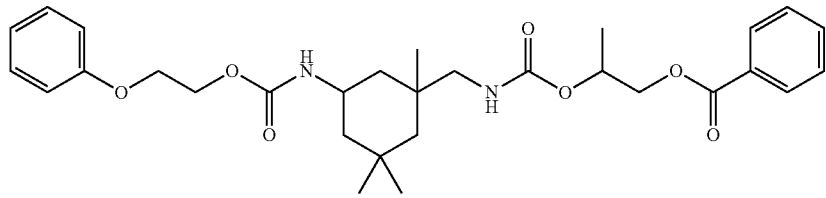
B-29
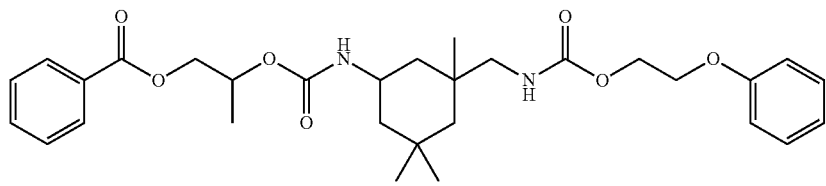
B-30
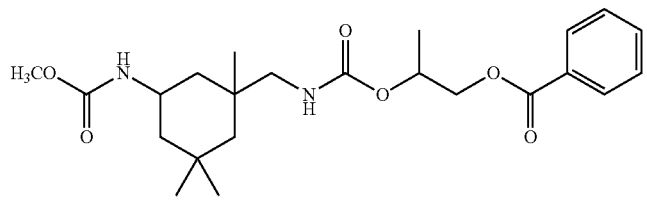
B-31
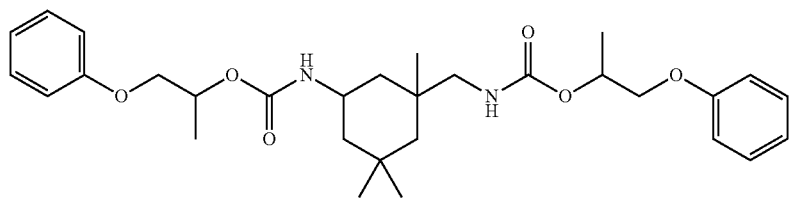
B-32
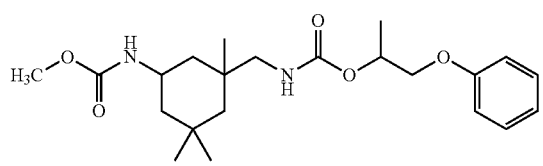
B-33
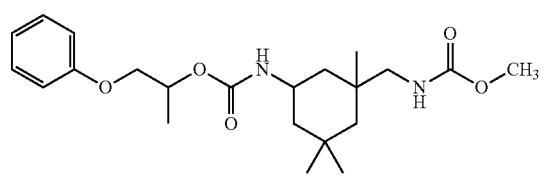
B-34
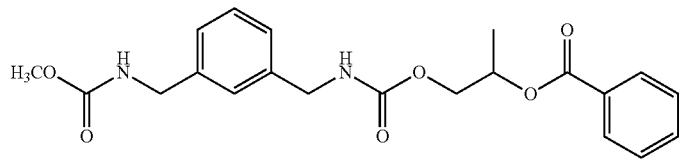
B-35
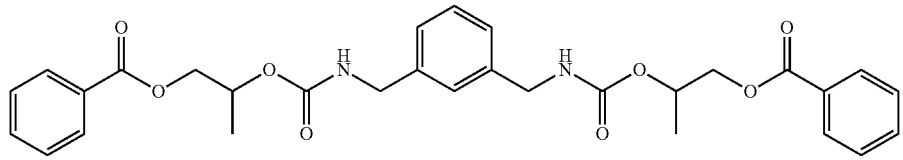

-continued
B-36
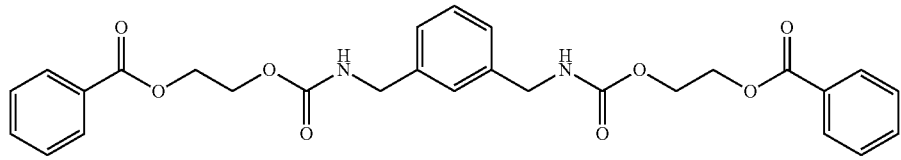
B-37
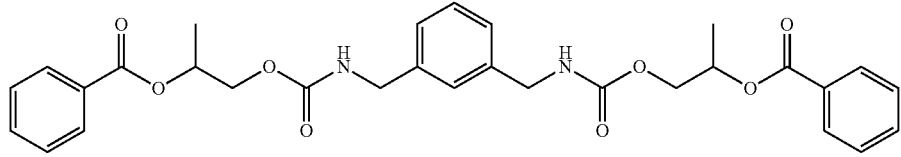
B-38
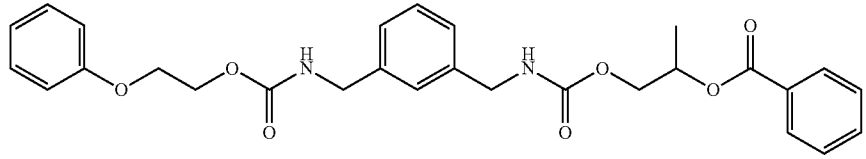
B-39
B-40
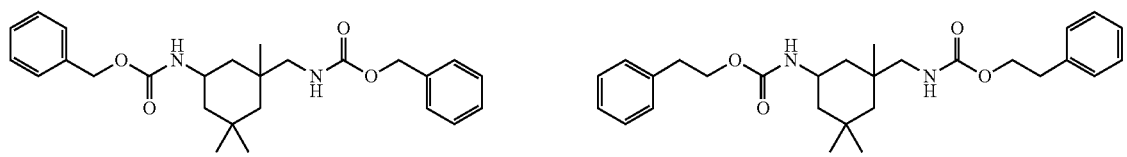
B-41
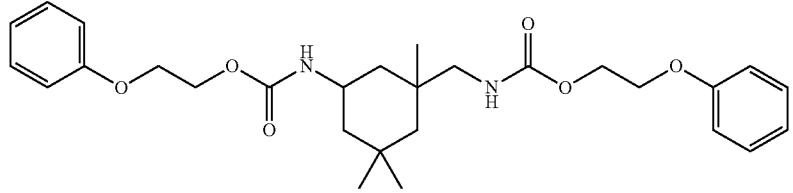
B-42
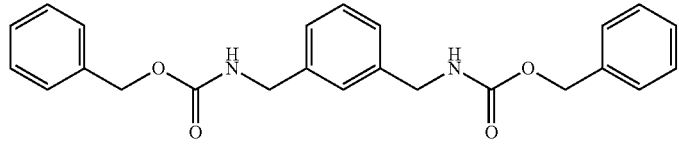
B-43
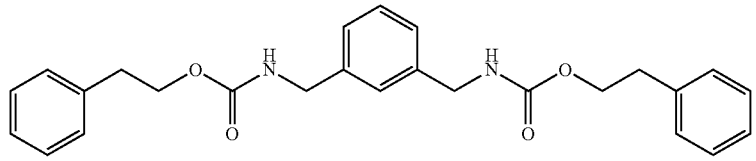
B-44
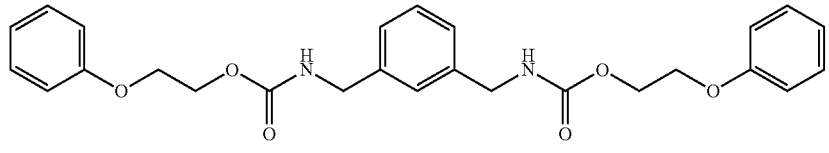
B-45
B-46
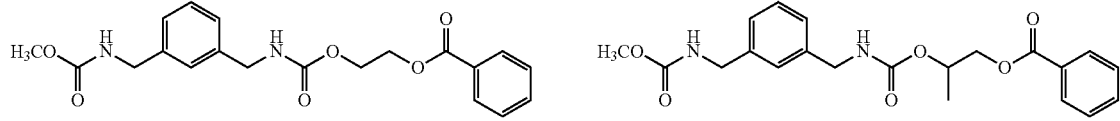

-continued
B-47
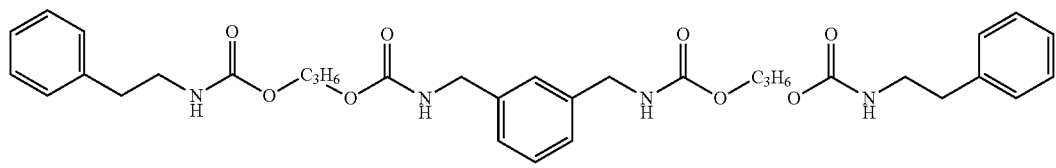
B-48
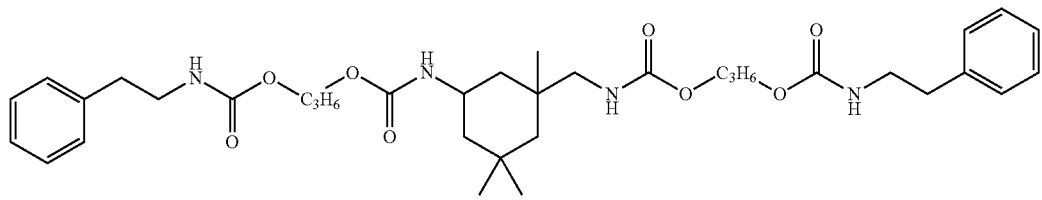
B-49
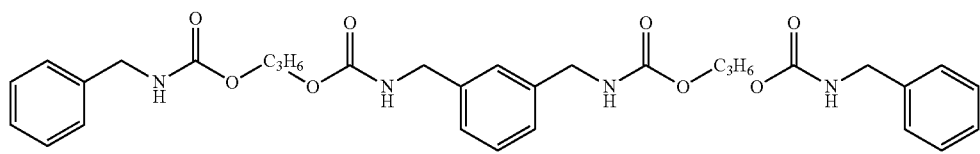
B-50
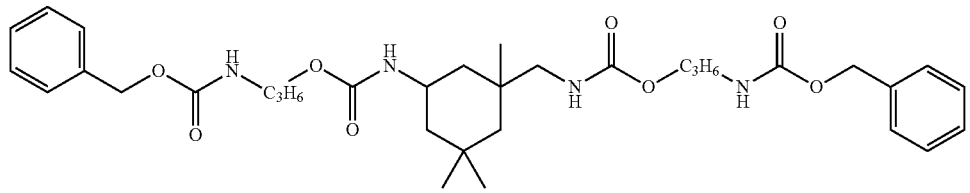
B-51
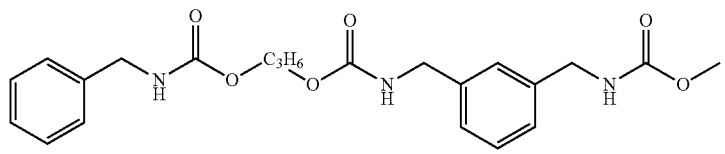
B-52
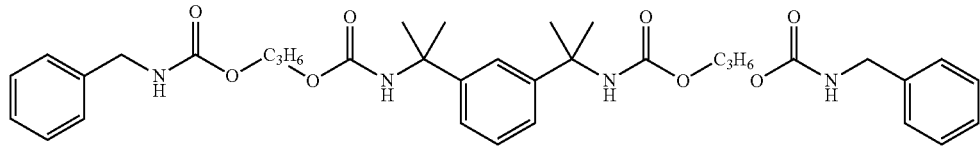
B-53
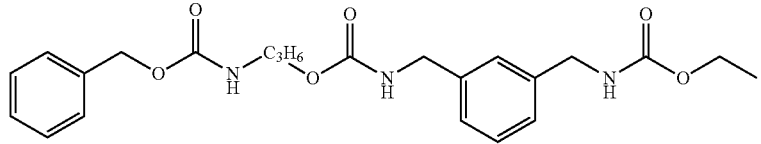
B-54
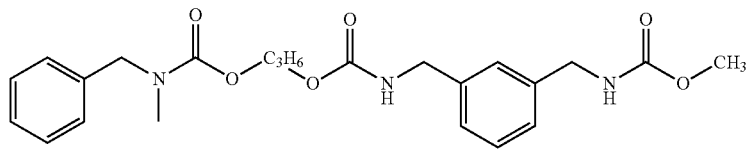
B-55
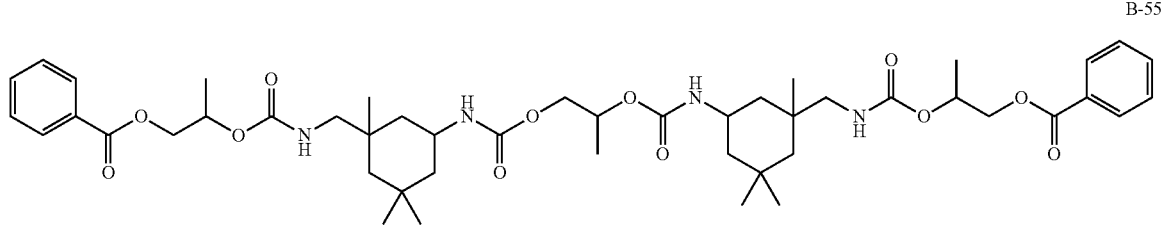 [SMILES: CC(COC(=O)c1ccccc1)OC(=O)NCC1(C)CC(NC(=O)OCCOC(=O)NC2CC(C)(C)CC(C)(CNC(=O)OC(C)COC(=O)c3ccccc3)C2)CC(C)(C)C1]

-continued
B-56
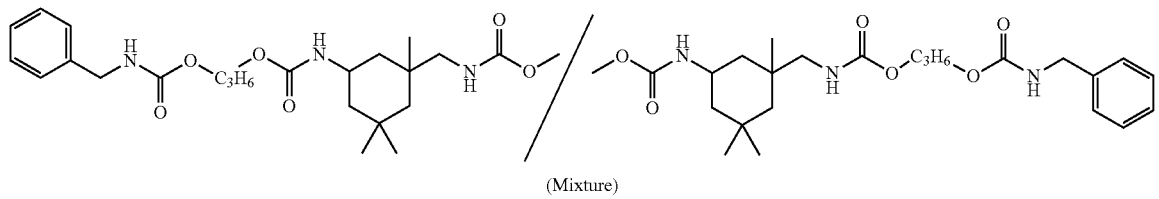
(Mixture)
B-57
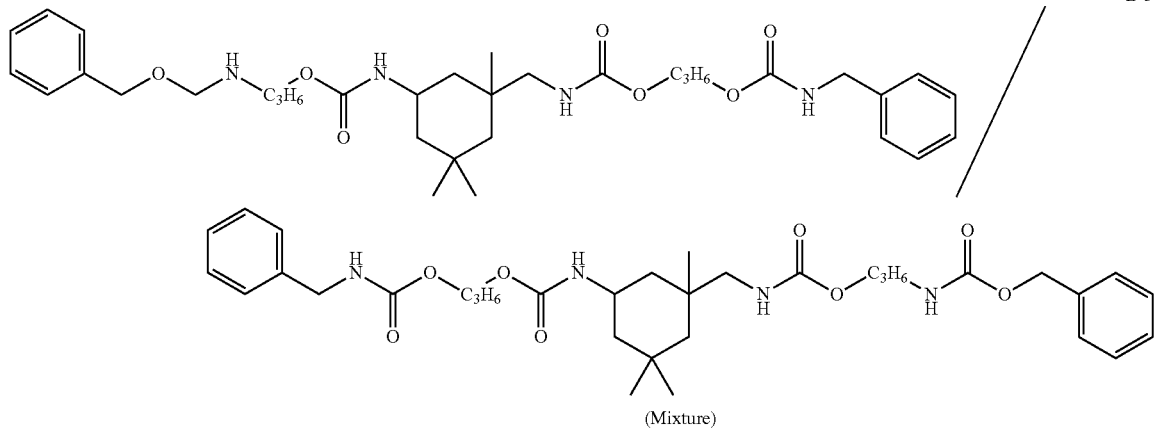
(Mixture)
B-58
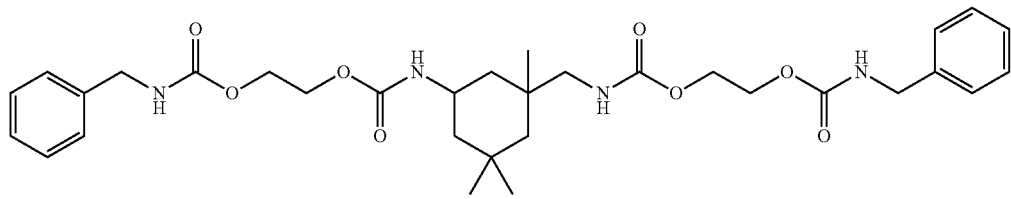
B-59
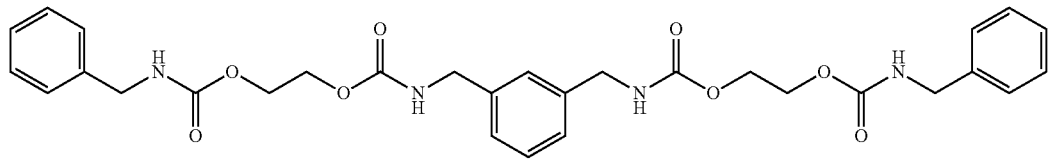
B-60
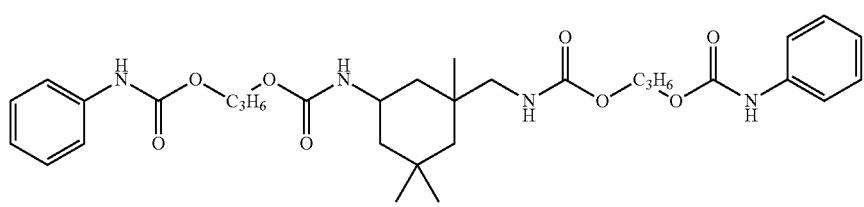
B-61
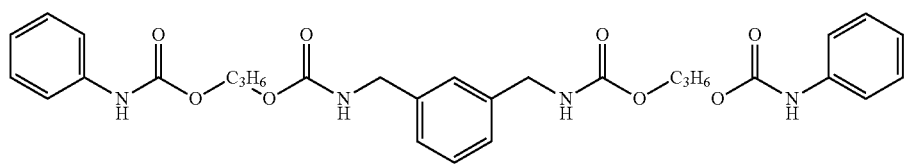
B-62
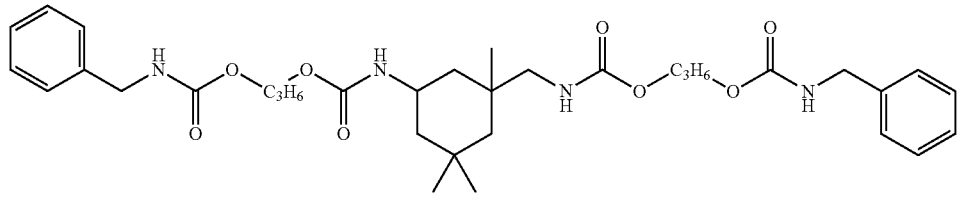

-continued
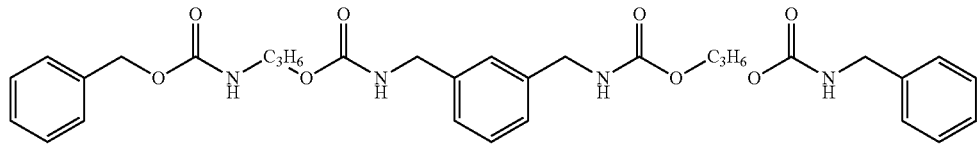
B-63
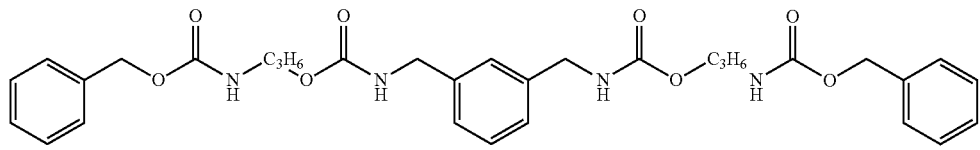
B-64
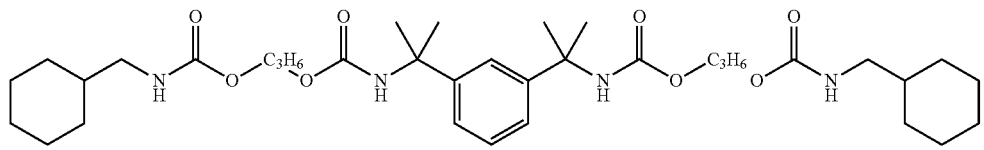
B-65
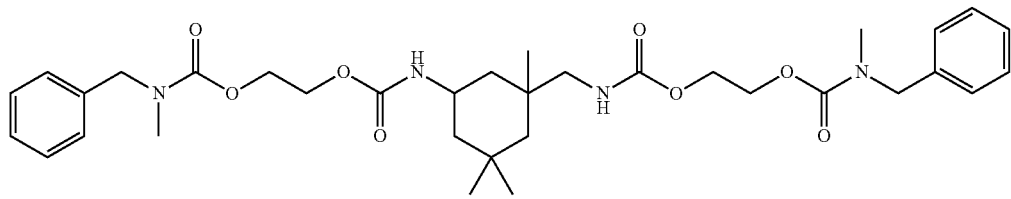
B-66
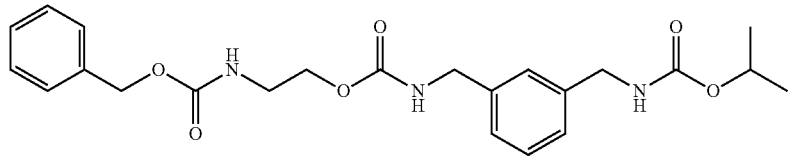
B-67
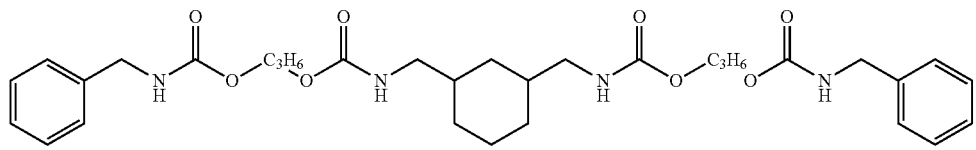
B-68
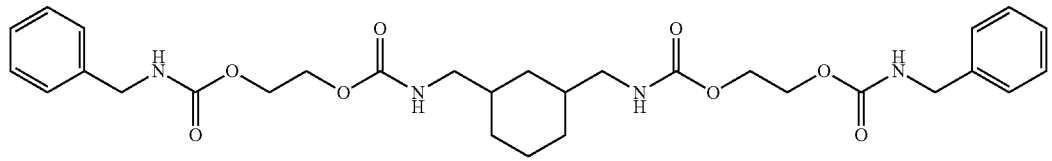
B-69
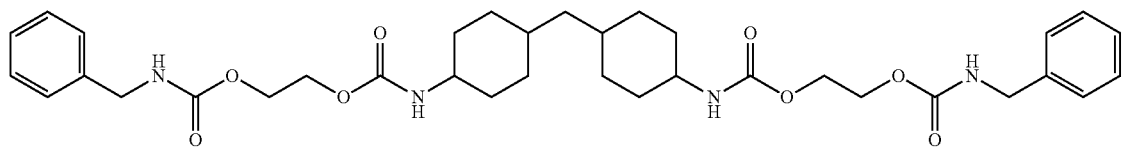
B-70
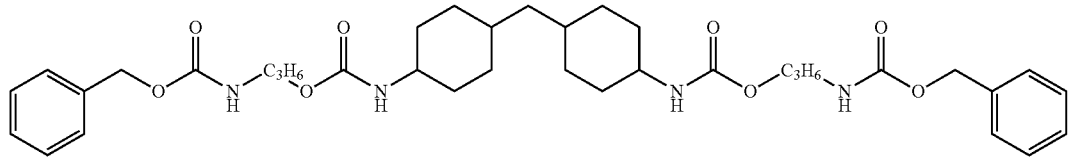
B-71

-continued
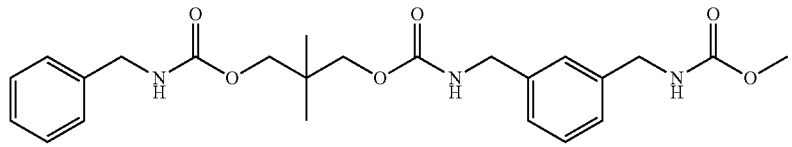
B-72
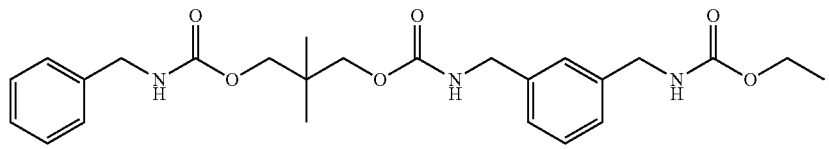
B-73
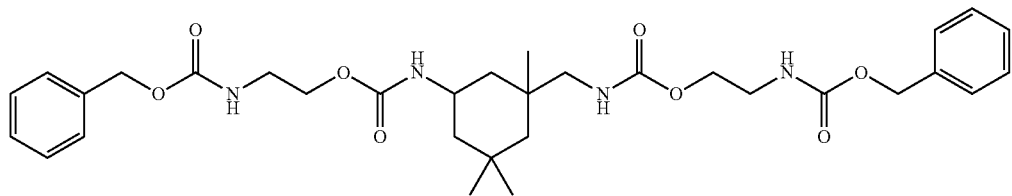
B-74
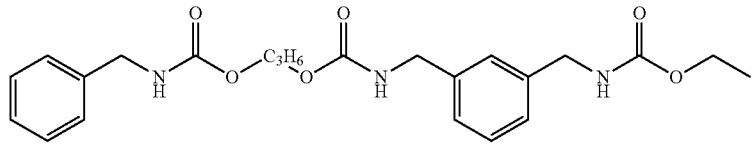
B-75
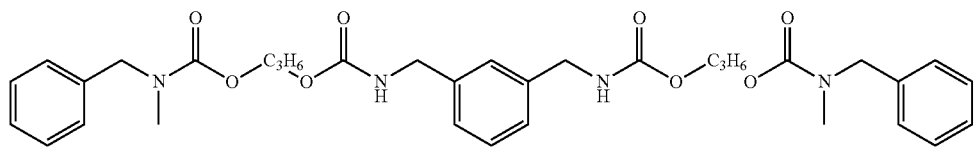
B-76
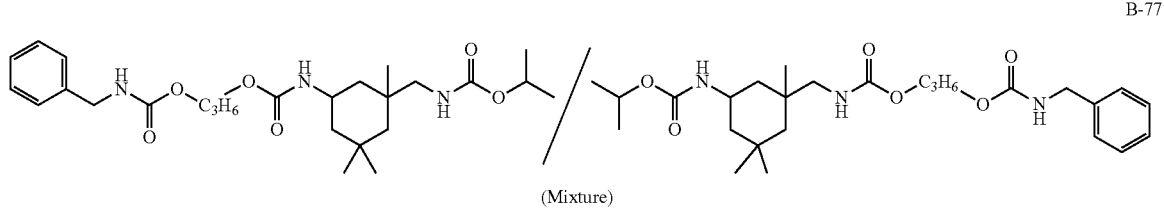
B-77
(Mixture)
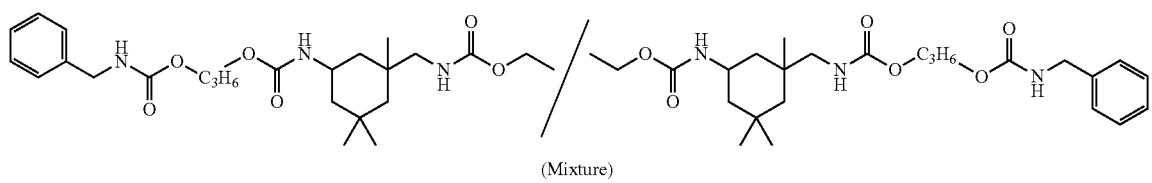
B-78
(Mixture)
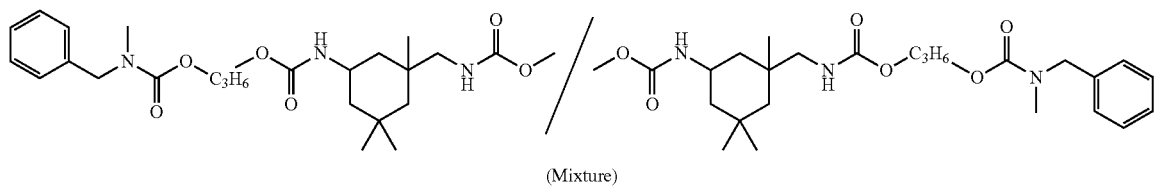
B-79
(Mixture)

-continued
B-80
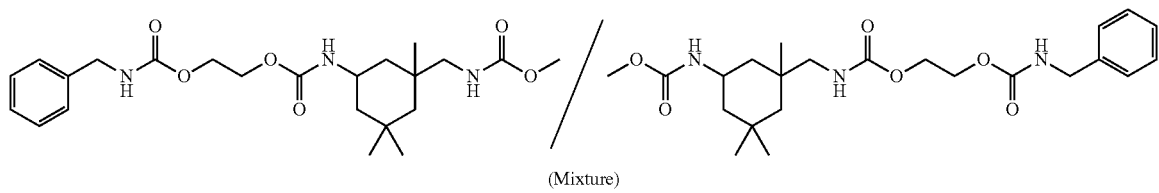
(Mixture)
B-81
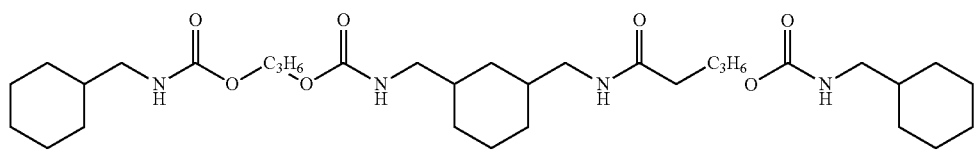
B-82
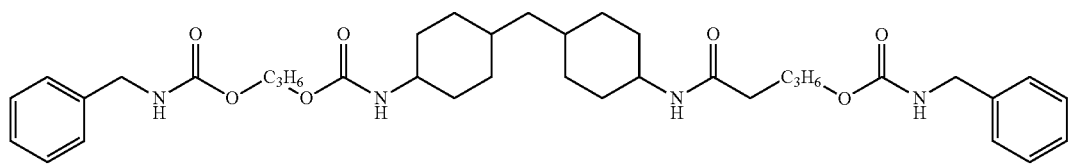
B-83
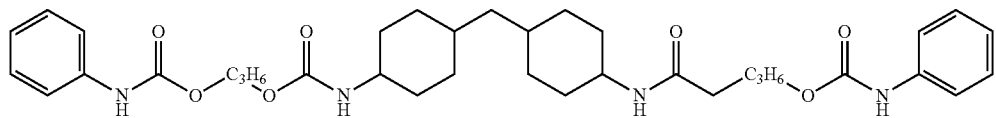
B-84
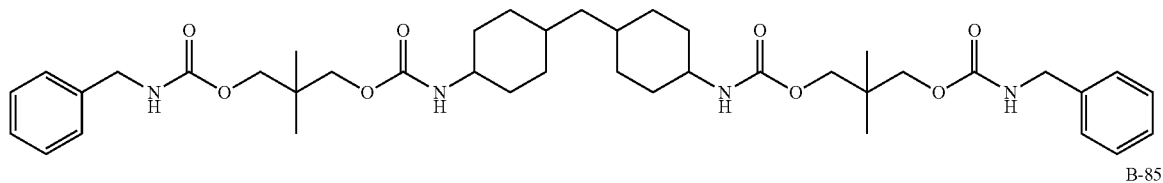
B-85
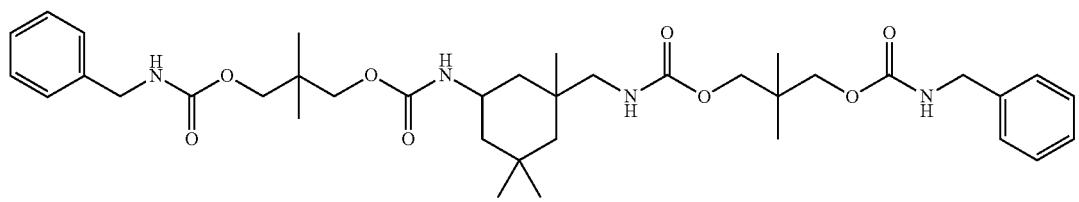
B-86
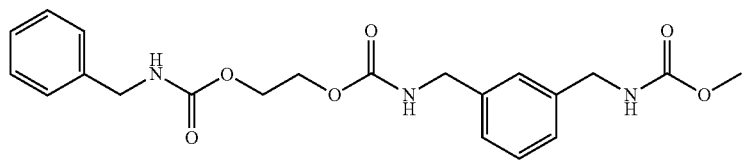
B-87
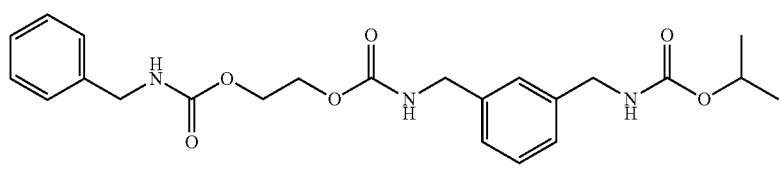
B-88
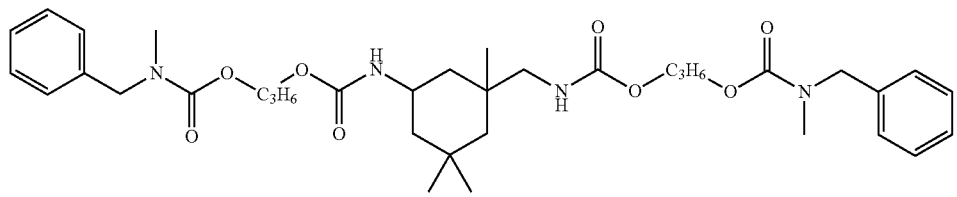

-continued
B-89
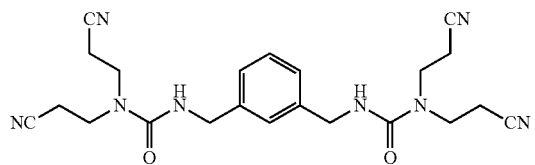
B-90
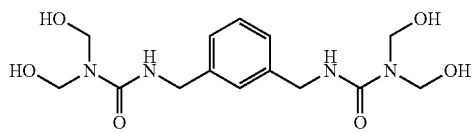
B-91
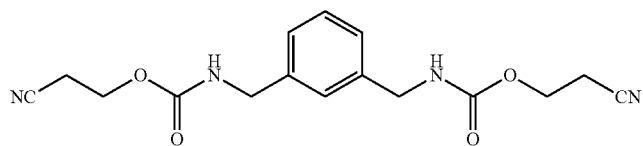
B-92
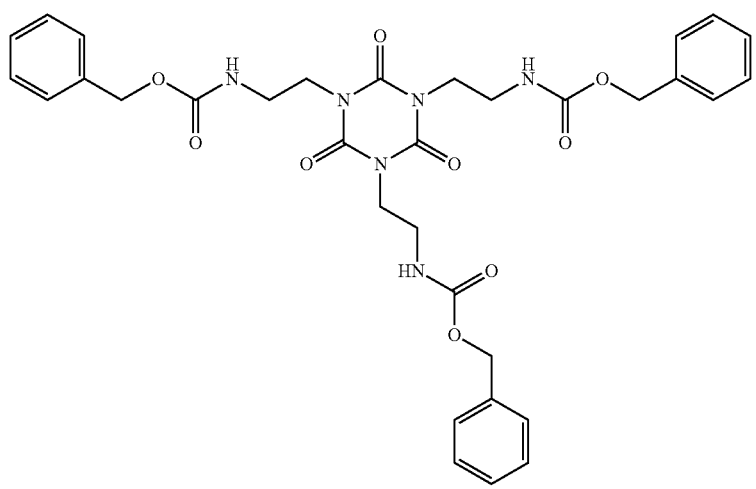
B-93
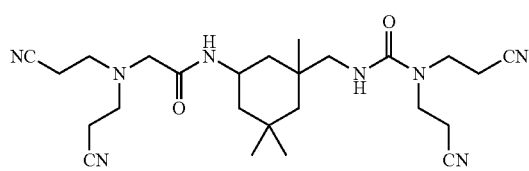
B-94
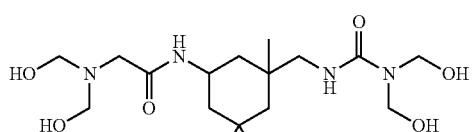
B-95
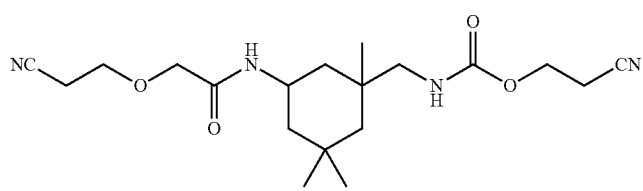
B-96
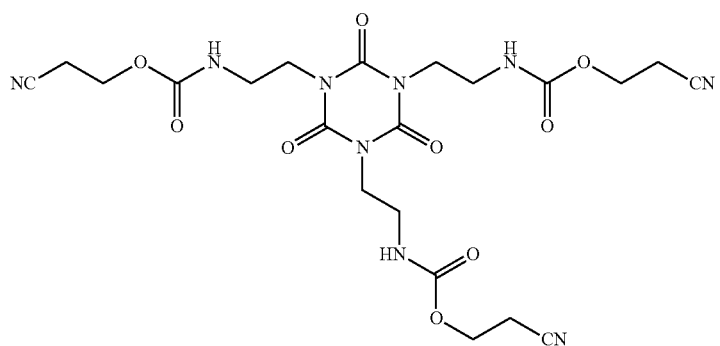

-continued
B-97
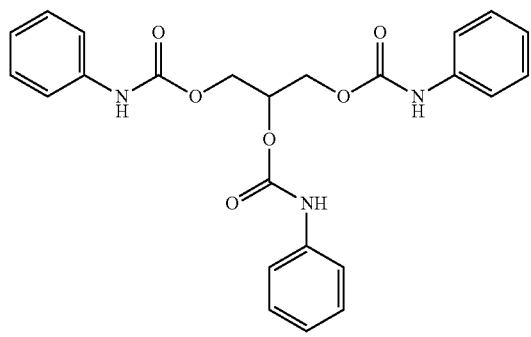
B-98
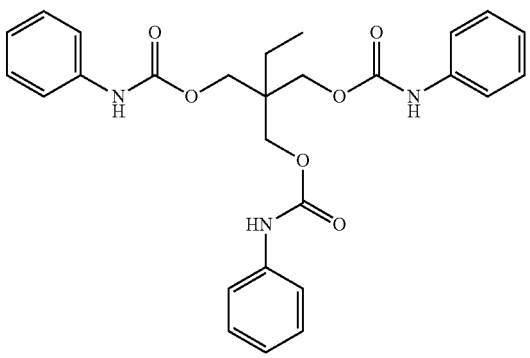
B-99
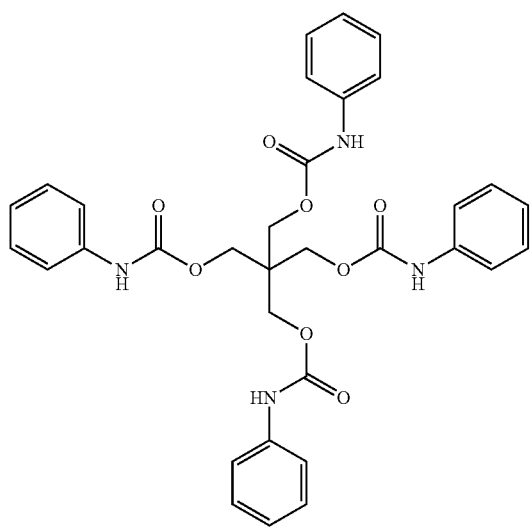
B-100
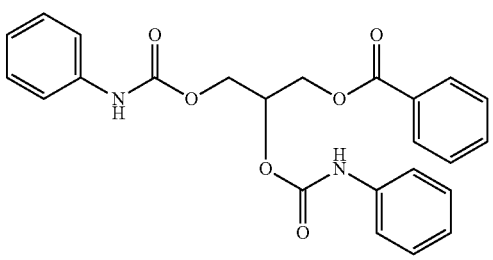
B-101
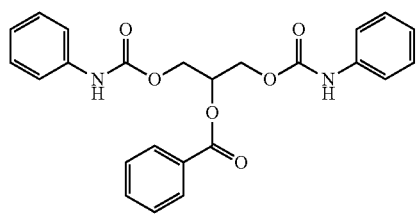
B-102
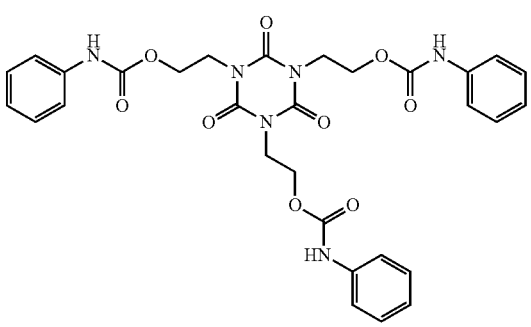
B-103
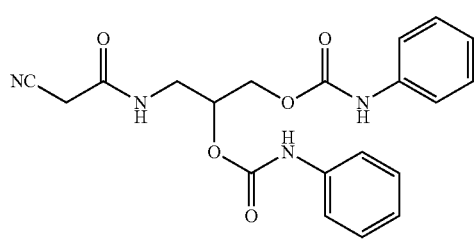

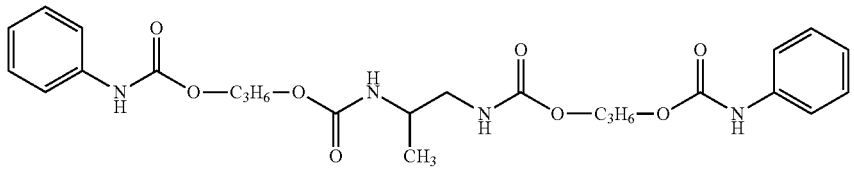
B-104
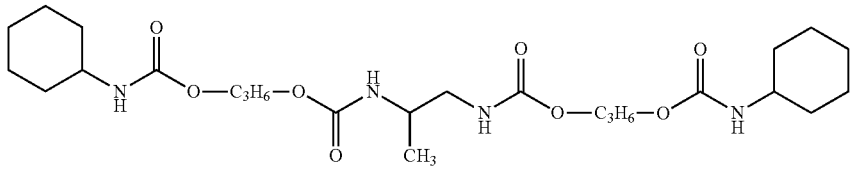
B-105
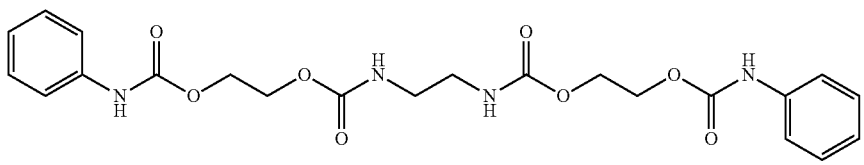
B-106
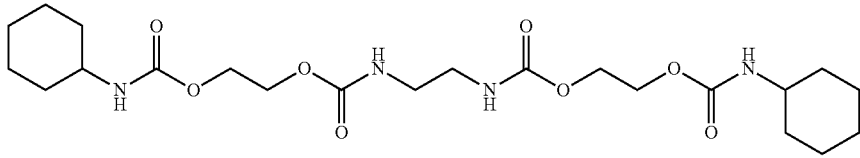
B-107
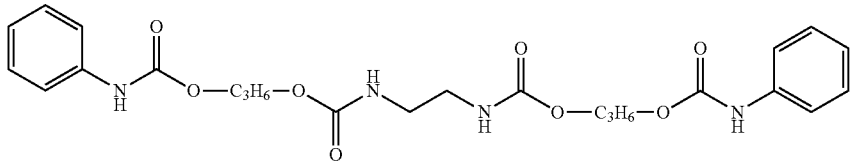
B-108
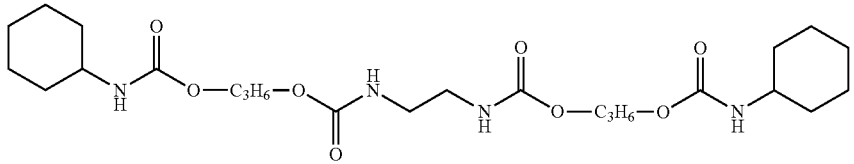
B-109
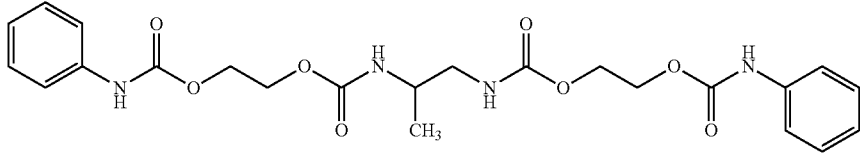
B-110
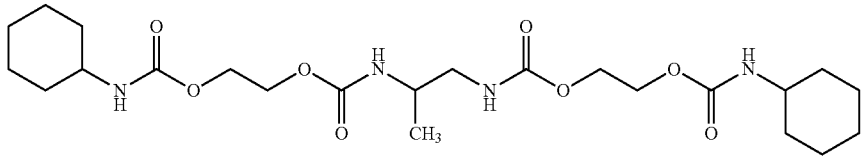
B-111

B-112

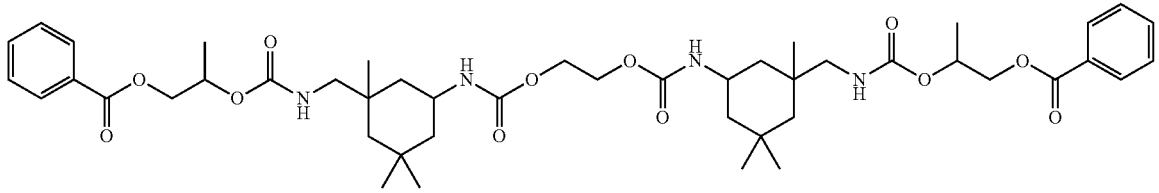

The compound represent by General Formula (B-I) can be prepared by a well-known method.

For example, the compound can be obtained by an addition reaction of alcohol to alkyl or aryl isocyanate or a condensation reaction between amine and carbonate.

At the time of the addition reaction of alcohol to alkyl or aryl isocyanate, it is also preferable to use a solvent, and as the solvent, an arbitrary urethanized solvent such as metal organic acid salt of amines, zinc, or tin or a metal chelating compound, or organic metal compound of zinc, tin, or bismuth can be used. As the urethanized solvent, dibutyltin dilaurate or dibutyltin diacetate is preferably used.

In addition, the synthesis can be performed even by acylation of divalent alcohol or a divalent amine compound.

In the invention, the compound represented by the following General Formula (B-II) is also preferable, in addition to the compound represent by General Formula (B-I) described above.

General Formula (B-II)

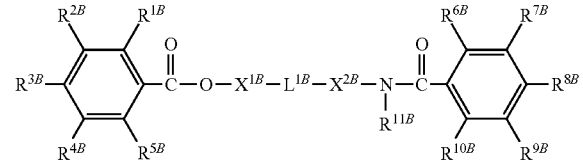

In General Formula (B-II), $R^{1B}$ to $R^{7B}$ and $R^{9B}$ to $R^{11B}$ each independently represent a hydrogen atom or a substituent, $R^{8B}$ represents a hydrogen atom or an unconjugated substituent, $X^{1B}$ and $X^{2B}$ each independently represent a single bond or an aliphatic linking group, and $L^{1B}$ represents a single bond, $-N(R^{12B})-$, or $-C(R^{13B})(R^{14B})-$. Here, $R^{12B}$ to $R^{14B}$ each independently represent a hydrogen atom or a substituent.

The compound represented by General Formula (B-II) is a compound represented by General Formula (B-I) disclosed in JP2013-127058A, and $R^{1B}$ to $R^{14B}$, $X^{1B}$, $X^{2B}$, and $L^{1B}$ can be replaced with corresponding $R^1$ to $R^{14}$, $X^1$, $X^2$, and L. After replacing those, the description in paragraphs 0094 to 0116 of JP2013-127058A can be preferably incorporated in this specification.

In the same manner as in the description of JP2013-127058A, the exemplified compounds 1 to 31 disclosed in the paragraphs 0112 to 0115 are preferable compounds in the invention.

The content of the compound represent by General Formula (B-I) or (B-II) in the polarizing plate protective film is not particularly limited, and is preferably 2 to 20 parts by mass and more preferably 5 to 15 parts by mass with respect to 100 parts by mass of the resin configuring the polarizing plate protective film.

(Phthalate Ester Oligomer-Based Additive)

It is also preferable that a compound represented by the following General Formula (E) is used in the polarizing plate protective film of the invention. The compound represented by General Formula (E) is preferable, from a viewpoint of an effect of increasing hardness of a film or an effect of preventing performance deterioration of a polarizer due to wet heat.

The compound is particularly preferable in a case where the resin configuring the polarizing plate protective film is cellulose acylate.

General Formula (E)

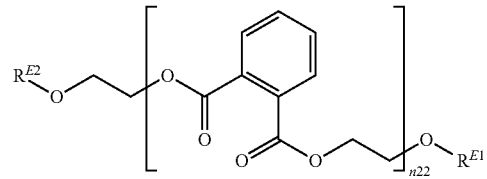

In General Formula (E), $R^{E1}$ and $R^{E2}$ each independently represent a hydrogen atom, an alkyl group, a cycloalkyl group, an aryl group, or an acyl group. N22 represents a number equal to or greater than 2.

The alkyl group, the cycloalkyl group, and the aryl group are identical to the alkyl group, the cycloalkyl group, and the aryl group of $R^{41}$ and $R^{43}$ of General Formula (A) and preferred ranges are also the same as each other.

The acyl group represents a formyl group, an alkylcarbonyl group, an alkenylcarbonyl group, a cycloalkylcarbonyl group, an arylcarbonyl group, and a heterocyclic carbonyl group, the number of carbon atoms of the alkylcarbonyl group is preferably 2 to 20, the number of carbon atoms of the alkenylcarbonyl group is preferably 3 to 20, the number of carbon atoms of the cycloalkylcarbonyl group is preferably 4 to 20, the number of carbon atoms of the arylcarbonyl group is preferably 7 to 20, and the number of carbon atoms of the heterocyclic carbonyl group is preferably 1 to 20.

Examples of these groups include acetyl, propionyl, pivaloyl, myristoyl, acryloyl, methacryloyl, cyclopropylcarbonyl, cyclopentylcarbonyl, cyclohexylcarbonyl, benzoyl, naphthoyl, and nicotinoyl.

$R^{E1}$ and $R^{E2}$ are preferably an acyl group and more preferably an alkylcarbonyl group.

n22 represents the number equal to or greater than 2, and is preferably the number of 2 to 15, more preferably 2 to 10, even more preferably the number of 3 to 10, and still more preferably the number of 3 to 8. In a case of showing a mixture formed of compounds in which n22s are different from each other, n22s are not normal integers and are the numbers with a decimal point.

Hereinafter, specific examples of the compound represented by General Formula (E) are shown, but the invention is not limited thereto.

E-1
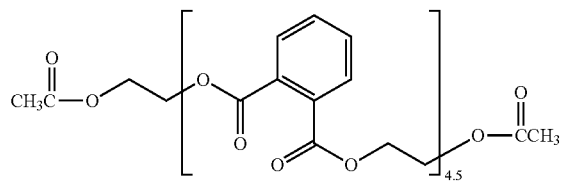

E-2
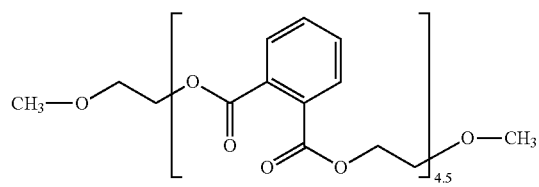

E-3
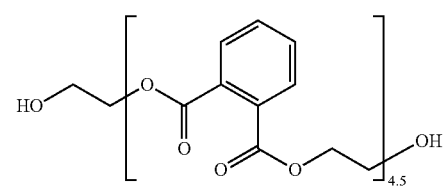

E-4
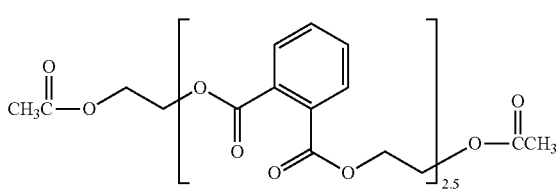

E-5
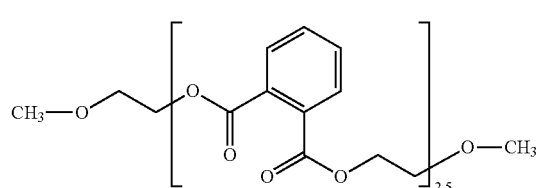

E-6
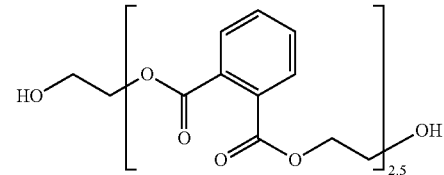

E-7
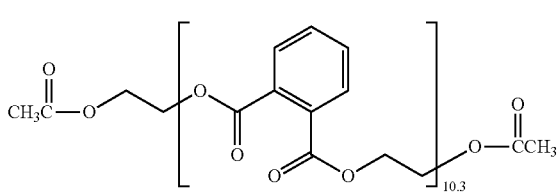

E-8
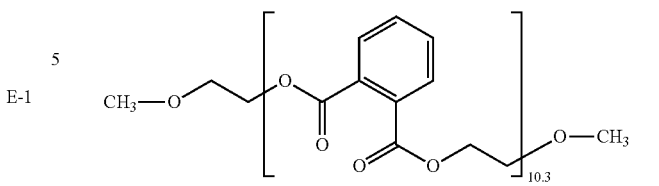

E-9

E-10
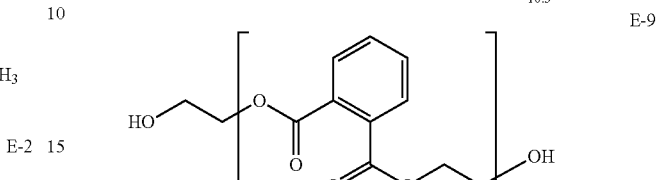

E-11

E-12
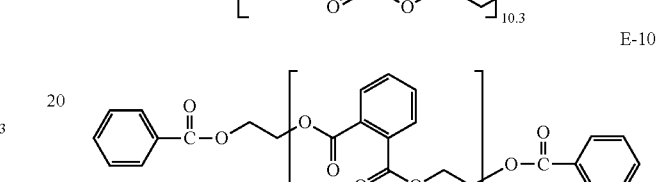

E-13
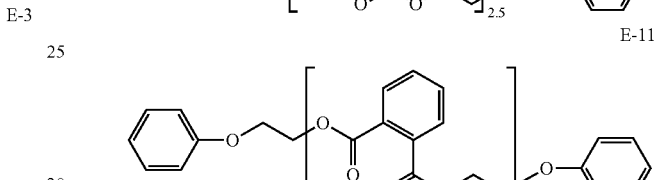

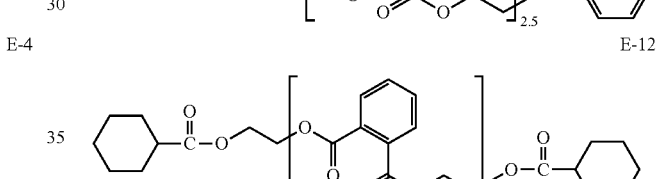

The content of the compound represented by General Formula (E) in the polarizing plate protective film is not particularly limited, and is preferably 2 to 20 parts by mass and more preferably 5 to 15 parts by mass with respect to 100 parts by mass of the resin configuring the polarizing plate protective film.

<Manufacturing Method of Polarizing Plate Protective Film>

The polarizing plate protective film of the invention can be manufactured by a solution casting film-forming method.

Hereinafter, as the manufacturing method of the polarizing plate protective film, an aspect of using cellulose acylate as a resin of a main component will be described as an example, but it is also possible to similarly manufacture the polarizing plate protective film, even in a case of using other resins.

In the solution casting film-forming method, a film is manufactured by using a solution (dope) obtained by dissolving cellulose acylate in an organic solvent.

As the organic solvent, it is preferable to include a solvent selected from ether having 3 to 12 carbon atoms, ketone having 3 to 12 carbon atoms, ester having 3 to 12 carbon atoms, and halogenated hydrocarbon having 1 to 6 carbon atoms.

These ether, ketone, and ester may have a cyclic structure. In addition, a compound including two or more of functional groups (that is, —O—, —CO—, and —COO—) included in ether, ketone, and ester can also be used as the organic solvent.

The organic solvent may include other functional groups such as an alcoholic hydroxyl group. In a case of the organic solvent including two or more kinds of functional groups, the number of carbon atoms is preferably 1 to 12 and more preferably 3 to 12.

It is preferable to perform the preparation so that the amount of cellulose acylate in a cellulose acylate solvent is 10 to 40 mass % in the obtained solution. The amount of cellulose acylate is more preferably 10 to 30 mass %. In the organic solvent (main solvent), arbitrary additives which will be described later may be added.

A drying method of the solution casting film-forming method is disclosed in U.S. Pat. Nos. 2,336,310B, 2,367,603B, 2,492,078B, 2,492,977B, 2,492,978B, 2,607,704B, 2,739,069B, 2,739,070B, GB640731 B and GB736892B, and JP1970-4554B (JP-S45-4554B), JP1974-5614B (JP-S49-5614B), JP1985-176834B (JP-S60-176834B), JP1985-203430B (JP-S60-203430B), and JP1987-115035B (JP-S62-115035B). The drying on a band or a drum can be performed by blowing air or inert gas such as nitrogen.

The casting of two or more layers of the cellulose acylate is performed by using the prepared cellulose acylate solution (dope) to form a film. In this case, it is preferable that a cellulose acylate film is manufactured by the solution casting film-forming method. It is preferable that the dope is casted on a drum or a band, the solvent is evaporated to form a film. The concentration of the dope before casting is preferably adjusted so that the solid content amount is in a range of 10 to 40 mass %. The surface of the drum or the band is preferably finished in a mirror plane state.

In a case of performing casting of a plurality of cellulose acylate solutions having two or more layers, the plurality of cellulose acylate solutions can be casted, the cellulose acylate solutions may be casted from a plurality of casting outlets provided at intervals in a travel direction of a support, and a film may be manufactured while laminating the solutions. These operation can be performed, for example, by using methods disclosed in JP1986-158414A (JP-S61-158414A), JP1989-122419A (JP-H01-122419A), and JP1999-198285A (JP-H11-198285A). In addition, a film can also be formed even by performing casting of the cellulose acylate solution from two casting outlets. This operation can be performed, for example, by using methods disclosed in JP1985-27562B (JP-S60-27562B), JP1986-94724A (JP-S61-94724A), JP1986-947245A (JP-S61-947245A), JP1986-104813A (JP-S61-104813A), JP1986-158413A (JP-S61-158413A), and JP1994-134933A (JP-H06-134933). Further, a cast flowing method of a cellulose acylate film of surrounding a flow of a cellulose acylate solution having high viscosity with a cellulose acylate solution having low viscosity, and extruding the cellulose acylate solutions having high viscosity and low viscosity at the same time, disclosed in JP1981-162617A (JP-S56-162617A) can also be used.

In addition, a film can also be manufactured by using two casting outlets, by stripping a film formed on a support by using a first casting outlet and performing second casting on a side adjacent to the support surface. For example, a method disclosed in JP1969-20235B (JP-S44-20235B) can be used.

Regarding the cellulose acylate solution to be casted, the same solution may be used or two or more kinds of different cellulose acylate solutions may be used. In order to impart a function to a plurality of cellulose acylate layer, the cellulose acylate solution corresponding to the function may be extruded from each casting outlet. In addition, the casting of the cellulose acylate solution of the invention can also be performed at the same time as that of other functional layers (for example, an adhesive layer, a dye layer, an antistatic layer, an antihalation layer, an ultraviolet absorbing layer, or a polarizing layer).

(Adding of Additives)

The timing to add additives such as the compound represented by General Formula (I) to the cellulose acylate solution which is an example of a resin raw material of the polarizing plate protective film is not particularly limited, as long as the additive is added at the time of preparing a film. For example, the additive may be added at the time of synthesis of cellulose acylate or may be mixed with cellulose acylate at the time of preparing the dope.

A step from the casting to the post-drying may be performed under an air atmosphere or may be performed under an inert gas atmosphere such as nitrogen gas. A wind-up machine used for manufacturing the polarizing plate protective film of the invention may be a machine generally used, and the winding-up can be performed by a winding-up method such as a constant tension method, a constant torque method, a taper tension method, an internal stress constant program tension controlling method.

(Stretching Process)

Regarding the polarizing plate protective film of the invention, a stretching process can also be performed. It is possible to apply a desired retardation to the polarizing plate protective film by the stretching process. As a stretching direction of the cellulose acylate film, both of a width direction and a longitudinal direction are preferable.

A method of performing the stretching in the width direction is, for example, disclosed in JP1987-115035A (JP-S62-115035A), JP1992-152125A (JP-H04-152125A), JP1992-284211A (JP-H04-284211A), JP1992-298310A (JP-H04-298310A), and JP1999-4827 IA (JP-H11-48271A).

The stretching of the film is performed under the heating condition. The film can be stretching in the process during drying, and is particularly effectively extended, in a case where a solvent remains. In a case of performing the stretching in the longitudinal direction, the film is stretched, when a speed of a transportation roller of the film is adjusted to set a winding-up speed of the film to be faster than a stripping speed of the film. In a case of the stretching in the longitudinal direction, a film can be stretched by performing the transportation is performed while holding a width of the film by a tenter and slowly widening the width of the tenter. After drying the film, the film can also be stretched can also be performed by using a stretching machine (preferably uniaxial stretching using a long stretching machine).

(Saponification Treatment)

A polarizing plate protective film or the laminate thereof is subjected to alkali saponification treatment, and thus, it is possible to apply adhesiveness with a material of a polarizer such as PVA and the obtained film can be used as a polarizing plate protective film.

As a method of saponification, a method disclosed in paragraphs 0211 and 0212 of JP2007-86748A can be used.

For example, it is preferable that the alkali saponification treatment with respect to the polarizing plate protective film or the laminate thereof is performed with a cycle of dipping the film surface in an alkali solution, performing neutralizing with an acid solution, and washing the film surface with water and drying the film surface. Examples of the alkali solution include a potassium hydroxide solution, and a sodium hydroxide solution. The concentration of hydroxide ions is preferably in a range of 0.1 to 5.0 mol/L and more preferably in a range of 0.5 to 4.0 mol/L. The temperature of the alkali solution is preferably in a range of room temperature to 90° C. and more preferably in a range of 40° C. to 70° C.

Instead of the alkali saponification treatment, an easy adhesion process disclosed in JP1994-94915A (JP-H06-94915A) and JP1994-118232A (JP-H06-118232A) may be performed.

[Film Thickness of Polarizing Plate Protective Film]

The film thickness of a resin film which is the polarizing plate protective film of the invention is preferably 1 μm to 40 μm, more preferably 1 μm to 30 μm, and even more preferably 3 μm to 25 μm.

When the film thickness of the polarizing plate protective film is 1 μm to 40 μm, it is possible to stably transport the film or the polarizing plate in the transportation step at the time of manufacturing a film and manufacturing a polarizing plate.

In addition, in the invention, in a case where the film thickness is small as described above, it is possible to effectively exhibit the effects of the invention.

<<Functional Layer>>

In the polarizing plate protective film of the invention, a functional layer suitable for the purpose can be provided on the polarizing plate protective film, if necessary.

Examples of the functional layer include a hard coat layer, an antireflection layer, a light scattering layer, an antifouling layer, an antistatic layer, an adhesive layer, a dye layer, an antihalation layer, an antiglare layer, a gas barrier layer, an antireflection layer, a sliding layer, an ultraviolet absorbing layer, and a polarizing layer, and these may have a plurality of functions as one layer.

As an example, the hard coat layer is a layer for applying hardness or scratch resistance to the polarizing plate protective film. For example, when a coating composition is coated and hardened on the polarizing plate protective film, it is possible to form a hard coat layer having high adhesiveness with the polarizing plate protective film, particularly, the cellulose acylate film, together with the compound represented by General Formula (I). By adding a filler or additives to the hard coat layer, it is also possible to apply physical ability such as mechanical, electrical, or optical ability or chemical ability such as water repellency or oil repellency to the hard coat layer. The thickness of the hard coat layer is preferably 0.1 to 6 μm and more preferably 3 to 6 μm. When the hard coat layer having a small thickness in such a range is obtained, a polarizing plate protective film including a hard coat layer in which physical properties such as brittleness or curl prevention are improved, the weight is decreased, and the manufacturing cost is reduced, is obtained.

The hard coat layer is preferably formed by hardening a curable composition. The curable composition is preferably prepared as a liquid coating composition. As an example of the coating composition, a monomer or an oligomer for matrix formation binder, polymers, and organic solvents are included. It is possible to form the hard coat layer by coating and hardening the coating composition. In the hardening, a crosslinking reaction or a polymerization reaction can be used.

<Properties of Polarizing Plate Protective Film>

It is necessary that the polarizing plate protective film has low water vapor permeability, high hardness such as knoop hardness or pencil hardness, and low ultraviolet transmittance and haze.

(Water Vapor Permeability)

Water vapor permeability of the polarizing plate protective film of the invention at 40° C. and relative humidity of 90% for 24 hours is preferably equal to or smaller than 1,050 g/m$^2$ and more preferably equal to or smaller than 990 g/m$^2$. By setting the water vapor permeability in the range described above, it is possible to reduce deterioration of polarization performance of the polarizing plate of the polarizing plate protective film of the invention in a high temperature and high humidity environment.

The value of the water vapor permeability in this specification is a value obtained by measuring mass (g) of water vapor passing through a sample for 24 hours in an atmosphere of the temperature of 40° C. and relative humidity of 90% and converting the mass into a value per a sample area 1 m$^2$, based on water vapor permeability test (cup method) of JIS Z0208.

(Hardness)

(1) Knoop Hardness

In the polarizing plate protective film of the invention, surface hardness measured with an indentation load of 50 mN by using a knop indenter is preferably equal to or greater than 185 N/mm$^2$. More preferably, a minimum value of knoop hardness measured by rotating a knoop indenter in the same indentation position with an indentation load of 50 mN based on the method of JIS Z2251 is equal to or greater than 210 N/mm$^2$. The surface hardness (knoop hardness) is measured by a nanoindentation method. In addition, JIS Z 2251 is the Japanese Industrial Standards which was regulated based on ISO4545. For example, the minimum value of knoop hardness of the total 18 orientations measured by rotating the knoop indenter by 10° C. at the same indentation position is equal to or greater than 210 N/mm$^2$. The surface hardness of the polarizing plate protective film is preferably equal to or greater than 220 N/mm$^2$ and more preferably equal to or greater than 230 N/mm$^2$.

The surface hardness of the polarizing plate protective film can be adjusted by types and added amounts of the additives, a degree of polymerization of the resin, a dope solvent composition, and stretching process of the film.

(2) Pencil Hardness

The polarizing plate protective film of the invention preferably has high pencil hardness.

The pencil hardness is measured based on evaluation of pencil hardness of JIS K 5400. Specifically, the humidity of the polarizing plate protective film is controlled at a temperature of 25° C. and relative humidity of 60% for 2 hours, and then evaluation with a load of 500 g is repeated 20 times by using a 3H test pencil regulated based on JIS S 6006, and the evaluation thereof is performed.

Practically, a result of 3H or higher is necessary.

(Ultraviolet Ray Transmittance)

It is preferable that the polarizing plate protective film of the invention has high ability of shielding ultraviolet rays, for prevention deterioration of the polarizer due to ultraviolet rays or driving liquid crystals in the liquid crystal cells. Accordingly, the ultraviolet ray transmittance in a wavelength range of 290 to 300 nm is preferably equal to or smaller than 10% and more preferably equal to or smaller than 5%. When the ultraviolet ray transmittance in a wavelength range of 290 to 300 nm is equal to or smaller than 10%, light excitation such as $I_3^-$ having absorption maximum in the vicinity of the wavelength range of 290 to 300 nm is prevented, and thus, it is possible to effectively prevent deterioration of polarization performance due to light.

(Haze)

The haze of the polarizing plate protective film of the invention is preferably 0.01% to 1.00%. The haze thereof is more preferably 0.05% to 0.80%. It is preferable that the haze is equal to or smaller than 1.00%, because the contrast of a liquid crystal display device is increased.

The haze can be acquired by performing the measurement according to JIS K-7136 by using a haze meter, for example, a haze meter (HGM-2DP, manufactured by Suga Test Instruments Co., Ltd.).

The size of the polarizing plate protective film or the laminate thereof for the measurement is set as 40 mm×80 mm, and the measurement is performed under the condition of the temperature of 25° C. and relative humidity of 60%.

<<Polarizing Plate>>

The polarizing plate of the invention includes a polarizer, and at least one polarizing plate protective film of the invention.

In the polarizing plate of the invention, it is preferable that a polarizer, and at least one polarizing plate protective film of the invention disposed only on one side of the polarizer are disposed. Generally, a polarizing plate in which the polarizing plate protective films are disposed on both surfaces of the polarizer to protect both surfaces is widely used.

In a case of including the polarizing plate protective films on both sides of the polarizer, a polarizing plate protective film on a side opposite to the surface of the polarizing plate protective film of the invention may be a polarizing plate protective film which is different from the polarizing plate protective film of the invention, and an arbitrary polarizing plate protective film may be used.

For example, as the polarizing plate protective film which is different from the polarizing plate protective film of the invention, a polarizing plate protective film having different additives included, types, and contents, or a polarizing plate protective film having different characteristics, or a polarizing plate protective film including or not including a functional layer or a different functional layer is used.

<Retardation Film>

It is preferable that the polarizing plate of the invention includes a retardation film in which an in-plane retardation ($Re_{590}$) at a wavelength of 590 nm in the environment of a temperature of 25° C. and relative humidity of 60% is −5 to 5 nm and retardation in a thickness direction ($Rth_{590}$) is −30 to 30 nm, on the surface opposite to the surface of the polarizing plate protective film of the invention. According to such a configuration, the effects of the invention are more effectively exhibited, when the polarizing plate is incorporated in a liquid crystal display device for an in-place-switching (IPS) mode. The $Res_{590}$ is preferably in a range of 0 to 3 nm and more preferably in a range of 0 to 2 nm. In addition, the $Rth_{590}$ is preferably in a range of −20 to 20 nm and more preferably in a range of −10 to 10 nm.

As such a retardation film, a film disclosed in paragraphs 0066 to 0068 of JP2014-41371A is used.

In addition, a retardation film having optical compensation ability considering a liquid crystal cell driving mode or retardation even in other driving modes may be used.

In this specification, $Re(\lambda)$ and $Rth(\lambda)$ respectively represent an in-plane retardation and retardation in a thickness direction at a wavelength $\lambda$. $Re(\lambda)$ is measured by emitting light at a wavelength $\lambda$ nm in the film normal direction using KOBRA 21ADH or WR (manufactured by Oji Scientific Instruments Co., Ltd.). In the selection of a measurement wavelength of $\lambda$ nm, the measurement can be performed by exchanging a wavelength selective filter manually or changing a measurement value with a program or the like. In a case where the film to be measured is a film shown with a uniaxial or biaxial index ellipsoid, $Rth(\lambda)$ is calculated by the following method.

Regarding $Rth(\lambda)$, total 6 points of $Re(\lambda)$ described above are measured by emitting light at a wavelength of $\lambda$ nm in tilted directions in 10-degree steps from the normal direction to a portion of 50° of one side, regarding a film normal direction using an in-plane slow axis (defined by KOBRA 21ADH or WR) as a tilt axis (rotation axis) (in a case of not including a slow axis, an arbitrary direction of the film in-plane is set as a rotation axis). The calculation by KOBRA 21ADH or WR is performed based on the retardation values measured as described above, an assumed value of an average refractive index, and the input film thickness value. As described above, in a case of a film having a direction in which a value of retardation becomes zero at a certain tilt angle from the normal direction by using an in-plane slow axis as a rotation axis, the retardation value at a tilt angle larger than the tilt angle described above is calculated by KOBRA 21ADH or WR after changing the sign into a negative sign. A retardation value is measured in two directions arbitrarily tilted by using a slow axis as a tilt axis (rotation axis) (in a case of not including a slow axis, an arbitrary direction of the film in-plane is set as a rotation axis), Re and Rth can also be calculated by the following Expression (A) and Expression (β) based on the value, an assumed value of an average refractive index, and the input film thickness value.

$$Re(\theta) = \left[ nx - \frac{ny \times nz}{\sqrt{\left(ny \sin\left(\sin^{-1}\left(\frac{\sin(-\theta)}{nx}\right)\right)\right)^2 + \left(nz \cos\left(\sin^{-1}\left(\frac{\sin(-\theta)}{nx}\right)\right)\right)^2}} \right] \times \frac{d}{\cos\left(\sin^{-1}\left(\frac{\sin(-\theta)}{nx}\right)\right)} \quad \text{Expression (A)}$$

The $Re(\theta)$ represents a retardation value in a direction tilted from the normal direction by an angle $\theta$. In addition, nx of Expression (A) represents a refractive index in a slow axis direction in the plane, ny represents a refractive index in a direction orthogonal to that of nx in the plane, and nz represents a refractive index in a direction orthogonal to that of nx and ny.

$$Rth = ((nx+ny)/2 - nz) \times d \quad \text{Expression (β)}$$

In a case where the film to be measured is a film which cannot be represented as a uniaxial or biaxial index ellipsoid, a so-called film without an optic axis, $Rth(\lambda)$ is calculated by the following method. Regarding $Rth(\lambda)$, total 11 points of $Re(\lambda)$ described above are measured by emitting light at a wavelength of $\lambda$ nm in tilted directions in 10° steps from −50° to +50°, regarding the film normal direction using an in-plane slow axis (defined by KOBRA 21ADH or WR) as a tilt axis (rotation axis). The calculation by KOBRA 21ADH or WR is performed based on the retardation values measured as described above, an assumed value of an average refractive index, and the input film thickness value.

In the measurement described above, as the assumed value of the average refractive index, values in Polymer Handbook (JOHN WILEY & SONS, INC) or catalogues of various film can be used. When the value of the average refractive index is not known, the measurement can be performed by the Abbe refractometer. The values of the average refractive index of the main retardation film are as follows: cellulose acylate (1.48), cycloolefin polymer (1.52), polycarbonate (1.59), polymethyl methacrylate (1.49), polystyrene (1.59). By inputting these assumed values of the average refractive index and the film thickness, nx, ny, and nz are calculated by KOBRA 21ADH or WR. The value of Nz=(nx−nz)/(nx−ny) is further calculated with the calculated nx, ny, and nz.

The measurement wavelength of Re and Rth is a value of λ=590 nm in a visible light region, unless otherwise noted.

<Polarizer>

The polarizer is formed of at least a dichromic dye and a resin.

(Resin)

In the polarizer of the invention, a polyvinyl alcohol-based resin is preferably used. The polarizer of the invention includes a polyvinyl alcohol-based resin as a main component, and generally the polyvinyl alcohol-based resin occupies 80 mass % or more of the polarizer. Polyvinyl alcohol is normally a component obtained by saponification of polyvinyl acetate, but for example, a component capable of copolymerizing with vinyl acetate, such as unsaturated carboxylic acid, unsaturated sulfonic acid, olefins, and vinyl ethers may be included. In addition, a modified polyvinyl alcohol-based resin including an acetoacetyl group, a sulfo group, a carboxy group, or an oxyalkylene group can also be used.

A degree of saponification of the polyvinyl alcohol-based resin is not particularly limited, and is preferably 80 to 100 mol %, and particularly 90 to 100 mol %, from a viewpoint of solubility. In addition, a polymerization degree of the polyvinyl alcohol-based resin is not particularly limited, and is preferably 1,000 to 10,000 and more preferably 1,500 to 5,000.

A modulus of elasticity of the polyvinyl alcohol-based resin film before being stretched is preferably 0.1 MPa to 500 MPa and more preferably 1 MPa to 100 MPa, in terms of a Young's modulus.

By setting the modulus of elasticity in the range described above, it is possible to prepare a polyvinyl alcohol-based resin film having an excellent effect of wrinkle generation prevention after being stretched and sufficient hardness.

The thickness of the polyvinyl alcohol-based resin film before being stretched is not particularly limited, and is preferably 1 µm to 1 mm and particularly preferably 20 to 200 µm, from viewpoints of stability of film storage and uniform stretching. In addition, the thickness of the polyvinyl alcohol-based resin film after being stretched is preferably 2 to 100 µm and preferably 7 to 25 µm, in a viewpoint of improvement of light leakage. With this thickness, the thickness of the film of the polarizer is determined.

(Dichromic Dye)

The polarizer of the invention includes a dichromic dye. Here, the dichromic dye means a dye having different absorbency depending on a direction, and examples thereof include iodide ion, a diazo dye, a quinone dye, and other arbitrary dichromic dyes. As the dichromic dye, high-order iodide ion or $I_3^-$ or $I_5^-$ or dichromic dye can be preferably used.

In the invention, a high-order iodide ion is particularly preferably used. The high-order iodide ion can be generated in a state in which polyvinyl alcohol is dipped in a solution obtained by dissolving iodine in a potassium iodide aqueous solution and/or a boric acid aqueous solution, and adsorption or orientation are performed in polyvinyl alcohol, as disclosed in "Application of polarizing plate", written by Ryo Nagata, CMC publishing and industrial materials, Vol. 28, No. 7, p. 39 to p. 45.

The content of the dichromic dye is preferably 0.1 to 50 parts by mass, more preferably 0.5 to 20 parts by mass, and even more preferably 1.0 to 5.0 parts by mass with respect to the content of the polyvinyl alcohol-based resin.

The polarizer of the invention may include a plasticizer and a surfactant, if necessary, in addition to the polyvinyl alcohol-based resin and the dichromic dye.

<Manufacturing Method of Polarizer>

As a manufacturing method of the polarizer of the invention, for example, a method of configuring a polarizer by forming a film of a polyvinyl alcohol-based resin and introducing iodine thereto is used. The manufacturing of the polyvinyl alcohol-based resin can be performed with reference to a method disclosed in paragraphs 0213 to 0237 of JP2007-86748A, JP3342516B, JP1997-328593A (JP-H09-328593A), JP2001-302817A, and JP2002-144401A.

In the invention, particularly, the method preferably includes a step of preparing a film of a polyvinyl alcohol-based resin solution including a polyvinyl alcohol-based resin, a step of stretching a polyvinyl alcohol-based resin film, a step of dyeing the polyvinyl alcohol-based resin film after being stretched, with a dichromic dye, and a step of crosslinking the dyed polyvinyl alcohol-based resin film by boric acid.

In the step of preparing a film of a polyvinyl alcohol-based resin solution, it is preferable that a polyvinyl alcohol-based resin is added to water while stirring, and a raw solution obtained by dissolving the polyvinyl alcohol-based resin in water or an organic solvent is prepared. The concentration of the polyvinyl alcohol-based resin in the raw solution is preferably 5 to 20 mass %. In addition, the obtained slurry may be dehydrated to prepare a wet cake of the polyvinyl alcohol-based resin having the moisture content of approximately 40%. In a case of further adding additives after that, a method of inputting the wet cake of polyvinyl alcohol in a dissolver, adding a plasticizer and water, and stirring the mixture while blowing water vapor from the bottom is preferable, for example. The inner resin temperature is preferably heated to 50° C. to 150° C. and the inner portion of the system may be pressurized.

In the invention, a method of casting the raw solution of the polyvinyl alcohol-based resin solution prepared as described above to form a film is generally preferably used. The method of casting is not particularly limited, and a method of supplying the heated raw solution of the polyvinyl alcohol-based resin solution to a dual axial extruder and casting the raw solution on a support from discharge means (preferably, a die, and more preferably a T-shaped slit die) by a gear pump is preferable. In addition, the temperature of the resin solution discharged from the die is not particularly limited.

As the support, a cast drum is preferable, and a diameter, a width, a rotation rate, and a surface temperature of the drum are not particularly limited. Among these, the diameter of the cast drum is preferably 2,000 to 5,000 mm, more preferably 2,500 to 4,500 mm, and particularly preferably 3,000 to 3,500 mm.

The width of the cast drum is preferably 2 to 6 m, more preferably 3 to 5 m, and particularly preferably 4 to 5 m.

The rotation rate of the cast drum is preferably 2 to 20 m/min, more preferably 4 to 12 m/min, and particularly preferably 5 to 10 m/min.

The cast drum surface temperature of the cast drum is preferably 40° C. to 140° C., more preferably 60° C. to 120° C., and particularly preferably 80° C. to 100° C.

The resin temperature of the T-shaped slit die outlet is preferably 40° C. to 140° C., more preferably 60° C. to 120° C., and particularly preferably 80° C. to 100° C.

After that, it is preferable that a rear surface and a front surface of the obtained roll are dried while passing through a drying roll. A diameter, a width, a rotation rate, and a surface temperature of the drying roll are not particularly limited. Among these, the diameter of the cast drum is preferably 200 to 450 mm, more preferably 250 to 400 mm, and particularly preferable 300 to 350 mm.

A length of the obtained film is not particularly limited, and an elongated film having a length equal to or greater than 2,000 m, preferably equal to or greater than 4,000 m can be obtained. A width of the obtained film is not particularly limited, either, and is preferably 2 to 6 m and more preferably 3 to 5 m.

After forming a film of the polyvinyl alcohol-based resin solution, the film is stretched. In the stretching, vertical uniaxial stretching method as disclosed in U.S. Pat. No. 2,454,515B or a tenter method as disclosed in JP2002-86554A can be preferably used. A preferred stretching ratio is 2 times to 12 times, and more preferably 3 times to 10 times. It is also preferable that a relationship between the stretching ratio, the original thickness, and the thickness of the polarizer is set to satisfy a relationship of (film thickness of the polarizer after bonding the polarizing plate protective film/original film thickness)×(total stretching ratio)>0.17 disclosed in JP2002-040256, or a relationship between a width of the polarizer when being extracted from a final bath and the width of the polarizer at the time of the bonding of the polarizing plate protective film is set to satisfy a relationship of 0.80≤(width of the polarizer at the time of the bonding of the polarizing plate protective film/width of the polarizer when being extracted from a final bath)≤0.95 disclosed in JP2002-040247A.

After the stretching, the polyvinyl alcohol-based resin film is dyed with the dichromic dye. The dyeing is performed by air phase or liquid phase adsorption. By using a case of performing by the liquid phase as an example, in a case of using iodine as the dichromic dye, the dyeing is performed by dipping a polymer film for a polarizer in an aqueous solution of iodine-potassium iodide. The mass of iodine is 0.1 to 20 g/l, the mass of potassium iodide is 1 to 200 g/l, and the mass ratio of iodine and potassium iodide is preferably 1 to 200. The dyeing time is preferably 10 to 5,000 seconds and the liquid temperature is preferably 5° C. to 60° C. As the dyeing method, not only the dipping is used, but also arbitrary means such as coating or spraying of iodine or a dye solution can also be used. The dyeing step may be performed before or after the stretching step of the invention, and it is particularly preferable that the dyeing is performed by the liquid phase before the stretching step, because the film is suitably swelled and easily stretched.

In addition, in the dyeing, a method disclosed in JP2002-86554A can be used. As the dyeing method, not only the dipping is used, but also arbitrary means such as coating or spraying of iodine or a dye solution can also be used. As disclosed in JP2002-290025A, a concentration of iodine, a dyeing bath temperature, a stretching ratio in the bath, and a method of dyeing a bath solution in the bath while stirring may be used.

As disclosed in JP3145747B, a boron-based compound such as boric acid or borax may be added into a dyed solution.

As other steps, a swelling step, a film hardening step, and a drying step may be performed. These steps are disclosed in paragraphs 0039 to 0050 of JP2011-237580 and the contents thereof are incorporated here.

<Shape and Configuration>

A shape of the polarizing plate of the invention includes a shape of a polarizing plate which is manufactured to have an elongated shape and is wound up in a roll shape (for example, aspect in which a roll length is equal to or greater than 2,500 m or equal to or greater than 3,900 m) due to continuous production, in addition to a shape of a polarizing plate having an aspect of a film piece which is cut in a size capable of being incorporated into a display device. In order to be used for a large-screen liquid crystal display device, a width of the polarizing plate is preferably equal to or greater than 1,470 mm.

The polarizing plate of the invention is configured with a polarizer and at least one polarizing plate protective film of the invention, and is also preferably configured by bonding a protection film (different from the polarizing plate protective film of the invention) to one surface of the polarizing plate and bonding a separate film to the surface opposite thereto.

The protection film and the separate film are used for protecting the polarizing plate at the time of delivery of the polarizing plate or inspection of products. In this case, the protection film is bonded for protecting the surface of the polarizing plate, and is used on the surface side opposite to the surface of the polarizing plate bonded to a liquid crystal plate. In addition, the separate film is used for covering an adhesive layer bonded to the liquid crystal plate, and is used on the side of the surface of the polarizing plate bonded to the liquid crystal plate.

<Laminating Method of Polarizer and Polarizing Plate Protective Film>

In the manufacturing method of the polarizing plate of the invention, at least one polarizing plate protective film of the invention is laminated on at least one surface of the polarizer obtained as described above.

In the manufacturing method of the polarizing plate of the invention, the polarizing plate is preferably manufactured by a method of performing alkali treatment with respect to a surface of the polarizing plate protective film and bonding the polarizing plate protective film to at least one surface, preferably both surfaces of a polarizer which is manufactured by dipping and stretching a PVA film in a iodine solution, by using a completed saponified polyvinyl alcohol aqueous solution.

Examples of an adhesive used for bonding the treated surface of the polarizing plate protective film and the polarizer to each other include a polyvinyl alcohol-based adhesive such as PVA or polyvinyl butyral or a vinyl-based latex such as butyl acrylate.

When bonding the polarizing plate protective film of the invention to the polarizer, it is preferable to perform the bonding so that a transmission axis of the polarizer and a slow axis of the polarizing plate protective film are orthogonal or parallel to each other or forms 45°.

Here, the parallel and orthogonal states include a range of errors allowed in the technical field of the invention. This means that the error is in a range within less than ±100 from an exact angle relating to the parallel and orthogonal states and the error from the exact angle is preferably equal to or smaller than 5° and more preferably equal to or smaller than 3°.

The state in which the transmission axis of the polarizer and the slow axis of the polarizing plate protective film are parallel to each other means that a direction of the main refractive index nx of the polarizing plate protective film and a direction of the transmission axis of the polarizing plate intersect each other by an angle ±10°. This angle is preferably within 5°, more preferably within 3°, even more preferably within 1°, and most preferably within 0.5°.

In addition, the state in which the transmission axis of the polarizer and the slow axis of the polarizing plate protective film are orthogonal to each other means that a direction of the main refractive index nx of the polarizing plate protective film and a direction of the transmission axis of the polarizing plate intersect each other by an of 90° C.±10°. This angle is preferably 90° C.±5°, more preferably 90° C.±3°, even more preferably 90° C.±1°, and most preferably 90° C.±0.1°. It is preferable that the angle is set in the range described above, because a deterioration in performance of a degree of polarization under a crossed nicols prism of the polarizing plate is prevented and light leakage is decreased.

<Functionalization of Polarizing Plate>

The polarizing plate of the invention is also preferably used as a functionalized polarizing plate by combining with an antireflection layer or a luminance improving layer for improving visibility of a display, or a polarizing plate protective film including a forward scattering layer or an antiglare layer. The antireflection layer and the luminance improving layer, other functional optical films, the forward scattering layer, and the antiglare layer for functionalization are disclosed in paragraphs 0257 to 0276 of JP2007-86748, and a polarizing plate functionalized based on the description can be manufactured.

<Performance of Polarizing Plate>

(Degree of Polarization)

A degree of polarization of the polarizing plate of the invention is preferably equal to or greater than 95.0%, more preferably equal to or greater than 98%, and most preferably equal to or greater than 99.5%.

In the invention, the degree of polarization of the polarizing plate can be acquired by calculating polarization degree spectra by the following expression from an orthogonal transmittance and an average transmittance measured in a wavelength range of 380 nm to 700 nm by using an automatic polarizing film measurement device VAP-7070 manufactured by JASCO Corporation, and calculating a weighting average of a light source (auxiliary illuminant C) and CIE visibility (Y).

Degree of polarization (%)={(average transmittance−orthogonal transmittance)/(average transmittance+orthogonal transmittance)}$^{1/2}$×100

(Change in Degree of Polarization)

The polarizing plate of the invention has excellent durability under the wet heat condition. Accordingly, an amount of a change of the degrees of polarization before and after the test of polarizing sheet durability which will be described later is small.

In the polarizing plate of the invention, the orthogonal transmittance and the average transmittance are measured by using an automatic polarizing film measurement device VAP-7070 manufactured by JASCO Corporation, and the degree of polarization is calculated by the expression described above, and it is particularly preferable that a change in the degree of polarization in a case of the storage in the environment of a temperature of 80° C. and relative humidity of 90% for 144 hours is smaller than 5%.

Two samples (5 cm×5 cm) obtained by bonding the polarizing plate of the invention onto glass through a pressure sensitive adhesive are prepared. At this time, the polarizing plate protective film of the invention is bonded to the glass side. The orthogonal transmittance is measured by setting the glass side of this sample to face a light source. The measurement of the two samples is respectively performed, and an average value thereof is set as the orthogonal transmittance and the average transmittance. Specific description is as shown in examples.

(Crystallization Index of Polyvinyl Alcohol in Polarizer)

In the invention the resin configuring the polarizer is preferably polyvinyl alcohol, and a crystallization index of the polyvinyl alcohol after storing the polarizing plate of the polarizer configured with the polyvinyl alcohol in the environment of a temperature of 80° C. and relative humidity of 90% for 144 hours is preferably equal to or smaller than 0.05.

Here, the crystallization index of the polyvinyl alcohol indicates a degree of crystallization of the polyvinyl alcohol, and in the invention, a method of acquiring the crystallization index by using absorbency at a wave number of 1.141 cm$^{-1}$ which is known as a crystallization band in infrared absorption spectra is used.

In the invention, the calculation is performed from the following expression (α) based on the absorbency at a wave number of 1,134 cm$^{1}$.

crystallization index of polyvinyl alcohol={A(1,141 cm$^{-1}$)−A(1,134 cm$^{-1}$)}/A(1,134 cm$^{-1}$)    Expression (α):

In Expression (α), A(1,141 cm$^{-1}$) represents absorbency at a wave number of 1,141 cm$^{-1}$ and A(1,134 cm$^{-1}$1) represents absorbency at a wave number of 1,134 cm$^{-1}$.

Here, a peak at a wave number of 1,141 cm$^{-1}$ is a skeletal vibration of a carbon zigzag chain extended in the crystallization band of the polyvinyl alcohol, that is, in a crystallization region, and a peak region at a wave number of 1,134 cm$^{-1}$ (base of C—O stretching vibration of a non-crystallized part) is a region based on absorbency with respect to the absorbency of polyvinyl alcohol in the crystallization band.

In the invention, it is assumed that the compound represented by General Formula (I) of the invention in the polarizing plate protective film is diffused and moves to the polarizer in the high temperature and high humidity environment and crystallization of the polyvinyl alcohol is prevented.

Thus, the crystallization index is acquired by measuring the infrared absorption spectra of the surface of the polarizer after storage in the high temperature and high humidity environment, to obtain the effects thereof.

Specifically. ATR-IR spectra are measured by an infrared total reflection spectroscopy measurement method (ATR method) with, for example, an infrared spectroscope capable of FT-IR ATR (for example, Nicolet 6700 manufactured by Thermo Scientific Condition). More specific description is as shown in examples.

(Other Properties)

Other preferred optical properties of the polarizing plate of the invention are disclosed in paragraphs 0238 to 0255 of JP2007-086748A and it is preferable that these properties are satisfied.

<<Display Device>>

The invention is preferably used for a display device including the polarizer.

The invention is applied for preventing reflection in a liquid crystal display device or an organic electroluminescence display device as such a display device.

When the liquid crystal display device is used as an example, the liquid crystal display device of the invention at least includes a liquid crystal cell and the polarizing plate of the invention. The liquid crystal display device has a configuration in which liquid crystal cells are disposed between two polarizing plates as a first polarizing plate and a second polarizing plate. A driving ode of the liquid crystal cell is not particularly limited, and each driving ode such as TN, OCB, VA, or IPS is generally used. In addition, it is preferable to use an optically anisotropic layer which performs optical compensation in accordance with the driving mode of the liquid crystal cell, and the optically anisotropic layer is disposed between the liquid crystal cell and the polarizing plate. The polarizing plate protective film may have the function of the optically anisotropic layer.

FIG. 1 is an example of a schematic view showing an example of the display device of the invention as a liquid crystal display device. In FIG. 1, a liquid crystal display device 10 includes a liquid crystal cell including a liquid crystal layer 5, and an electrode substrate on the liquid crystal cell 3 and an electrode substrate below the liquid crystal cell 6 which are disposed on the upper and lower portions of the liquid crystal layer, and an upper side polarizing plate 1 and a lower side polarizing plate 8 which are disposed on both sides of the liquid crystal cell. A color filter may be disposed between the liquid crystal cell and each polarizing plate. In a case of using the liquid crystal display device 10 as a transmittive type, a backlight including a cold cathode or hot cathode fluorescent tube, or a light emitting diode, a field emission element, or an electroluminescent element as a light source is disposed on a rear surface.

Each of the upper side polarizing plate 1 and the lower side polarizing plate 8 has a configuration in which a polarizer is laminated to be interposed between two polarizing plate protective films, and in the liquid crystal display device 10 of the invention, it is preferable that at least one of the polarizing plates is the polarizing plate of the invention. In the liquid crystal display device 10 of the invention, it is preferable that the polarizing plate protective film of the invention, the polarizer, and a general transparent protective film are laminated in this order from the outer side of the device (side far from the liquid crystal cell).

EXAMPLES

Hereinafter, the invention will be described more specifically based on the examples.

Materials, reagents, amounts of substances and percentages thereof, and operations shown in the following examples can be suitably changed within a range not departing from a gist of the invention. Therefore, the ranges of the invention is not limitedly interpreted by the examples shown below.

[Synthesis of Compound Represented by General Formula (I)]

The compound represented by General Formula (I) of the invention was synthesized as follows.

The synthesis examples of the representative compounds are shown below.

Synthesis Example 1: Synthesis of an Exemplified Compound (D-1-25)

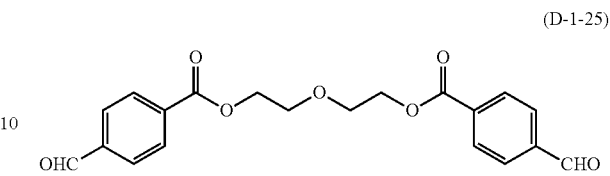

(D-1-25)

16.98 g (113.1 mmol) of terephthalaldehyde acid, 3.0 g (28.27 mmol) of diethylene glycol, 21.68 g (113.1 mmol) of 1-ethyl-3-(3-dimethylaminopropyl)carbodiimide hydrochloride, and 0.69 g (5.7 mmol) of N,N-dimethylaminopyridine were put in a 500 ml three-neck flask, 200 mL of tetrahydrofuran was further added thereto, and the mixture was stirred at room temperature for 1 hour. After that, heating and refluxing were performed for 8 hours. After the reaction, the reaction liquid was cooled to room temperature, ethyl acetate and water were added thereto, and an organic layer was extracted. The organic layer was washed with a sodium bicarbonate aqueous solution twice, dried over magnesium sulfate, and concentrated under reduced pressure. The resultant material is purified by silica gel column chromatography (n-hexane/ethyl acetate=1/1), and accordingly, 7.93 g (yield of 76%) of a desired exemplified compound (D-1-25) was obtained as a white solid.

The structure of the obtained compound was confirmed with $^1$H-NMR.

Spectral Data of $^1$H-NMR of Exemplified Compound (D-1-25)

$^1$H-NMR (300 MHz, CDCl$_3$): δ=10.09 (s, 2H), 8.16 (d, 4H), 7.89 (d, 4H), 4.54 (m, 4H), 3.90 (m, 4H)

Synthesis Examples 2 to 5

Exemplified compounds (D-1-24), (D-1-26), (D-1-27), and (D-1-28) were synthesized in the same manner as in the synthesis example 1, except for changing diethylene glycol used in the synthesis example 1 to the corresponding diol compound.

Synthesis Example 6

Synthesis of Exemplified Compound (D-1-2)

An exemplified compound (D-1-2) was synthesized in the same manner as in the synthesis example 1, by using 4-hydroxybenzaldehyde and terephthalaldehyde acid.

Synthesis Example 7

Synthesis of Exemplified Compound (D-1-14)

An exemplified compound (D-1-14) was synthesized in the same manner as in the synthesis example 1, except for changing diethylene glycol and terephthalaldehyde acid to terephthalic acid and 4-hydroxybenzaldehyde.

Synthesis Example 8

Synthesis of Exemplified Compound (D-1-29)

An exemplified compound (D-1-29) was synthesized in the same manner as in the synthesis example 1, except for changing diethylene glycol and terephthalaldehyde acid to succinic acid and vanillin.

Synthesis Example 9

Synthesis of Exemplified Compound (D-1-32)

An exemplified compound (D-1-32) was synthesized in the same manner as in the synthesis example 1, by using trimethylol propane and terephthalaldehyde acid.

Synthesis Example 10

Synthesis of Exemplified Compound (D-1-34)

An exemplified compound (D-1-34) was synthesized in the same manner as in the synthesis example 1, by using ethylene glycol and 3,4-diformylbenzoic acid.

Synthesis Example 11

Synthesis of Exemplified Compound (D-3-6)

An exemplified compound (D-3-6) was synthesized in the same manner as in the synthesis example 1, by using 5,5-dimethyl-2-(p-hydroxyphenyl)-1,3-dioxane and terephthalaldehyde acid.

Synthesis Example 12

Synthesis of Exemplified Compound (D-3-7)

An exemplified compound (D-3-7) was synthesized in the same manner as in the synthesis example 1, by using carboxybenzylidene dipropionate and 4-hydroxybenzaldehyde.

Synthesis Examples 13 to 16

An exemplified compound (D-1-4) was synthesized by a usual alkyl reaction by using 4-hydroxybenzaldehyde and tetrakis (bromomethyl) methane. An exemplified compound (D-1-12) was synthesized from 4,4'-dicarboxydiphenyl sulfone. An exemplified compound (D-1-31) was synthesized from 1,2-bis (4-formylphenylthio) ethane. In addition, an exemplified compound (D-1-35) was synthesized by a usual Pd coupling reaction by using 4-bromo-3-fluorobenzaldehyde and 2-fluoro-4-formylphenylboronic acid.

Synthesis Example 17

Synthesis of Exemplified Compound (D-3-4)

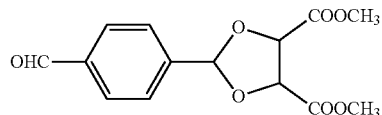

(D-3-4)

10.0 g (74.6 mmol) of terephthalaldehyde, 33.2 g (186.4 mmol) of dimethyltartrate, and 1.42 g (7.5 mmol) of p-toluenesulfonic acid monohydrate were put in a 500 mL three-neck flask, 200 mL of toluene was further added, and the mixture was stirred at 110° C. for 6 hours. Then, heating and refluxing were performed at 110 while removing water with a Dean-Stark apparatus for 4 hours. After the reaction, the reaction liquid was cooled to room temperature and washed with a sodium bicarbonate aqueous solution twice, and an organic layer was washed with saturated saline once, dried over magnesium sulfate, and concentrated under reduced pressure. The resultant material is purified by silica gel column chromatography (n-hexane/ethyl acetate=2/1), and accordingly, 7.93 g (yield of 76%) of a desired exemplified compound (D-3-4) was obtained as a white solid.

The structure of the obtained compound was confirmed with 1H-NMR.

Synthesis Examples 18 and 19

An exemplified compound (D-3-5) was synthesized by acetalization according to the usual method, by using terephthalaldehyde and equivalent amount of 2,2-dimethyl-1,3-propanediol. In addition, an exemplified compound (D-3-12) was synthesized by acetalization according to the usual method, by using 4-formylphenylboronic acid pinacol (manufactured by Tokyo Chemical Industry Co., Ltd.) and pinacol.

All of exemplified compounds (D-1-1), (D-1-5), (D-2-1), and (D-2-2) were commercially available products manufactured by Tokyo Chemical Industry Co., Ltd. and an exemplified compound (D-1-3) was a commercially available product manufactured by Sigma-Aldrich Corporation.

Example 1

As described below, a polarizing plate protective film was manufactured, and a polarizing plate was manufactured by using this polarizing plate protective film.

A. Manufacturing of Polarizing Plate Protective Film (1) Manufacturing of Polarizing Plate Protective Film 101

(Preparation of Cellulose Acylate Solution 101)

The following composition was put in a mixing tank and stirred to dissolve each component, and a cellulose acylate solution 101 was prepared.

Composition of Cellulose Acylate Solution 101

Cellulose acetate having a degree of acetyl substitution of 2.87: 100.0 parts by mass Polarizing sheet durability improving agent (D-1-1): 7.0 parts by mass Methylene chloride (first solvent): 389.0 parts by mass Methanol (second solvent): 58.2 parts by mass Polarizing Sheet Durability Improving Agent (D-1-1)

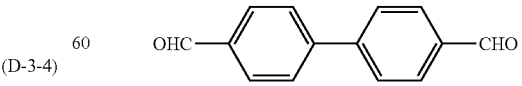

(Preparation of Matting Agent Solution 102)

The following composition was put in a disperser and stirred to dissolve each component, and a matting agent solution 102 was prepared.

Composition of Matting Agent Solution 102
Silica particles having an average particle size of 20 nm (AEROSIL R972 manufactured by Nippon Aerosil co. Ltd.): 2.0 parts by mass
Methylene chloride (first solvent): 75.5 parts by mass
Methanol (second solvent): 11.3 parts by mass
Cellulose acylate solution 101: 0.9 parts by mass <Casting>

1.3 parts by mass of the matting agent solution 102 and 98.7 parts by mass of the cellulose acylate solution 101 were added and mixed with an in-line mixer, and a resin solution (dope) was prepared. The prepared dope was casted on a stainless steel casting support (support temperature of 22° C.) by using a band casting machine. When the amount of solvent remaining in the dope become approximately 20 mass %, a formed film was stripped. Both ends of the stripped film in a width direction were grasped with a tenter, and the film in a state where the amount of remaining solvent is 5 to 10 mass % was stretched 1.10 times (10%) in a width direction at the temperature of 120° C. and dried. Then, the film was transported between the rolls of a thermal treatment device to be further dried, and a polarizing plate protective film 101 of the invention was obtained. A thickness of the polarizing plate protective film 101 obtained was 25 μm, a width was 1,480 nm, and a winding length was 2,700 m.

(2) Manufacturing of Polarizing Plate Protective Films 102 to 110 c01 and c02

Polarizing plate protective films 102 to 110 and comparative polarizing plate protective films c01 and c02 were respectively manufactured in the same manner as in the manufacturing of the polarizing plate protective film 101, except for changing the types and added amount of the polarizing sheet durability improving agent as shown in Table 1 which will be described later.

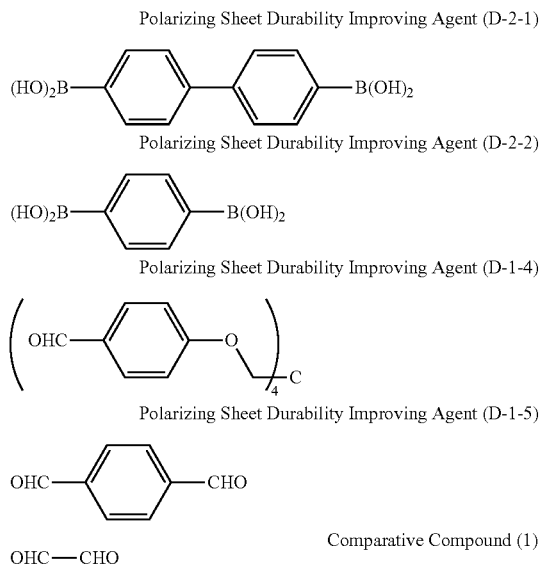

(3) Manufacturing of Cellulose Acylate Film S01 (Preparation of Cellulose Acylate Solution 103)

The following composition was put in a mixing tank and stirred to dissolve each component, and a cellulose acylate solution 103 was prepared.

Composition of Cellulose Acylate Solution 103
Cellulose acetate having a degree of acetyl substitution of 2.87: 100.0 parts by mass Additive E1: 8.0 parts by mass
SEESORB706 (product name) manufactured by Shipro Kasei Kaisha, Ltd.: 4.0 parts by mass
Methylene chloride (first solvent): 389.0 parts by mass
Methanol (second solvent): 58.2 parts by mass Additive E-1

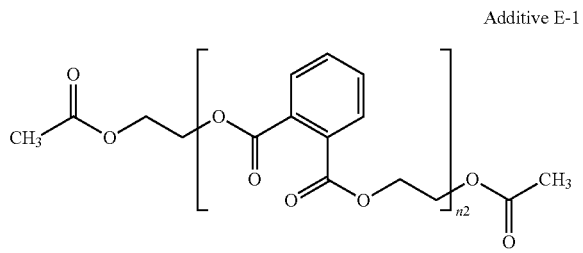

Weight Average Molecular Weight 1,000 n2: approximately 4.5

(Preparation of Matting Agent Solution 104)

The following composition was put in a disperser and stirred to dissolve each component, and a matting agent solution 104 was prepared.

Composition of Matting Agent Solution 104
Silica particles having an average particle size of 20 nm (AEROSIL R972 manufactured by Nippon Aerosil co. Ltd.): 2.0 parts by mass
Methylene chloride (first solvent): 75.5 parts by mass
Methanol (second solvent): 11.3 parts by mass
Cellulose acylate solution 103: 0.9 parts by mass (Preparation of Barbituric Acid-Based Additive Solution 105)

The following composition was put in a mixing tank and stirred while heating to dissolve each component, and a barbituric acid-based additive solution 105 was prepared.

Composition of Barbituric Acid-Based Additive Solution 105
Additive A-3: 20.0 parts by mass
Methylene chloride (first solvent): 69.6 parts by mass
Methanol (second solvent): 10.4 parts by mass Additive A-3

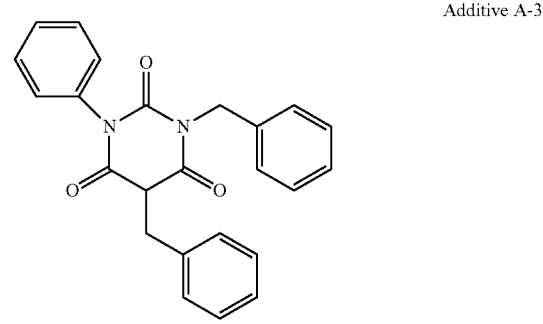 [SMILES: O=C1C(Cc2ccccc2)C(=O)N(c2ccccc2)C(=O)N1Cc1ccccc1]

<Casting>

1.3 parts by mass of the matting agent solution 104, 3.4 parts by mass of the barbituric acid-based additive solution 105 were respectively filtered and mixed with each other with an in-line mixer, 95.3 parts by mass of the cellulose acylate solution 103 was added thereto and mixed with each other with the in-line mixer, and a resin solution (dope) was prepared. The prepared dope was casted on a stainless steel casting support (support temperature of 22° C.) by using a band casting machine. When the amount of solvent remaining in the dope become approximately 20 mass %, a formed film was stripped. Both ends of the stripped film in a width direction were grasped with a tenter, and the film in a state where the amount of remaining solvent is 5 to 10 mass % was stretched 1.15 times (15%) in a width direction at the temperature of 120° C. and dried. Then, the film was transported between the rolls of a thermal treatment device to be further dried, and a cellulose acylate film S01 was obtained. A thickness of the cellulose acylate film S01 obtained was 25 µm, a width was 1,480 nm, and a winding length was 2,700 m.

(4) Manufacturing of Cellulose Acylate Film S02

A cellulose acylate film S02 was manufactured in the same manner as in the preparation of the cellulose acylate film S01, except for not adding the additive A-3.

(5) Manufacturing of Cellulose Acylate Film S03

A cellulose acylate film S03 was manufactured in the same manner as in the preparation of the cellulose acylate film S01, except for changing the additive E-1 to additive B-97.

The additive B-97 is an exemplified compound B-97 described in the section of the additive.

B. Manufacturing of Polarizing Plate

<Manufacturing of Polarizer A>

An aqueous solution obtained by dissolving polyvinyl alcohol (PVA) powder having an average degree of polymerization of 2,400 and a degree of saponification equal to or greater than 99.9% in pure water adjusting concentration as 10 mass %, was applied onto a polyester film, dried at 40° C. for 3 hours, and further dried at 110° C. for 60 minutes, and a PVA film having a thickness of 32 µm was obtained. The obtained film was swelled in warm water at 30° C. for 1 minute, and dipped in an aqueous solution of potassium iodide/iodine (mass ratio 10:1) at 30° C., and vertical uniaxial stretching was performed by 1.5 times. Regarding the concentration of the aqueous solution of potassium iodide/iodine (mass ratio 10:1), the concentration of iodine was 0.38 mass %. Then, vertical uniaxial stretching was performed so that the total stretching ratio becomes 7 times, in a boric acid aqueous solution having concentration of 4.25 mass % at 50° C., the film was washed with water by being dipped in a water bath at 30° C., and dried at 50° C. for 4 minutes, and a polarizer A having a thickness of 8 µm was obtained.

<Saponification Treatment of Polarizing Plate Protective Film (Cellulose Acylate Film)

Each of the polarizing plate protective films 101 to 110, c01, and c02 and the cellulose acylate films S01 to S03 manufactured as described above was dipped in a sodium hydroxide aqueous solution having concentration of 2.3 mol/L at 55° C. for 3 minutes. Then, the film was washed in a water washing bath at room temperature (25° C.) and neutralized with sulfuric acid having concentration of 0.05 mol/L at 30° C. The film was washed in a water washing bath at room temperature (25° C.) again and dried over hot air at 100° C. By doing so, the saponification treatment of the film surface was performed with respect to each of the polarizing plate protective films 101 to 110, c01, and c02 and the cellulose acylate films S01 to S03.

(1) Manufacturing of Polarizing Plate H01

The saponified polarizing plate protective film 101 was bonded to one side of the polarizer A manufactured as described above with a polyvinyl alcohol-based adhesive. In addition, the saponified cellulose acylate film S01 was bonded to the opposite side of the polarizer so as to interpose the polarizer between the polarizing plate protective film 101 and the cellulose acylate film. At this time, a transmission axis of the polarizer and a width direction of the manufactured polarizing plate protective film or the cellulose acylate film are disposed to be parallel to each other.

By doing so, the polarizing plate H01 of the invention was manufactured.

(2) Manufacturing of Polarizing Plate H02 to H10. Hc1, and Hc2

The polarizing plates H02 to H11 of the invention and comparative polarizing plates Hc1, and Hc2 were prepared in the same manner as in the manufacturing of the polarizing plate H01, except for changing the polarizing plate protective film and the cellulose acylate film to those shown in the following Table 1.

C. Evaluation of Polarizing Plate Protective Film and Polarizing Plate

As shown below, regarding the polarizing plate incorporated in the polarizing plate protective film, the durability of the polarizing plate and the crystallization index of PVA in the polarizer were evaluated, and the performance of the polarizing plate protective film.

(Evaluation of Polarizing Sheet Durability)

Regarding each polarizing plate manufactured as described above, the orthogonal transmittance and parallel transmittance were measured by using automatic polarizing film measurement device VAP-7070 (product name) manufactured by JASCO Corporation, and the degree of polarization was calculated by the following expression.

Degree of polarization (%)={(average transmittance−orthogonal transmittance)/(average transmittance+orthogonal transmittance)}$^{1/2}$×100

Two samples (5 cm×5 cm) obtained by bonding the polarizing plate onto glass through a pressure sensitive adhesive were manufactured. At this time, the cellulose acylate film S01 to S03 were bonded to a side (air interface side) opposite to the glass. The orthogonal transmittance was measured by setting the glass side of this sample to face a light source. The measurement of the two samples was respectively performed, and an average value thereof was set as the orthogonal transmittance and the average transmittance.

After that, the degree of polarization of a sample after storage in the environment of a temperature of 80° C. and relative humidity of 90% for 144 hours was measured by the same method. The amount of a change of the degrees of polarization before and after the time elapse was obtained, and evaluation thereof was performed with the following standards.

In Table 1 described below, the amount of a change was shown as the polarizing sheet durability.

As the change in the degree of polarization is small, the polarizing sheet durability is preferable and C or higher levels are practical levels.

A: a change in a degree of polarization is smaller than 0.5%

B: a change in a degree of polarization is equal to or greater than 0.5% and smaller than 2%

C: a change in a degree of polarization is equal to or greater than 2% and smaller than 5%

D: a change in a degree of polarization is equal to or greater than 5%

(Crystallization Index of PVA in Polarizer)

The polarizing plate after storing at a temperature of 80° C. and relative humidity of 90% for 144 hours was dipped in methylene chloride at room temperature (25° C.) for 30 minutes, the polarizing plate protective film and the cellulose acylate films S01 to S03 are dissolved, and the polarizer was extracted as a film. The ATR-IR spectra of the surface of the polarizer on a side adjacent to the cellulose acylate films S01 to S03 by the infrared total reflection spectroscopy measurement method (ATR method) were measured by the following method, and the crystalline index of PVA was acquired by the following expression. A low crystalline index of PVA is preferable, the crystalline index is more preferably equal to or smaller than 0.05, and a case where the crystalline index is a negative value is particularly preferable.

Measurement device: Nicolet 6700 manufactured by Thermo Scientific Condition
Prism: germanium
Wavelength range: 400 $cm^{-1}$ to 4,000 $cm^{-1}$ $$\text{crystallization index of PVA} = \{A(1{,}141\ cm^{-1}) - A(1{,}134\ cm^{-1})\}/A(1{,}134\ cm^{-1})$$ Expression (α):

In Expression (α), $A(1{,}141\ cm^{-1})$ represents absorbency at a wave number of $1{,}141\ cm^{-1}$ and $A(1{,}134\ cm^{-1})$ represents absorbency at a wave number of $1{,}134\ cm^{1}$.

The obtained results are collectively shown in the following Table 1.

With respect to this, in the polarizing plate Hc2 to which the polarizing plate protective film to which the comparative compound is added is incorporated, the polarizing sheet durability was not improved compared to the polarizing plate Hc1, and the crystallization index of PVA of the polarizer after wet heat thermo was not changed.

In the polarizing plate to which the polarizing plate protective film including the compound represented by General Formula (I) of the invention is incorporated, the crystallization index of PVA of the polarizer after wet heat thermo is low, and thus, it is considered that the compound represented by General Formula (I) in the polarizing plate protective film is diffused to the polarizer under the wet heat condition to prevent crystallization of PVA of the polarizer.

Here, since the compound represented by General Formula (I) includes two or more formyl group or boronic acid group, or a formyl group or boronic acid group and one acetal group or a boronic ester group, the crosslinking of PVA can be performed, and it is assumed that the compound may contribute to the crosslinking of PVA or the re-crosslinking.

TABLE 1

| Polarizing plate No. | Glass side polarizing plate protective film | | | Air side polarizing plate protective film | | | | | | Crystallization index of PVA 80° C. 90% 144 hours | Note |
|---|---|---|---|---|---|---|---|---|---|---|---|
| | Polarizing plate protective film No. | Polarizer durability improving agent | | Cellulose acylate film No. | Additive B or E | | Barbituric Acid-Based Additive | | Polarizing plate durability | | |
| | | Type | Added amount(Note) | | Type | Added amount(Note) | Type | Added amount(Note) | | | |
| H01 | 101 | (D-1-1) | 7.0 | S01 | E-1 | 8 | A-3 | 4 | A | −0.06 | Present invention |
| H02 | 102 | (D-2-1) | 7.0 | S01 | E-1 | 8 | A-3 | 4 | B | 0.00 | Present invention |
| H03 | 103 | (D-2-2) | 7.0 | S01 | E-1 | 8 | A-3 | 4 | B | 0.05 | Present invention |
| H04 | 103 | (D-1-4) | 7.0 | S01 | E-1 | 8 | A-3 | 4 | C | 0.00 | Present invention |
| H05 | 104 | (D-1-1) | 14.0 | S01 | E-1 | 8 | A-3 | 4 | A | −0.07 | Present invention |
| H06 | 105 | (D-1-1) | 3.0 | S01 | E-1 | 8 | A-3 | 4 | B | −0.02 | Present invention |
| H07 | 106 | (D-1-1) | 1.5 | S01 | E-1 | 8 | A-3 | 4 | B | 0.02 | Present invention |
| H08 | 108 | (D-1-5) | 7.0 | S01 | E-1 | 8 | A-3 | 4 | A | −0.05 | Present invention |
| H09 | 109 | (D-1-1) | 1.5 | S02 | E-1 | 8 | None | 0 | C | 0.04 | Present invention |
| H10 | 110 | (D-1-1) | 3.0 | S03 | B-97 | 8 | A-3 | 4 | A | −0.04 | Present invention |
| Hc1 | c01 | — | 0.0 | S01 | E-1 | 8 | A-3 | 4 | D | 0.07 | Comparative Example |
| Hc2 | c02 | Comparative compound (1) | 1.5 | S01 | E-1 | 8 | A-3 | 4 | D | 0.07 | Comparative Example |

(Note)added amount with respect to 100 parts by mass of cellulose acylate (parts by mass)

From Table 1, all of the polarizing plates to which the polarizing plate protective film to which the compound represented by General Formula (I) of the invention is added is incorporated, has excellent polarizing sheet durability and a low crystallization index of PVA of the polarizer after wet heat thermo, compared to the polarizing plate Hc1 to which the comparative polarizing plate protective film to which the compound represented by General Formula (I) of the invention (shown as polarizing sheet durability improving agent in the table) is not added is incorporated.

Example 2

Polarizing plate protective films 201 to 222 were manufactured in the same manner as in Example 1, except for changing the polarizing sheet durability improving agent of the glass side polarizing plate protective film and the added amount thereof as shown in the following Table 2. In addition, polarizing plates H201 to H222 were manufactured in the same manner as in Example 1, except for using the cellulose acylate film S01 as the air side polarizing plate protective film.

In the manufactured polarizing plates, the polarizing sheet durability and the crystallization index of PVA in the polarizer were evaluated in the same manner as in Example 1.

However, evaluation standards of the polarizing sheet durability and the crystallization index of PVA in the polarizer were changed as follows.

Regarding the polarizing sheet durability, the level C or higher level are practical levels. A low crystallization index of PVA in the polarizer is preferable and the level C or higher level are success levels.

Evaluation of Polarizing Sheet Durability

A: a change in a degree of polarization is smaller than 0.5%

B: a change in a degree of polarization is equal to or greater than 0.5% and smaller than 2%

C: a change in a degree of polarization is equal to or greater than 2% and smaller than 5%

D: a change in a degree of polarization is equal to or greater than 5%

Evaluation of Crystallization Index of PVA in Polarizer

A: crystallization index is smaller than −0.03

B: crystallization index is equal to or greater than −0.03 and smaller than 0.00

C: crystallization index is equal to or greater than 0.00 and smaller than 0.03

D: crystallization index is equal to or greater than 0.03

The obtained results are collectively shown in the following Table 2.

In the same manner as in Example 1, in the polarizing plate to which the polarizing plate protective film to which the compound represented by General Formula (I) of the invention is added is incorporated, it is found that the crystallization index of PVA of the polarizer after wet heat thermo is low and excellent polarizing sheet durability is obtained.

Example 3

Polarizing plates H301 and H302 and comparative polarizing plates Hc31 and Hc32 were manufactured in the same manner as in Example 1, except for using the polarizing plate protective films 101 and c01 and the cellulose acylate films S01 manufactured in Example 1 as the glass side polarizing plate protective film and the air side polarizing plate protective film in combination as shown in the following Table 3, and changing the thickness of the polarizer of Example 1 as a thickness shown in the following Table 3.

The polarizing sheet durability of each polarizing plate manufactured was measured in the same manner as in Example 1.

However, the durability test, the storage was performed in the environment of a temperature of 80° C. and relative humidity of 90% for designated time shown in the following Table 3

The obtained results were evaluation with the following standards. Level B and higher levels are success levels.

TABLE 2

| | Glass side polarizing plate protective film | | | | | |
|---|---|---|---|---|---|---|
| | | Polarizer durability improving agent | | | Crystallization index | |
| Polarizing plate No. | Polarizing plate protective film No. | Type | Added amount[Note] | Polarizing plate durability | of PVA 80° C. 90% 144 hours | Note |
| H201 | 201 | (D-1-2) | 8.0 | A | A | Present invention |
| H202 | 202 | (D-1-3) | 8.0 | B | C | Present invention |
| H203 | 203 | (D-1-12) | 6.0 | B | C | Present invention |
| H204 | 204 | (D-1-14) | 6.0 | B | C | Present invention |
| H205 | 205 | (D-1-24) | 6.0 | B | C | Present invention |
| H206 | 206 | (D-1-25) | 6.0 | B | B | Present invention |
| H207 | 207 | (D-1-26) | 6.0 | B | C | Present invention |
| H208 | 208 | (D-1-27) | 6.0 | B | B | Present invention |
| H209 | 209 | (D-1-28) | 6.0 | B | B | Present invention |
| H210 | 210 | (D-1-29) | 6.0 | C | C | Present invention |
| H211 | 211 | (D-1-30) | 6.0 | C | C | Present invention |
| H212 | 212 | (D-1-31) | 6.0 | B | B | Present invention |
| H213 | 213 | (D-1-32) | 8.0 | B | B | Present invention |
| H214 | 214 | (D-1-34) | 8.0 | B | B | Present invention |
| H215 | 215 | (D-1-35) | 6.0 | A | A | Present invention |
| H216 | 216 | (D-3-1) | 6.0 | A | A | Present invention |
| H217 | 217 | (D-3-4) | 4.0 | B | B | Present invention |
| H218 | 218 | (D-3-4) | 8.0 | A | A | Present invention |
| H219 | 219 | (D-3-5) | 6.0 | A | A | Present invention |
| H220 | 220 | (D-3-6) | 6.0 | A | B | Present invention |
| H221 | 221 | (D-3-7) | 6.0 | A | B | Present invention |
| H222 | 222 | (D-3-12) | 6.0 | A | B | Present invention |

[Note] added amount with respect to 100 parts by mass of cellulose acytate (parts by mass)

A: a change in the degree of polarization is smaller than 1.0%

B: a change in the degree of polarization is equal to or greater than 1.0% and smaller than 5.0%

C: a change in the degree of polarization is equal to or greater than 5.0%

The obtained results are collectively shown in the following Table 3.

TABLE 3

| Polarizing plate No. | Glass side polarizing plate protective film | | | Polarizing plate | | | |
|---|---|---|---|---|---|---|---|
| | Polarizing plate protective film No. | Polarizer durability improving agent | | Air side polarizing plate protective film Cellulose acylate film No. | Polarizing plate durability 80° C. 90% | | |
| | | Type | Added amount[Note] | | Thickness of polarizer | Time | Evaluation level | Note |
| H301 | 101 | (D-1-1) | 7.0 | S01 | 15 μm | 216 h | A | Present invention |
| Hc31 | c01 | — | 0.0 | S01 | 15 μm | 216 h | C | Comparative Example |
| H302 | 101 | (D-1-1) | 7.0 | S01 | 27 μm | 336 h | B | Present invention |
| Hc32 | c01 | — | 0.0 | S01 | 27 μm | 336 h | C | Comparative Example |

[Note] added amount with respect to 100 parts by mass of cellulose acylate (parts by mass)

It is found that, even in a case where the thickness of the polarizer is not great, in the polarizing plate to which the polarizing plate protective film to which the compound represented by General Formula (I) of the invention is added is incorporated, excellent polarizing sheet durability is obtained.

Example 4

[Manufacturing of Polarizing Plate]
1. Polarizing Plate H401
1) Manufacturing of Cellulose Acetate Resin Sulfuric acid (7.8 parts by mass with respect to 100 parts by mass of cellulose) was added as a solvent, acetic acid was added thereto, and the acetylation reaction of cellulose was performed at 40° C. After the acetylation, aging was performed at 40° C. A low molecular weight component of the cellulose acetate was washed with acetone and removed.

Regarding the obtained cellulose acetate, the total degree of acetyl substitution (B) was 2.87 and the degree of polymerization was 370.

2) Manufacturing of Polarizing Plate Protective Film

The following composition including the cellulose acetate prepared as described above was put into a mixing tank and stirred to dissolve each component, and a cellulose acylate solution 401 was prepared. The additive B-104 is the exemplified compound B-104 described in the section of the additive.

Composition of Cellulose Acylate Solution 401
Cellulose acetate having the total degree of acetyl substitution (B) of 2.87 and the degree of polymerization of 370: 100.0 parts by mass
Exemplified compound (D-1-1): 6.5 parts by mass
Additive A-3: 4.0 parts by mass
Additive B-104: 8.0 parts by mass
Methylene chloride (first solvent): 402.0 parts by mass
Methanol (second solvent): 60.0 parts by mass The cellulose acetate solution 401 was casted by using a band casting machine, dried until the content of the remaining solvent becomes 40% at 100° C., and a film was stripped. The stripped film was further dried at the atmosphere temperature of 140° C. for 20 minutes. The thickness of the obtained polarizing plate protective film 401 was 40 μm.

3) Manufacturing of Polarizing Plate
(a) Saponification Treatment of Polarizing Plate Protective Film Each of the polarizing plate protective film 401 manufactured as described above and the cellulose acylate film S01 manufactured in Example 1 were respectively dipped in a sodium hydroxide aqueous solution having concentration of 2.3 mol/L at 55° C. for 3 minutes. Then, the film was washed in a water washing bath at room temperature (25° C.) and neutralized with sulfuric acid having concentration of 0.05 mol/L at 30° C. The film was washed in a water washing bath at room temperature (25° C.) again and dried over hot air at 100° C. By doing so, the saponification treatment of the film surface was performed with respect to each of the polarizing plate protective film 401 and the cellulose acylate film S01.

(b) Manufacturing of Polarizing Plate

The saponified polarizing plate protective film 401 was bonded to one side of the polarizer A manufactured in Example 1, with a polyvinyl alcohol-based adhesive. In addition, the saponified cellulose acylate film S01 was bonded to the opposite side of the polarizer so as to interpose the polarizer between the polarizing plate protective film 401 and the cellulose acylate film. At this time, a transmission axis of the polarizer and a width direction of the manufactured polarizing plate protective film or the cellulose acylate film are disposed to be parallel to each other.

By doing so, the polarizing plate H401 of the invention was manufactured.

2. Manufacturing of Polarizing Plates H402, Hc41 and Hc42

The polarizing plate H402 and comparative polarizing plates Hc41 and Hc42 were manufactured in the same manner as in the manufacturing of the polarizing plate H401, except for changing the air side polarizing plate protective film as the polarizing plate protective film including the polarizing sheet durability improving agent and the barbituric acid-based additive as the added amount shown in the following Table 4.

[Evaluation of Polarizing Plate Protective Film and Polarizing Plate]

As shown below, regarding the polarizing plate incorporated in the polarizing plate protective film, the durability of the polarizing plate was evaluated and the performance of the polarizing plate protective film.

(Evaluation of Polarizing Sheet Durability)

Regarding each polarizing plate manufactured as described above, the orthogonal transmittance and parallel transmittance were measured by using automatic polarizing film measurement device VAP-7070 (product name) manufactured by JASCO Corporation, and the degree of polarization was calculated by the following expression.

Degree of polarization (%)={(average transmittance−orthogonal transmittance)/(average transmittance+orthogonal transmittance)}$^{1/2}$×100

Two samples (5 cm×5 cm) obtained by bonding the polarizing plate onto glass through a pressure sensitive adhesive were manufactured. At this time, the cellulose acylate film S01 was bonded to a glass side. The orthogonal transmittance was measured by setting the glass side of this sample to face a light source. The measurement of the two samples was respectively performed, and an average value thereof was set as the orthogonal transmittance and the average transmittance.

After that, the degree of polarization of a sample after storage in the environment of a temperature of 80° C. and relative humidity of 90% for 336 hours was measured by the same method. The amount of a change of the degrees of polarization before and after the time elapse was obtained, and evaluation thereof was performed with the following standards.

In Table 4 described below, the amount of a change was shown as the polarizing sheet durability.

As the change in the degree of polarization is small, the polarizing sheet durability is preferable and B or higher levels are practical levels.

A: a change in a degree of polarization is smaller than 1.0%

B: a change in a degree of polarization is equal to or greater than 1.0% and smaller than 4.0%

C: a change in a degree of polarization is equal to or greater than 4.0% and smaller than 6.0%

D: a change in a degree of polarization is equal to or greater than 6.0%

The obtained results are collectively shown in the following Table 4.

From Table 4, it is found that, even in the polarizing plate in which the compound represented by General Formula (I) of the invention is used in the polarizing plate protective film on a side adjacent to the air interface (air side polarizing plate protective film), excellent polarizing sheet durability is obtained.

Example 5

[Manufacturing of Polarizing Plate]
1. Polarizing Plate H501
1) Manufacturing of Polarizing Plate Protective Film
(Manufacturing of Cellulose Acylate Solution 501)

The following composition was put in a mixing tank and stirred to dissolve each component, and a cellulose acylate solution 501 was prepared.

Composition of Cellulose Acylate Solution 501
Cellulose acetate having a degree of acetyl substitution of 2.87 and degree of polymerization of 350: 100.0 parts by mass
Additive F-1 (ester oligomer having mass average molecular weight of 1,000): 13.0 parts by mass
Exemplified compound (D-1-1): 7.0 parts by mass
Methylene chloride (first solvent): 419.0 parts by mass
Methanol (second solvent): 63.0 parts by mass

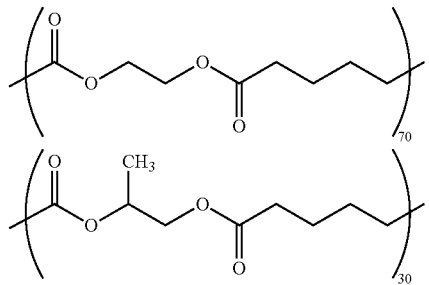

Additive F-1

Here, the numerical values of the chemical structural formula of the additive F-1 represents a molar ratio of each structure in the bracket.

TABLE 4

| | | | Air side polarizing plate protective film | | | | | |
|---|---|---|---|---|---|---|---|---|
| | Glass side polarizing plate protective film | | Polarizer durability improving agent | | Barbituric Acid-based additive | | Polarizing | |
| Polarizing plate No. | Cellulose acylate film No. | Polarizing plate protective film No. | Type | Added amount$^{(Note)}$ | Type | Added amount$^{(Note)}$ | plate durability | Note |
| H401 | S01 | 401 | (D-1-1) | 6.5 | — | — | B | Present invention |
| H402 | S01 | 402 | (D-1-1) | 6.5 | A-3 | 4 | A | Present invention |
| Hc41 | S01 | c41 | — | — | — | — | D | Comparative Example |
| Hc42 | S01 | c42 | — | — | A-3 | 4 | C | Comparative Example |

$^{(Note)}$added amount with respect to 100 parts by mass of cellulose acylate (parts by mass)

(Preparation of Matting Agent Solution 502)

The following composition was put in a disperser and stirred to dissolve each component, and a matting agent solution 502 was prepared.

Composition of Matting Agent Solution 502

Silica particles having an average particle size of 20 nm (AEROSIL R972 manufactured by Nippon Aerosil co. Ltd.): 2.0 parts by mass Methylene chloride (first solvent): 75.5 parts by mass Methanol (second solvent): 11.2 parts by mass Cellulose acylate solution 501: 0.9 parts by mass <Casting>

1.3 parts by mass of the matting agent solution 502 and 98.7 parts by mass of the cellulose acylate solution 501 were added and mixed with an in-line mixer. The prepared dope was casted on a stainless steel casting support (support temperature of 22° C.) by using a band casting machine. When the amount of solvent remaining in the dope become approximately 20 mass %, a formed film was stripped, and both ends of the stripped film in a width direction were grasped with a tenter, and the film in a state where the amount of remaining solvent is 5 to 10 mass % was stretched 1.04 times (4%) in a width direction at the temperature of 100° C. and dried. The stripped film was further dried in the atmosphere of 140° C. for 20 minutes. A thickness of the polarizing plate protective film 501 obtained was 25 μm.

2) Manufacturing of Polarizing Plate (a) Saponification Treatment of Polarizing Plate Protective Film Each of the polarizing plate protective film 501 manufactured as described above and the cellulose acylate film S01 manufactured in Example 1 were subjected to the saponification treatment of the film surface in the same manner as in Example 4.

[Evaluation of Polarizing Plate Protective Film and Polarizing Plate]

As shown below, regarding the polarizing plate incorporated in the polarizing plate protective film, the durability of the polarizing plate was evaluated and the performance of the polarizing plate protective film.

(Evaluation of Polarizing Sheet Durability)

Regarding each polarizing plate manufactured as described above, the degree of polarization was calculated in the same manner as in Example 4.

Two samples (5 cm×5 cm) obtained by bonding the polarizing plate onto glass through a pressure sensitive adhesive were manufactured. At this time, the cellulose acylate film S01 was bonded to a side opposite to the glass (air interface side). The orthogonal transmittance was measured by setting the glass side of this sample to face a light source. The measurement of the two samples was respectively performed, and an average value thereof was set as the orthogonal transmittance and the average transmittance.

After that, the degree of polarization of a sample after storage in the environment of a temperature of 85° C. and relative humidity of 85% for 120 hours was measured by the same method. The amount of a change of the degrees of polarization before and after the time elapse was obtained, and evaluation thereof was performed with the following standards. The B and higher levels are success levels.

A: a change in a degree of polarization is smaller than 1.0%

B: a change in a degree of polarization is equal to or greater than 1.0% and smaller than 5.0%

C: a change in a degree of polarization is equal to or greater than 5.0%

The obtained results are collectively shown in the following Table 5.

TABLE 5

| | Glass side polarizing plate protective film | | | | | |
|---|---|---|---|---|---|---|
| | | Polarizer durability improving agent | | Air side polarizing plate | | |
| Polarizing plate No. | Polarizing plate protective film No. | Type | Added amount(Note) | protective film Cellulose acylate film No. | Polarizing plate durability 80° C. 85% 120 hours | Note |
| H501 | 501 | (D-1-1) | 7.0 | S01 | B | Present invention |
| H502 | 502 | (D-1-25) | 7.0 | S01 | B | Present invention |
| H503 | 503 | (D-3-5) | 7.0 | S01 | B | Present invention |
| Hc51 | c51 | — | — | S01 | C | Comparative Example |

(Note)added amount with respect to 100 parts by mass of cellulose acylate (parts by mass)

(b) Manufacturing of Polarizing Plate

The polarizing plate H501 of the invention was manufactured in the same manner as in Example 4, by using the saponified polarizing plate protective film 501 and the saponified cellulose acylate film S01.

2. Manufacturing of Polarizing Plates $H_{502}$, $H_{503}$, and Hc51

The polarizing plates $H_{502}$ and $H_{503}$ of the invention and comparative polarizing plate Hc51 were manufactured in the same manner as in the manufacturing of the polarizing plate H501, except for changing the polarizing sheet durability improving agent of the glass side polarizing plate protective film and the added amount thereof as shown in the following Table 5.

From Table 5, it is found that, even in the polarizing plate in which the compound represented by General Formula (I) of the invention is used in the glass side polarizing plate protective film, excellent polarizing sheet durability is obtained.

From the result described above, it is possible to manufacture a liquid crystal display device having excellent polarizing sheet durability by using the polarizing plate of the invention.

The invention has been described based on the embodiments, but the invention is not limited in any section of the description unless otherwise noted, and the invention may be widely interpreted within a range not departing from a gist and a scope of the invention shown in the accompanying claims.

EXPLANATION OF REFERENCES

1: upper side polarizing plate
2: direction of upper side polarizing plate absorbing axis
3: electrode substrate on liquid crystal cell
4: orientation control direction of upper substrate
5: liquid crystal layer
6: electrode substrate below liquid crystal cell
7: orientation control direction of lower substrate
8: lower side polarizing plate
9: direction of lower side polarizing plate absorbing axis
10: liquid crystal display device

What is claimed is:

1. A polarizing plate protective film comprising: a compound represented by the following General Formula (I),

  General Formula (I)

in General Formula (I), X represents a formyl group, and a group represented by the following General Formula (I-B) or a group represented by the following General Formula (I-C), L represents a single bond or divalent linking group, and n represents an integer equal to or greater than 2; when n is 2, Z represents a single bond or a divalent group, and when n is equal to or greater than 3, Z represents an n-valent group where a plurality of -L-X's may be the same as each other or different from each other; however, among a plurality of X's, the number of the group represented by General Formula (I-B) and the group represented by the General Formula (I-C) is respectively 0 or 1, and when n is 2, both of L and Z may not be a single bond,

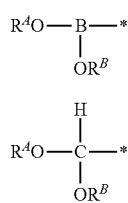

in General Formulae (I-B) and (I-C), $R^A$ and $R^B$ each independently represent an alkyl group, a cycloalkyl group, an aryl group, or an acyl group where, $R^A$ and $R^B$ may be bonded to each other to form a ring; and * represents a bond to be bonded to L.

2. The polarizing plate protective film according to claim 1, wherein the compound represented by General Formula (I) is represented by any of the following General Formulae (II-1) to (II-5),

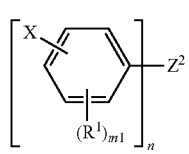

General Formula (II-1)

  General Formula (II-2)

General Formula (II-3)

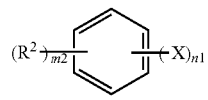

General Formula (II-4)

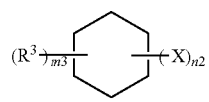

General Formula (II-5)

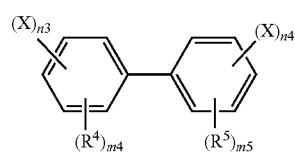

in General Formulae (II-1) to (II-5), X and n are identical to X and n of General Formula (I); when n is 2, $Z^2$ represents a divalent group, and when n is equal to or greater than 3, $Z^2$ represents an n-valent group; when n is 2, $Z^3$ represents an alkylene group, and when n is equal to or greater than 3, $Z^3$ represents an n-valent alkyl group; however, $Z^3$ does not have a ring structure; $R^1$ to $R^5$ each independently represent a substituent; n1 represents an integer of 2 to 6, n2 represents an integer of 2 to 12, and n3 and n4 each independently represent an integer of 1 to 5; and m1, m2, m4, and m5 each independently represent an integer of 0 to 4, and m3 represents an integer of 0 to 10.

3. The polarizing plate protective film according to claim 1, wherein the compound represented by General Formula (I) includes at least one benzene ring.

4. The polarizing plate protective film according to claim 1, wherein the compound represented by General Formula (I) is represented by General Formula (II-1) or (II-3).

5. The polarizing plate protective film according to claim 1, wherein the n is an integer of 2 to 4, and the total number of carbon atoms of component parts other than X is equal to or smaller than 40.

6. The polarizing plate protective film according to claim 1, wherein the number of shortest linking atoms which link two X's with each other is equal to or smaller than 20 between every two X's.

7. The polarizing plate protective film according to claim 1, wherein the Z is a single bond, —O—, —S—, —SO—, —SO$_2$—, —OC(=O)—, —C($R^{a1}$)($R^{a2}$)—, >C<, (—OCH$_2$CH$_2$)$_2$C(CH2CH2O—)$_2$, >C($R^{a3}$)—, >N—, or —N(Ra)—, $R^{a1}$ to $R^{a3}$ each independently represent a hydrogen atom, an alkyl group, or an aryl group, and Ra represents a hydrogen atom, an alkyl group, an aryl group, or an acyl group.

8. The polarizing plate protective film according to claim 1, including cellulose acylate.

9. A polarizing plate comprising:
the polarizing plate protective film according to claim 1 on both sides or one side of a polarizer.

10. The polarizing plate according to claim 9 further comprising:

a compound represented by the following General Formula (A) on at least one polarizing plate protective film which is bonded to both sides or one side of the polarizer,

General Formula (A)

in General Formula (A), $R^{41}$ and $R^{43}$ each independently represent a hydrogen atom, an alkyl group, a cycloalkyl group, an alkenyl group, or an aromatic group where an alkyl group, a cycloalkyl group, an alkenyl group, or an aromatic group may include a substituent; and $R^{45}$ represents a hydrogen atom or a substituent.

11. A display device comprising at least one polarizing plate according to claim 9.

* * * * *